US006451810B1

(12) United States Patent
Coleman et al.

(10) Patent No.: US 6,451,810 B1
(45) Date of Patent: Sep. 17, 2002

(54) AMIDE SUBSTITUTED IMIDAZOQUINOLINES

(75) Inventors: Patrick L. Coleman, Minneapolis; Stephen L. Crooks, Mahtomedi, both of MN (US); Kyle J. Lindstrom, Houlton; Bryon A. Merrill, River Falls, both of WI (US); Michael J. Rice, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/589,580

(22) Filed: Jun. 7, 2000

Related U.S. Application Data

(60) Provisional application No. 60/138,365, filed on Jun. 10, 1999.

(51) Int. Cl.[7] .................. A01N 43/42; A61K 31/44; C07D 515/00
(52) U.S. Cl. ............................ 514/293; 546/82
(58) Field of Search ................. 514/293; 546/82

(56) References Cited

U.S. PATENT DOCUMENTS

| | | | |
|---|---|---|---|
| 3,314,941 A | 4/1967 | Littell et al. | 260/239.3 |
| 3,917,624 A | 11/1975 | El-Haj et al. | 260/294.9 |
| 4,689,338 A | 8/1987 | Gerster | 514/293 |
| 4,698,348 A | 10/1987 | Gerster | 514/293 |
| 4,929,624 A | 5/1990 | Gerster et al. | 514/293 |
| 5,037,986 A | 8/1991 | Gerster | 546/82 |
| 5,266,575 A | 11/1993 | Gerster | 514/293 |
| 5,268,376 A | 12/1993 | Gerster | 514/293 |
| 5,346,905 A | 9/1994 | Gerster | 514/293 |
| 5,352,784 A | 10/1994 | Nikolaides et al. | 594/126 |
| 5,389,640 A | 2/1995 | Gerster et al. | 514/293 |
| 5,444,065 A | 8/1995 | Nikolaides et al. | 514/293 |
| 5,446,153 A | 8/1995 | Lindstrom et al. | 544/127 |
| 5,482,936 A | 1/1996 | Lindstrom | 514/183 |
| 5,494,916 A | 2/1996 | Lindstrom et al. | 514/303 |
| 5,585,612 A | 12/1996 | Harp, Jr. | 235/51 |
| 5,605,899 A | 2/1997 | Gerster et al. | 514/232.8 |
| 5,627,281 A | 5/1997 | Nikolaides et al. | 546/112 |
| 5,644,063 A | 7/1997 | Lindstrom et al. | 546/294 |
| 5,648,516 A | 7/1997 | Nikolaides et al. | 560/125 |
| 5,714,608 A | 2/1998 | Gerster | 546/82 |
| 5,741,909 A | 4/1998 | Gerster et al. | 546/82 |
| 5,886,006 A | 3/1999 | Nikolaides et al. | 514/293 |
| 5,977,366 A | 11/1999 | Gerster et al. | 546/159 |
| 6,069,149 A | 5/2000 | Nanba et al. | 514/293 |

FOREIGN PATENT DOCUMENTS

| | | |
|---|---|---|
| EP | 0 894 797 A1 | 2/1998 |
| JP | 9-208584 | 8/1997 |
| WO | WO 93/09119 | 5/1993 |
| WO | WO 97/48704 | 12/1997 |
| WO | WO 00/06577 | 2/2000 |
| WO | WO 00/09506 | 2/2000 |

OTHER PUBLICATIONS

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society,* 102, pp 511–513, Dec. 12, 1983.

Brennan, et al, "Automated Bioassay of Interferons in Micro–test Plates", *Biotechniques,* Jun./Jul., 78, 1983.

Testerman, et al, "Cytokine Induction by the Immunomodulators Imiquimod and S–27609", *Journal of Leukocyte Biology,* vol. 58, pp. 365–372, Sep. 1995.

Bachman, et al, "Synthesis of Substituted Quinolylamines. Derivatives of 4–Amino–7–Chloroquinoline", *J. Org. Chem,* 15, pp 1278–1284 (1950).

Jain, et al, "Chemical and Pharmacological Investigations of Some ω–Substituted Alkylamino–3–aminopyridines", *J. Med. Chem.,* 11, pp 87–92 (1968).

Baranov, et al., *Chem. Abs.* 85, 94371, (1976).

Berényi, et al, "Ring Transformation of Condensed Dihydro–as–triazines", *J. Heterocyclic Chem.,* 18, pp 1537–1540 (1981).

*Primary Examiner*—Mukund J. Shah
*Assistant Examiner*—Tamthom N. Truong
(74) *Attorney, Agent, or Firm*—MarySusan Howard; Ted K. Ringsred; Robert W. Sprague

(57) ABSTRACT

Imidazoquinoline and tetrahydroimidazoquinoline compounds that contain amide functionality at the 1-position are useful as immune response modifiers. The compounds and compositions of the invention can induce the biosynthesis of various cytokines and are useful in the treatment of a variety of conditions including viral diseases and neoplastic diseases.

64 Claims, No Drawings

AMIDE SUBSTITUTED IMIDAZOQUINOLINES

This is a continuation of Application No. 60/138,365 filed Jun. 10, 1999.

FIELD OF THE INVENTION

This invention relates to imidazoquinoline compounds that have an amide containing substituent at the 1-position, and to pharmaceutical compositions containing such compounds. A further aspect of this invention relates to the use of these compounds as immunomodulators, for inducing cytokine biosynthesis in animals, and in the treatment of diseases, including viral and neoplastic diseases.

BACKGROUND OF THE INVENTION

The first reliable report on the 1H-imidazo[4,5-c] quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl) ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo [4,5-c]quinolines, and Berenyi et al., *J. Heterocyclic Chem.* 18, 1537–1540 (1981), have reported certain 2-oxoimidazo [4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system. For example, EP 894 797 describes imidazoquinoline compounds that bear an amide containing substituent at the 1-position. The active compounds of this series require a terminal amine substituent that may be incorporated into a heterocyclic ring. As another example, WO 00/09506 describes imidazopyridine and imidazoquinoline compounds that may have an amide or urea containing substituent at the 1-position. The compounds described in this publication as having utility contain a 1-substituent wherein the amide or urea nitrogen is part of a heterocyclic ring. Despite these attempts to identify compounds that are useful as immune response modifiers, there is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazoquinoline-4-amine and tetrahydroimidazoquinoline-4-amine compounds that have an amide containing substituent at the 1-position. The compounds which have been found to be useful inducers of cytokine biosynthesis are defined by Formulae (I), (Ia), and (Ib), which are defined in more detail infra. These compounds share the general structural formula (I):

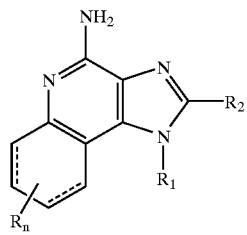

wherein $R_1$, $R_2$, and R are as defined herein for each class of compounds having formulas (I), (Ia), and (Ib). The invention also provides novel compounds of formulas (Ic), (Id), and (Ie) as defined herein, which compounds are also useful as immune response modifiers and which also have the same general structural formula (I) above.

The compounds of Formulae (I), (Ia), (Ib), (Ic), (Id), and (Ie) are useful as immune response modifiers due to their ability to induce cytokine biosynthesis and otherwise modulate the immune response when administered to animals. This makes the compounds useful in the treatment of a variety of conditionssuch as viral diseases and tumors that are responsive to such changes in the immune response.

The invention further provides pharmaceutical compositions containing the immune response modifying compounds, and methods of inducing cytokine biosynthesis in an animal, treating a viral infection in an animal, and/or treating a neoplastic disease in an animal by administering a compound of Formula (I), (Ia), (Ib), (Ic), (Id), or (Ie) to the animal.

In addition, methods of synthesizing the compounds of the invention and intermediates useful in the synthesis of these compounds are provided.

DETAILED DESCRIPTION OF THE INVENTION

As mentioned earlier, we have found that certain compounds induce cytokine biosynthesis and modify the immune response in animals. Such compounds are represented by Formulae (I), (Ia), (Ib), (Ic), (Id), and (Ie), as shown below.

The invention provides pharmaceutical compositions containing a therapeutically effective amount of a compound of Formula (I):

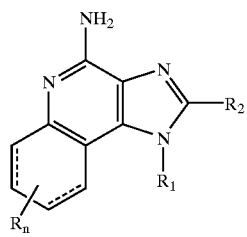

wherein
$R_1$ is -alkyl-$NR_3$—CO—$R_4$ or -alkenyl-$NR_3$—CO—$R_4$ wherein $R_4$ is aryl, heteroaryl, alkyl or alkenyl, each of which may be unsubstituted or substituted by one or more substituents selected from the group consisting of:
-alkyl;
-alkenyl;
-alkynyl;

-(alkyl)$_{0-1}$-aryl;
-(alkyl)$_{0-1}$-(substituted aryl);
-(alkyl)$_{0-1}$-heteroaryl;
-(alkyl)$_{0-1}$-(substituted heteroaryl);
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—P(O)(OR$_3$)$_2$;
—NR$_3$—CO—O-alkyl;
—N$_3$;
-halogen;
—NO$_2$;
—CN;
-haloalkyl;
—O-haloalkyl;
—CO-haloalkyl;
—OH;
—SH; and in the case of alkyl, alkenyl, or heterocyclyl, oxo;
or R$_4$ is

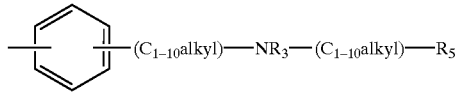

wherein R$_5$ is an aryl, (substituted aryl), heteroaryl, (substituted heteroaryl), heterocyclyl or (substituted heterocyclyl) group;

R$_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl;
-alkyl-O-alkenyl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-(substituted aryl);
-heteroaryl;

-(substituted heteroaryl);
-heterocyclyl;
-(substituted heterocyclyl);
—CO-aryl; and
—CO-heteroaryl;
each R$_3$ is independently selected from the group consisting of hydrogen; C$_{1-10}$ alkyl-heteroaryl; C$_{1-10}$ alkyl-(substituted heteroaryl); C$_{1-10}$ alkyl-aryl; C$_{1-10}$ alkyl-(substituted aryl) and C$_{1-10}$ alkyl;
n is 0 to 4;
and each R present is independently selected from the group consisting of C$_{1-10}$ alkyl C$_{1-10}$ alkoxy, halogen and trifluoromethyl, or a pharmaceutically acceptable salt thereof, in combination with a therapeutically effective carrier.

The invention also provides pharmaceutical compositions comprising a therapeutically effective amount of a compound of Formula (Ia):

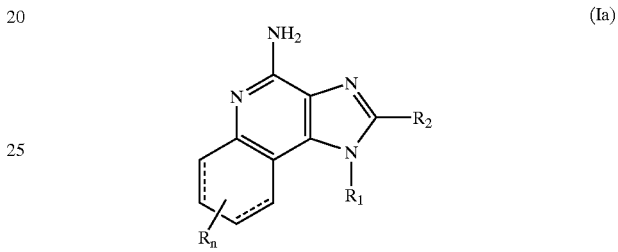

wherein
R$_1$ is -alkyl-NR$_3$—CO—R$_4$ or -alkenyl-NR$_3$—CO—R$_4$ wherein R$_4$ is aryl, heteroaryl, alkyl or alkenyl, each of which may be unsubstituted or substituted by one or more substituents selected from the group consisting of:
-heterocyclyl;
-(substituted heterocyclyl);
-(alkyl)$_{0-1}$heterocyclyl;
-(alkyl)$_{0-1}$(substituted heterocyclyl);
—O-(alkyl)$_{0-1}$heterocyclyl;
—O-(alkyl)$_{0-1}$(substituted heterocyclyl);
—S(O)$_{0-2}$-(alkyl)$_{0-1}$heterocyclyl; and
—S(O)$_{0-2}$-(alkyl)$_{0-1}$(substituted heterocyclyl);

R$_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl;
-alkyl-O-alkenyl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-(substituted aryl);

-heteroaryl;
-(substituted heteroaryl);
-heterocyclyl;
-(substituted heterocyclyl);
—CO-aryl; and
—CO-heteroaryl;

each $R_3$ is independently selected from the group consisting of hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

n is 0 to 4;

and each R present is independently selected from the group consisting of $C_{1-10}$ alkyl, $C_{1-10}$ alkoxy, halogen and trifluoromethyl, or a pharmaceutically acceptable salt thereof, in combination with a pharmaceutically acceptable carrier.

The invention further provides pharmaceutical compositions comprising a therapeutically effective amount of a compound of Formula (Ib):

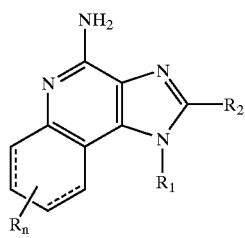

(Ib)

wherein $R_1$ is -alkyl-$NR_3$—CO—$R_4$ or -alkenyl-$NR_3$—CO—$R_4$ wherein $R_4$ is heterocyclyl which may be unsubstituted or substituted by one or more substituents selected from the group consisting of:
-alkyl;
-alkenyl;
-alkynyl;
-(alkyl)$_{0-1}$-aryl;
-(alkyl)$_{0-1}$-(substituted aryl);
-(alkyl)$_{0-1}$-heterocyclyl;
-(alkyl)$_{0-1}$-(substituted heterocyclyl);
-(alkyl)$_{0-1}$-heteroaryl;
-(alkyl)$_{0-1}$-(substituted heteroaryl);
—O-alkyl;
—O-(alkyl)$_{0-1}$-aryl;
—O-(alkyl)$_{0-1}$-(substituted aryl);
—O-(alkyl)$_{0-1}$-heterocyclyl;
—O-(alkyl)$_{0-1}$-(substituted heterocyclyl);
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heterocyclyl;
—S(O)$_{0-2}$-(alkyl)$_{0-1}$-(substituted heterocyclyl);
—S(O)$_{0-2}$-(alkyl)$_{0-1}$-heteroaryl;
—S(O)$_{0-2}$-(alkyl)$_{0-1}$-(substituted heteroaryl);
—P(O)(O$R_3$)$_2$;
—N$R_3$—CO—O-alkyl;
—N$_3$;
-halogen;
—NO$_2$;
—CN;
-haloalkyl;
—O-haloalkyl;
—CO-haloalkyl;
—OH;
—SH;
or $R_4$ is

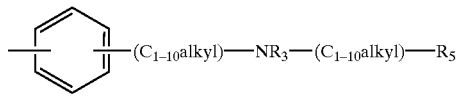

wherein $R_5$ is an aryl, (substituted aryl), heteroaryl, (substituted heteroaryl), heterocyclyl or (substituted heterocyclyl) group;

$R_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl;
-alkyl-O-alkenyl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—N$_3$;
-aryl;
-(substituted aryl);
-heteroaryl;
-(substituted heteroaryl);
-heterocyclyl;
-(substituted heterocyclyl);
—CO-aryl; and
—CO-heteroaryl;

each $R_3$ is independently selected from the group consisting of hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

n is 0 to 4;

and each R present is independently selected from the group consisting of $C_{1-10}$ alkyl, $C_{1-10}$ alkoxy, halogen and trifluoromethyl, or a pharmaceutically acceptable salt thereof, in combination with a pharmaceutically acceptable carrier.

The invention also provides compounds that are useful as immune response modifiers. One such class of compounds has structural Formula (Ic):

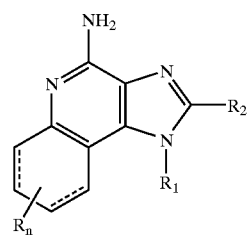

(Ic)

wherein

R₁ is -alkyl-NR₃—CO—R₄ or -alkenyl-NR₃—CO—R₄ wherein R₄ is aryl, heteroaryl, heterocyclyl, alkyl or alkenyl, each of which may be unsubstituted or substituted by one or more substituents selected from the group consisting of:
- -alkyl;
- -alkenyl;
- -alkynyl;
- -(alkyl)$_{0-1}$-aryl;
- -(alkyl)$_{0-1}$-(substituted aryl);
- -(alkyl)$_{0-1}$-heteroaryl;
- -(alkyl)$_{0-1}$-(substituted heteroaryl);
- -(alkyl)$_{0-1}$-heterocyclyl;
- -(alkyl)$_{0-1}$-(substituted heterocyclyl);
- —O-alkyl;
- —O-(alkyl)$_{0-1}$-aryl;
- —O-(alkyl)$_{0-1}$-(substituted aryl);
- —O-(alkyl)$_{0-1}$-heteroaryl;
- —O-(alkyl)$_{0-1}$-(substituted heteroaryl);
- —O-(alkyl)$_{0-1}$-heterocyclyl;
- —O-(alkyl)$_{0-1}$-(substituted heterocyclyl);
- —CO-aryl;
- —CO-(substituted aryl);
- —CO-heteroaryl;
- —CO-(substituted heteroaryl);
- —COOH;
- —CO—O-alkyl;
- —CO-alkyl;
- —S(O)$_{0-2}$-alkyl;
- —S(O)$_{0-2}$-(alkyl)$_{0-1}$-aryl;
- —S(O)$_{0-2}$-(alkyl)$_{0-1}$-(substituted aryl);
- —S(O)$_{0-2}$-(alkyl)$_{0-1}$-heteroaryl;
- —S(O)$_{0-2}$-(alkyl)$_{0-1}$-(substituted heteroaryl);
- —S(O)$_{0-2}$-(alkyl)$_{0-1}$-heterocyclyl;
- —S(O)$_{0-2}$-(alkyl)$_{0-1}$-(substituted heterocyclyl);
- —P(O)(OR₃)₂;
- —NR₆—CO—O-alkyl;
- —N₃;
- -halogen;
- —NO₂;
- —CN;
- -haloalkyl;
- —O-haloalkyl;
- —CO-haloalkyl;
- —OH;
- —SH; and in the case of alkyl, alkenyl, or heterocyclyl, oxo;

or R₄ is

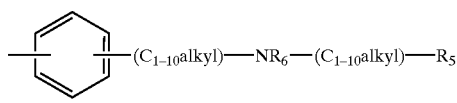

wherein R₅ is an aryl, (substituted aryl), heteroaryl, (substituted heteroaryl), heterocyclyl or (substituted heterocyclyl) group;

R₂ is selected from the group consisting of:
- -hydrogen;
- -alkyl;
- -alkenyl;
- -aryl;
- -(substituted aryl);
- -heteroaryl;
- -(substituted heteroaryl);
- -heterocyclyl;
- -(substituted heterocyclyl);
- -alkyl-O-alkyl;
- -alkyl-O-alkenyl; and
- -alkyl or alkenyl substituted by one or more substituents selected from the group consisting of:
    - —OH;
    - -halogen;
    - —N(R₆)₂;
    - —CO—N(R₆)₂;
    - —CO—C$_{1-10}$ alkyl;
    - —CO—O—C$_{1-10}$ alkyl;
    - —N₃;
    - -aryl;
    - -(substituted aryl);
    - -heteroaryl;
    - -(substituted heteroaryl);
    - -heterocyclyl;
    - -(substituted heterocyclyl);
    - —CO-aryl; and
    - —CO-heteroaryl;

R₃ is selected from the group consisting of C$_{1-10}$ alkyl-heteroaryl; C$_{1-10}$ alkyl-(substituted heteroaryl); C$_{1-10}$ alkyl-aryl; C$_{1-10}$ alkyl-(substituted aryl) and C$_{1-10}$ alkyl;

each R₆ is independently selected from the group consisting of hydrogen; C$_{1-10}$ alkyl-heteroaryl; C$_{1-10}$ alkyl-(substituted heteroaryl); C$_{1-10}$ alkyl-aryl; C$_{1-10}$ alkyl-(substituted aryl) and C$_{1-10}$ alkyl;

n is 0 to 4;

and each R present is independently selected from the group consisting of C$_{1-10}$ alkyl, C$_{1-10}$ alkoxy, halogen and trifluoromethyl, or a pharmaceutically acceptable salt thereof.

Another class of compounds provided by the invention is described by Formula (Id):

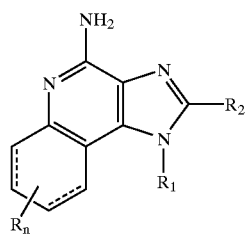

(Id)

wherein $R_1$ is -alkyl-$NR_3$—CO—$R_4$ or -alkenyl-$NR_3$—CO—$R_4$ wherein $R_4$ is aryl or heteroaryl which may be unsubstituted or substituted by one or more substituents selected from the group consisting of:
- alkyl;
- alkenyl;
- alkynyl;
- -(alkyl)$_{0-1}$-aryl;
- -(alkyl)$_{0-1}$-(substituted aryl);
- -(alkyl)$_{0-1}$-heteroaryl;
- -(alkyl)$_{0-1}$-(substituted heteroaryl);
- -(alkyl)$_{0-1}$-heterocyclyl;
- -(alkyl)$_{0-1}$-(substituted heterocyclyl);
- —O-alkyl;
- —O-(alkyl)$_{0-1}$-aryl;
- —O-(alkyl)$_{0-1}$-(substituted aryl);
- —O-(alkyl)$_{0-1}$-heteroaryl;
- —O-(alkyl)$_{0-1}$-(substituted heteroaryl);
- —O-(alkyl)$_{0-1}$-heterocyclyl;
- —O-(alkyl)$_{0-1}$-(substituted heterocyclyl);
- —CO-aryl;
- —CO-(substituted aryl);
- —CO-heteroaryl;
- —CO-(substituted heteroaryl);
- —COOH;
- —CO—O-alkyl;
- —CO-alkyl;
- —S(O)$_{0-2}$-alkyl;
- —S(O)$_{0-2}$-(alkyl)$_{0-1}$-aryl;
- —S(O)$_{0-2}$-(alkyl)$_{0-1}$-(substituted aryl);
- —S(O)$_{0-2}$-(alkyl)$_{0-1}$-heteroaryl;
- —S(O)$_{0-2}$-(alkyl)$_{0-1}$-(substituted heteroaryl);
- —S(O)$_{0-2}$-(alkyl)$_{0-1}$-heterocyclyl;
- —S(O)$_{0-2}$-(alkyl)$_{0-1}$-(substituted heterocyclyl);
- —P(O)(O$R_3$)$_2$;
- —$NR_3$—CO—O-alkyl;
- —$N_3$;
- -halogen;
- —$NO_2$;
- —CN;
- -haloalkyl;
- —O-haloalkyl;
- —CO-haloalkyl;
- —OH; and
- —SH;

$R_2$ is selected from the group consisting of:
- hydrogen;
- alkyl;
- alkenyl;
- aryl;
- -(substituted aryl);
- heteroaryl;
- -(substituted heteroaryl);
- heterocyclyl;
- -(substituted heterocyclyl);
- -alkyl-O-alkyl;
- -alkyl-O-alkenyl; and
- -alkyl or alkenyl substituted by one or more substituents selected from the group consisting of:
  - —OH;
  - -halogen;
  - —N($R_3$)$_2$;
  - —CO—N($R_3$)$_2$;
  - —CO—$C_{1-10}$ alkyl;
  - —CO—$C_{1-10}$ alkyl;
  - —$N_3$;
  - -aryl;
  - -(substituted aryl);
  - -heteroaryl;
  - -(substituted heteroaryl);
  - -heterocyclyl;
  - -(substituted heterocyclyl);
  - —CO-aryl; and
  - —CO-heteroaryl;

each $R_3$ is independently selected from the group consisting of hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

n is 0 to 4;

and each R present is independently selected from the group consisting of $C_{1-10}$ alkyl, $C_{1-10}$ alkoxy, halogen and trifluoromethyl, or a pharmaceutically acceptable salt thereof, with the proviso that $R_4$ is not an unsubstituted benzene ring, and that when $R_4$ is a substituted benzene ring the substituents are selected from the group consisting of $C_{1-20}$ alkyl, $C_{2-20}$ alkoxy, $C_{1-20}$ alkylthio, hydroxy, haloalkyl, haloalkylcarbonyl, haloalkoxy, $C_{1-20}$alkylcarbonyl, $C_{1-20}$alkenylcarbonyl, arylcarbonyl, heteroarylcarbonyl, aryl, arylalkyl, heteroaryl, heteroarylalkyl, heterocyclyl, heterocycloalkyl, nitrile, $C_{1-20}$ alkoxycarbonyl, $C_{1-20}$alkanoyloxy, $C_{1-20}$alkanoylthio, oxo and —($C_{1-10}$alkyl)-$NR_3$—($C_{1-10}$alkyl)-$R_5$, wherein $R_5$ is an aryl, (substituted aryl), heteroaryl, (substituted heteroaryl), heterocyclyl or (substituted heterocyclyl) group.

A further class of compounds provided by the invention is described by Formula (Ie):

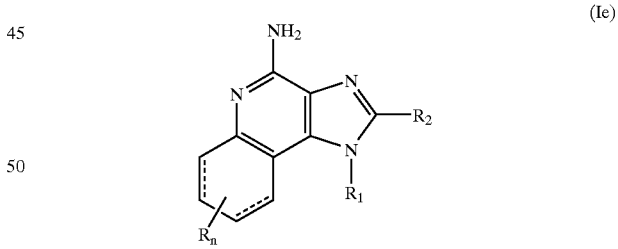

(Ie)

wherein $R_1$ is -alkyl-$NR_3$—CO—$R_4$ or -alkenyl-$NR_3$—CO—$R_4$ wherein $R_4$ is an alkyl or alkenyl group that is substituted by one or more substituents selected from the group consisting of:
- alkynyl;
- -(substituted aryl) wherein the substituent(s) are independently selected from the group consisting of alkyl, alkoxy, alkylthio, hydroxy, haloalkyl, haloalkylcarbonyl, haloalkoxy, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, and alkanoylthio;

-(substituted aryl);
-heteroaryl;
-(substituted heteroaryl);
—O-alkyl;
—O-(alkyl)$_{0-1}$-(substituted aryl) wherein the substituent(s) are independently selected from the group consisting of alkyl, alkoxy, alkylthio, hydroxy, haloalkyl, haloalkylcarbonyl, haloalkoxy, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, and alkanoylthio;
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—P(O)(OR$_3$)$_2$;
—NR$_3$—CO—O-alkyl;
—N$_3$;
—NO$_2$;
—CN;
—O-haloalkyl;
—CO-haloalkyl;
—OH;
—SH; and oxo;
R$_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl;
-alkyl-O-alkenyl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-(substituted aryl);
-heteroaryl;
-(substituted heteroaryl);
-heterocyclyl;
-(substituted heterocyclyl);
—CO-aryl; and
—CO-heteroaryl;
each R$_3$ is independently selected from the group consisting of hydrogen; C$_{1-10}$ alkyl-heteroaryl; C$_{1-10}$ alkyl-(substituted heteroaryl); C$_{1-10}$ alkyl-aryl; C$_{1-10}$ alkyl-(substituted aryl) and C$_{1-10}$ alkyl;

n is 0 to 4;
and each
R present is independently selected from the group consisting of C$_{1-10}$ alkyl, C$_{1-10}$ alkoxy, halogen and trifluoromethyl, or a pharmaceutically acceptable salt thereof.

Preparation of the Compounds

Imidazoquinolines of the invention can be prepared according to Reaction Scheme I where R, R$_1$, R$_2$ and n are as defined above.

In step (1) of Reaction Scheme I a 4-chloro-3-nitroquinoline of Formula II is reacted with an amine of Formula R$_1$NH$_2$ to provide a 3-nitroquinolin-4-amine of Formula III. The reaction can be carried out by adding amine to a solution of a compound of Formula II in a suitable solvent such as chloroform or dichloromethane and optionally heating. Many quinolines of Formula II are known compounds (see for example, U.S. Pat. No. 4,689,338 and references cited therein).

In step (2) of Reaction Scheme I a 3-nitroquinolin-4-amine of Formula III is reduced to provide a quinoline-3,4-diamine of Formula IV. Preferably, the reduction is carried out using a conventional heterogeneous hydrogenation catalyst such as platinum on carbon or palladium on carbon. The reaction can conveniently be carried out on a Parr apparatus in a suitable solvent such as isopropyl alcohol or toluene.

In step (3) of Reaction Scheme I a quinoline-3,4-diamine of Formula IV is reacted with a carboxylic acid or an equivalent thereof to provide a 1H-imidazo[4,5-c]quinoline of Formula V. Suitable equivalents to carboxylic acid include acid halides, orthoesters, and 1,1-dialkoxyalkyl alkanoates. The carboxylic acid or equivalent is selected such that it will provide the desired R$_2$ substituent in a compound of Formula V. For example, triethyl orthoformate will provide a compound where R$_2$ is hydrogen and triethyl orthoacetate will provide a compound where R$_2$ is methyl. The reaction can be run in the absence of solvent or in an inert solvent such as toluene. The reaction is run with sufficient heating to drive off any alcohol or water formed as a byproduct of the reaction.

In step (4) of Reaction Scheme I a 1H-imidazo[4,5-c]quinoline of Formula V is oxidized to provide a 1H-imidazo[4,5-c]quinoline-5N-oxide of Formula VI using a conventional oxidizing agent that is capable of forming N-oxides. Preferred reaction conditions involve reacting a solution of a compound of Formula V in chloroform with 3-chloroperoxybenzoic acid at ambient conditions.

In step (5) of Reaction Scheme I a 1H-imidazo[4,5-c]quinoline-5N-oxide of Formula VI is aminated to provide a 1H-imidazo[4,5-c]quinolin-4-amine of Formula VII which is a subgenus of Formula I. Step (5) involves (i) reacting a compound of Formula VI with an acylating agent and then (ii) reacting the product with an aminating agent. Part (i) of step (5) involves reacting an N-oxide of Formula VI with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (5) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula VI in an inert solvent such as dichloromethane, adding the aminating agent to the solution, and then slowly adding the acylating agent. The product or a pharmaceutically acceptable salt thereof can be isolated using conventional methods.

Alternatively, step (5) may be carried out by (i) reacting an N-oxide of Formula VI with an isocyanate and then (ii) hydrolyzing the resulting product. Part (i) involves reacting the N-oxide with an isocyanate wherein the isocyanato group is bonded to a carbonyl group. Preferred isocyanates include trichloroacetyl isocyanante and aroyl isocyanates such as benzoyl isocyanate. The reaction of the isocyanate with the N-oxide is carried out under substantially anhydrous conditions by adding the isocyanate to a solution of the N-oxide in an inert solvent such as chloroform or dichloromethane. Part (ii) involves hydrolysis of the product from part (i). The hydrolysis can be carried out by conventional methods such as heating in the presence of water or a lower alkanol optionally in the presence of a catalyst such as an alkali metal hydroxide or lower alkoxide.

Reaction Scheme II

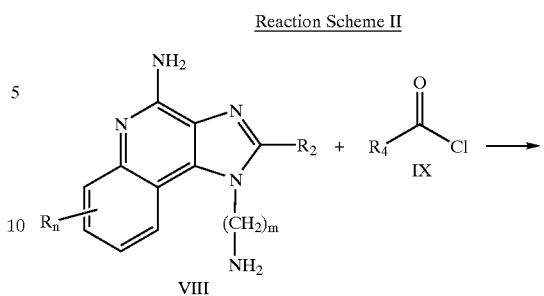

Reaction Scheme I

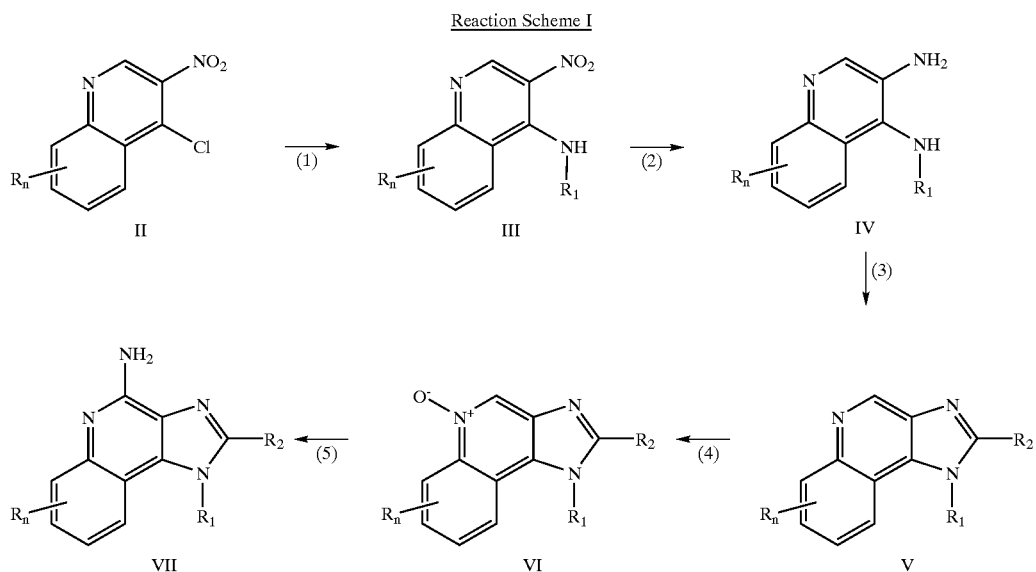

Compounds of the invention can also be prepared according to Reaction Scheme II where R, $R_2$, $R_4$ and n are as defined above and m is 1–20.

In Reaction Scheme II an aminoalkyl substituted 1H-imidazo[4,5-c]quinolin-4-amine of Formula VIII is reacted with an acid chloride of Formula IX to provide a compound of Formula X which is a subgenus of Formula I. The reaction can be carried out by adding a solution of the acid chloride in a suitable solvent such as pyridine or dichloromethane to a solution of a compound of Formula VIII either at ambient temperature or at a reduced temperature. Many 1H-imidazo[4,5-c]quinolin-4-amines of Formula VIII are known compounds, see for example U.S. Pat. No. 6,069,149 (Nanba), the disclosure of which is incorporated by reference herein; others can be readily prepared using known synthetic methods. Many acid chlorides of Formula IX are commercially available; others can be readily prepared using known synthetic methods. The product or a pharmaceutically acceptable salt thereof can be isolated using conventional methods.

-continued

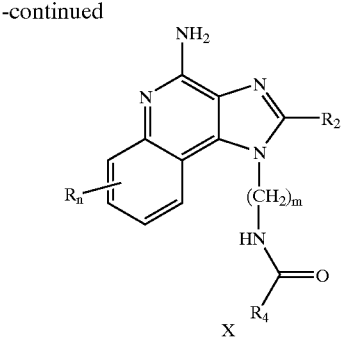

Compounds of the invention can also be prepared according to Reaction Scheme III where R, $R_2$, $R_4$ and n are as defined above and m is 1–20.

In Reaction Scheme III an aminoalkyl substituted 1H-imidazo[4,5-c]quinolin-4-amine of Formula VIII is reacted with an acid of Formula XI to provide a compound of Formula X which is a subgenus of Formula I. The reaction can be run at ambient temperature in a solvent such as

Reaction Scheme III

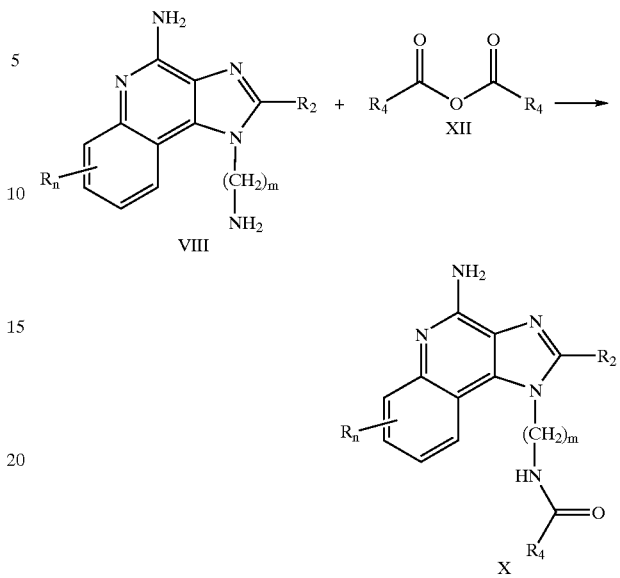

Compounds of the invention can also be prepared according to Reaction Scheme IV where R, $R_2$, $R_4$ and n are as defined above and m is 1–20.

In Reaction Scheme IV an aminoalkyl substituted 1H-imidazo[4,5-c]quinolin-4-amine of Formula VIII is reacted with an acid anhydride of Formula XII provide a compound of Formula X which is a subgenus of Formula I. The reaction can be run at ambient temperature in an inert solvent such as dichloromethane in the presence of a base such as N,N-diisopropylethylamine or pyridine. Many acid anhydrides of Formula XII are commercially available; others may be readily prepared using known synthetic methods. The product or a pharmaceutically acceptable salt thereof can be isolated using conventional methods.

dichloromethane or pyridine using a standard coupling reagent such as 1,3-dicyclohexylcarbodiimide or 1-[3-(dimethylamino)propyl]-3-ethylcarbodiimide. The product or a pharmaceutically acceptable salt thereof can be isolated using conventional methods.

Reaction Scheme IV

Tertiary amides of the invention can be prepared according to Reaction Scheme V where R, $R_2$, $R_3$, $R_4$ and n are as defined above except that $R_3$ is other than hydrogen and m is 1–20.

In step (1) of Reaction Scheme V an aminoalkyl substituted 1H-imidazo[4,5-c]quinolin-4-amine of Formula VIII is reacted with an aldehyde of Formula XIII to provide a secondary amine of Formula XIV. Preferably, the reductive amination is carried out using sodium triacetoxyborohydride. The reaction can be carried out by adding the sodium triacetoxyborohydride to a solution of the amine and the aldehyde in an inert solvent such as dichloromethane. The secondary amine or a salt thereof can be isolated using conventional methods.

In step (2) of Reaction Scheme V the secondary amine of Formula XIV is acylated to provide a compound of Formula XV which is a subgenus of Formula I. The reaction can be carried out by reacting the secondary amine of Formula XIV with an acid, acid chloride or an acid anhydride according to the methods of Reaction Schemes III, II and IV above. The product or a pharmaceutically acceptable salt thereof can be isolated using conventional methods.

Reaction Scheme V

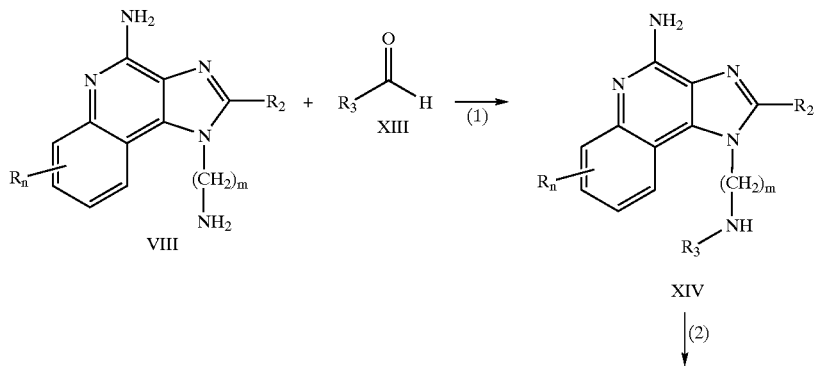

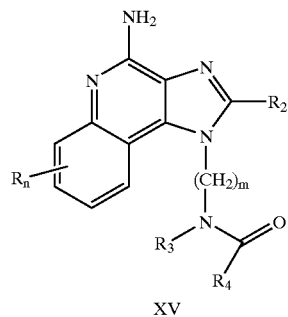

XV

Tetrahydroimidazoquinolines of the invention can be prepared according to Reaction Scheme VI where $R_2$, $R_3$ and $R_4$ are as defined above and m is 1–20.

In step (1) of Reaction Scheme VI an aminoalkyl substituted 1H-imidazo[4,5-c]quinolin-4-amine of Formula XVI is reduced to provide an aminoalkyl substituted 6,7,8,9-tetrahydro-1H-imidazo[4,5-c]quinolin-4-amine of Formula XVII. Preferably the reduction is carried out by suspending or dissolving the compound of Formula XVI in trifluoroacetic acid, adding a catalytic amount of platinum (IV) oxide, and then subjecting the mixture to hydrogen pressure. The reaction can conveniently be carried out on a Parr apparatus. The product or a salt thereof can be isolated using conventional methods.

In step (2) of Reaction Scheme VI an aminoalkyl substituted 6,7,8,9-tetrahydro-1H-imidazo[4,5-c]quinolin-4-amine of Formula XVII is reacted to provide a compound of Formula XVIII which is a subgenus of Formula I. When $R_3$ is hydrogen, the reaction can be carried out according to the methods described in Reaction Schemes II, III and IV above using a tetrahydroimidazoquinoline of Formula XVII in place of the imidazoquinoline of Formula VIII. When $R_3$ is other than hydrogen, then the reaction can be carried out using the method described in Reaction Scheme V. The product or a pharmaceutically acceptable salt thereof can be isolated using conventional methods.

Reaction Scheme VI

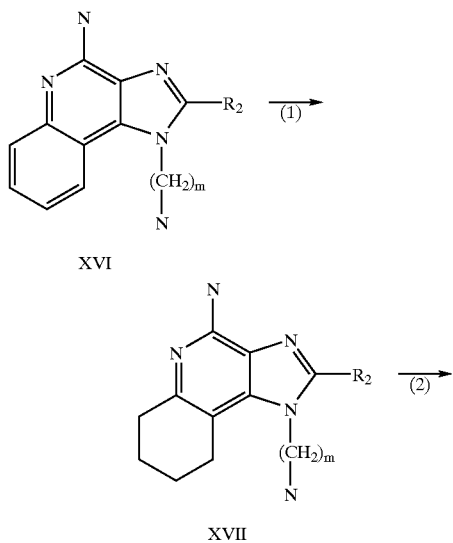

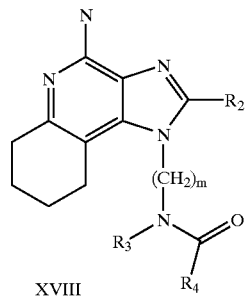

XVIII

Tetrahydroimidazoquinolines of the invention can also be prepared according to Reaction Scheme VII where R, $R_2$, $R_3$, $R_4$ and n are as defined above and m is 1–20.

In step (1) of Reaction Scheme VII a 6,7,8,9-tetrahydro-1H-imidazo[4,5-c]quinolinyl tert-butylcarbamate of Formula XIX is hydrolyzed to provide an aminoalkyl substituted 6,7,8,9-tetrahydro-1H-imidazo[4,5-c]quinolin-4-amine of Formula XX. The reaction can be carried out dissolving the compound of Formula XIX in a mixture of trifluoroacetic acid and acetonitrile and stirring at ambient temperature. Alternatively, the compound of Formula XIX can be combined with dilute hydrochloric acid and heated on a steam bath. Tetrahydro-1H-imidazo[4,5-c]quinolinyl tert-butylcarbamates of Formula XIX can be prepared using the synthetic route disclosed in U.S. Pat. No. 5,352,784 (Nikolaides). The product or a salt thereof can be isolated using conventional methods.

In step (2) of Reaction Scheme VII an aminoalkyl substituted 6,7,8,9-tetrahydro-1H-imidazo[4,5-c]quinolin-4-amine of Formula XX is reacted to provide a compound of Formula XXI which is a subgenus of Formula I. When $R_3$ is hydrogen, the reaction can be carried out according to the methods described in Reaction Schemes II, III and IV above using a tetrahydroimidazoquinoline of Formula XX in place of the imidazoquinoline of Formula VIII. When $R_3$ is other than hydrogen, then the reaction can be carried out using the method described in Reaction Scheme V. The product or a pharmaceutically acceptable salt thereof can be isolated using conventional methods.

Reaction Scheme VII

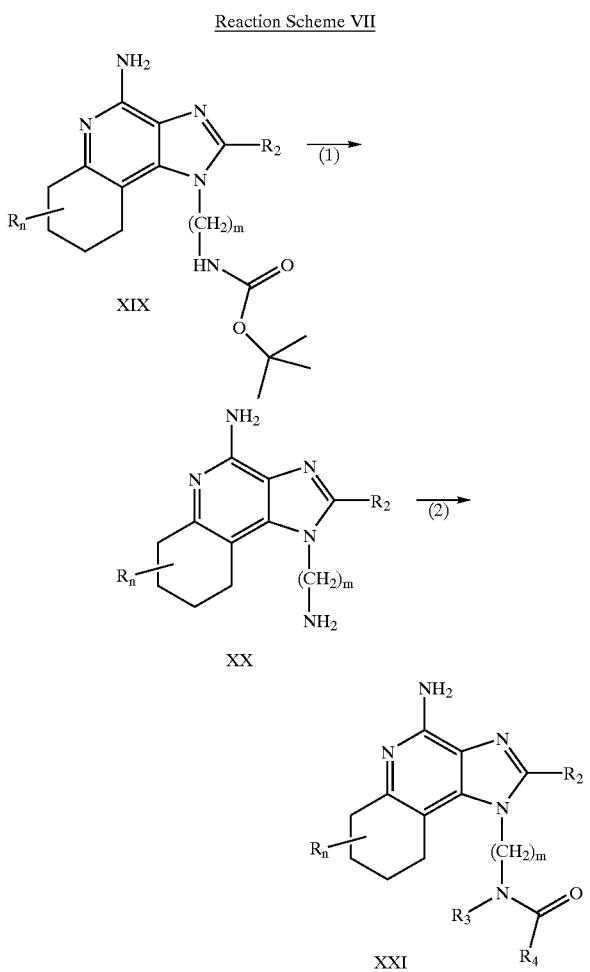

Some compounds of Formula I can be readily prepared from other compounds of Formula I. For example, compounds wherein the $R_4$ substituent contains a chloroalkyl group can be reacted with an amine to provide an $R_4$ substituent substituted by a secondary or teriary amino group; compounds wherein the $R_4$ substituent contains a nitro group can be reduced to provide a compound wherein the $R_4$ substituent contains a primary amine.

As used herein, the terms "alkyl", "alkenyl", "alkynyl" and the prefix "-alk" are inclusive of both straight chain and branched chain groups and of cyclic groups, i.e. cycloalkyl and cycloalkenyl. Unless otherwise specified, these groups contain from 1 to 20 carbon atoms, with alkenyl and alkynyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl and adamantyl.

The term "haloalkyl" is inclusive of groups that are substituted by one or more halogen atoms, including groups wherein all of the available hydrogen atoms are replaced by halogen atoms. This is also true of groups that include the prefix "haloalk-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N).

Suitable heteroaryl groups include furyl, thienyl, pyridyl, quinolinyl, isoquinolinyl, indolyl, isoindolyl, pyrrolyl, tetrazolyl, imidazo, pyrazolo, oxazolo, thiazolo and so on.

"Heterocyclyl" includes non-aromatic rings or ring systems that contain at least one ring hetero atom (e.g., O, S, N). Exemplary heterocyclic groups include pyrrolidinyl, tetrahydrofuranyl, morpholinyl, thiomorpholinyl, piperidinyl, piperazinyl, thiazolidinyl, and imidazolidinyl.

Unless otherwise specified, the terms "substituted aryl", "substituted heteroaryl" and "substituted heterocyclyl" indicate that the rings or ring systems in question are further substituted by one or more substituents independently selected from the group consisting of alkyl, alkoxy, alkylthio, hydroxy, halogen, haloalkyl, haloalkylcarbonyl, haloalkoxy (e.g., trifluoromethoxy), nitro, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, alkanoylthio, and, in the case of heterocyclyl, oxo.

In structural formulas representing compounds of the invention certain bonds are represented by dashed lines. These lines mean that the bonds represented by the dashed line can be present or absent. Accordingly, the compounds of the invention can be either imidazoquinoline compounds or tetrahydroimidazoquinoline compounds.

The invention is inclusive of the compounds described herein in any of their pharmaceutically acceptable forms, including isomers such as diastereomers and enantiomers, salts, solvates, polymorphs, and the like.

Pharmaceutical Compositions and Biological Activity

Pharmaceutical compositions of the invention contain a therapeutically effective amount of a compound of the invention as described supra in combination with a pharmaceutically acceptable carrier.

The term "a therapeutically effective amount" means an amount of the compound sufficient to induce a therapeutic effect, such as cytokine induction, antitumor activity and/or antiviral activity. Although the exact amount of active compound used in a pharmaceutical composition of the invention will vary according to factors known to those of skill in the art, such as the physical and chemical nature of the compound as well as the nature of the carrier and the intended dosing regimen, it is anticipated that the compositions of the invention will contain sufficient active ingredient to provide a dose of about 100 ng/kg to about 50 mg/kg, preferably about 10 μg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, 6, 10 and 12, and a variety of other cytokines. Among other effects, cytokines inhibit virus production and tumor cell growth, making the compounds useful in the treatment of viral diseases and tumors.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include eczema; eosinophilia; essential thrombocythaemia; leprosy; multiple sclerosis; Ommen's syndrome; discoid lupus; Bowen's disease; Bowenoid papulosis; and to enhance or stimulate the healing of wounds, including chronic wounds. Accordingly, the invention provides a method of inducing cytokine biosynthesis in an animal comprising administering an effective amount of a compound or composition of the invention to the animal.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1,6,10 and 12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

The invention is further described by the following examples, which are provided for illustration only and are not intended to be limiting in any way.

EXAMPLE 1

$N^1$-[4-(4-Amino-1H-imidazo[4,5-c]quinolin-1-yl)butyl]benzamide

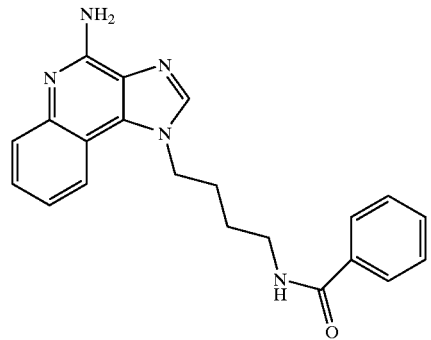

A suspension of 1-(4-aminobutyl)-1H-imidazo[4,5-c]quinolin-4-amine (2.0 g, 7.8 mmol) in pyridine (1 L) was warmed to 60° C. to dissolve the starting material. The solution was cooled to about 30° C. and then benzoyl chloride (1.1 g, 7.8 mmol) diluted with pyridine (100 mL) was slowly added. After 1 hour analysis by high performance liquid chromatography (HPLC) indicated that some starting material remained. Additional benzoyl chloride (0.3 g) was added and the reaction was warmed to 50° C. overnight. The reaction mixture was concentrated under vacuum. The resulting residue was combined with chloroform (200 mL) and 1% sodium carbonate (200 mL). The organic layer was separated and then concentrated under vacuum. The resulting residue was combined with propyl acetate (30 mL) and heated on a steam bath to dissolve the residue. The solution was allowed to cool. The resulting precipitate was isolated by filtration to provide $N^1$-[4-(4-amino-1H-imidazo[4,5-c]quinolin-1-yl)butyl]benzamide as a solid, m.p. 210–212° C. Analysis: Calculated for $C_{21}H_{21}N_5O$: %C, 70.18; %H, 5.89: %N, 19.48; Found: %C, 69.49; %H, 5.97; %N, 19.64. $^1$H NMR (500 MHz, DMSO-$d_6$) δ8.48 (t, J=6.0 Hz, 1H), 8.22 (s, 1H), 8.04 (d, J=8.0 Hz, 1H), 7.78 (d, J=8.0 Hz, 2H), 7.61 (d, J=8.0 Hz, 1H), 7.50 (t, J=8.0 Hz, 1H), 7.43 (m, 3H), 7.21 (t, J=8.0 Hz, 1H), 6.62 (broad s, 2H), 4.64 (t, J=7.0 Hz, 2H), 3.30 (q, J=6.0 Hz, 2H), 1.92 (quintet, J=7.0 Hz, 2H), 1.58 (quintet, J=7.0 Hz, 2H); MS (EI) m/e 359.1746 (359.1746 calcd for $C_{21}H_{21}N_5O$).

EXAMPLE 2

$N^1$-[4-(4-Amino-1H-imidazo[4,5-c]quinolin-1-yl)butyl]benzamide Hydrochloride Hydrate $N^1$-[4-(4-Amino-1H-imidazo[4,5-c]quinolin-1-yl)butyl]benzamide (1 g) was dissolved in isopropanol. Hydrochloric acid (1 eq of 12N) was added. The resulting precipitate was isolated by filtration to provide 1 g of $N^1$-[4-(4-amino-1H-imidazo[4,5-c]quinolin-1-yl)butyl]benzamide hydrochloride hydrate as a solid, m.p. 254–256° C. Analysis: Calculated for $C_{21}H_{21}N_5O\cdot HCl\cdot 1.5\ H_2O$: %C, 59.63; %H, 5.96; %N, 16.56; Found: %C 59.61; %H, 6.04; %N, 16.64. $^1$H NMR (500 MHz, DMSO-$d_6$) δ13.80 (broad s, 1H), 9.15 (broad s, 2H), 8.56 (s, 1H), 8.50 (t, J=6.0 Hz, 1H), 8.23 (d, J=8.0 Hz, 1H), 7.83 (d, J=8.0 Hz, 1H), 7.76 (d, J=8.0 Hz, 2H), 7.71 (t, J=8.0 Hz, 1H), 7.53 (t, J=8.0 Hz, 1H), 7.50 (t, J=8.0 Hz, 1H), 7.42 (t, J=8.0 Hz, 2H), 4.72 (t, J=7.0 Hz, 2H), 3.30 (q, J=7.0 Hz, 2H), 1.93 (quintet, J=7.0 Hz, 2H), 1.61 (quintet, J=7.0 Hz, 2H).

EXAMPLE 3

$N^1$-[4-(4-Amino-2-propyl-1H-imidazo[4,5-c]quinolin-1-yl)butyl]benzamide

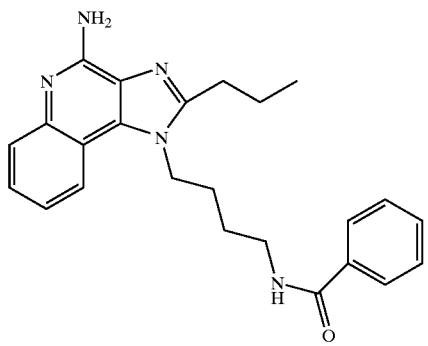

Using the general method of Example 1, 1-(4-aminobutyl)-2-propyl-1H-imidazo[4,5-c]quinolin-4-amine (0.55 g, 1.8 mmol) was reacted with benzoyl chloride (0.26 g, 1.8 mmol) to provide $N^1$-[4-(4-amino-2-propyl-1H-imidazo[4,5-c]quinolin-1-yl)butyl]benzamide as a solid, m.p. 173–174° C. $^1$H NMR (500 MHz, DMSO-$d_6$) δ8.80 (broad s, 2H), 8.46 (t, J=6.0 Hz, 1H), 8.20 (d, J=8.0 Hz, 1H), 7.81 (d, J=8.4 Hz, 1H), 7.76 (d, J=7.4 Hz, 2H), 7.67 (t, J=7.4 Hz, 1H), 7.49 (m, 2H), 7.43 (t, J=7.5 Hz, 2H), 4.63 (t, J=7.0 Hz, 2H), 3.34 (m, 2H), 2.97 (t, J=7.0 Hz, 2H), 1.85 (m, 4H), 1.72 (quintet, J=7.0 Hz, 2H), 1.01 (t, J=7.0 Hz, 3H); MS (EI) m/e 401.2210 (401.2216 calcd for $C_{24}H_{27}N_5O$)

EXAMPLE 4

$N^1$-[4-(4-Amino-2-methyl-1H-imidazo[4,5-c]quinolin-1-yl)butyl]benzamide

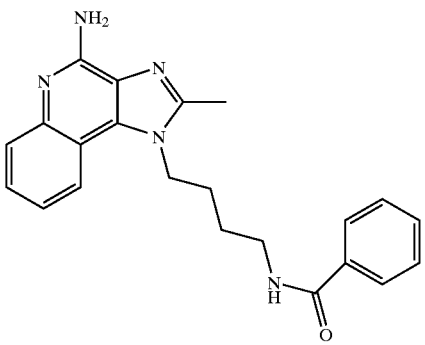

Using the general method of Example 1, 1-(4-aminobutyl)-2-methyl-1H-imidazo[4,5-c]quinolin-4-amine (0.5 g, 1.8 mmol) was reacted with benzoyl chloride (0.26 g, 1.8mmol) to provide $N^1$-[4-(4-amino-2-methyl-1H-imidazo[4,5-c]quinolin-1-yl)butyl]benzamide as a solid, m.p. 164–170° C. $^1$H NMR (500 MHz, DMSO-$d_6$) δ8.47 (t, J=6.0 Hz, 1H), 8.01 (d, J=8.0 Hz, 1H), 7.78 (d, J=8.0 Hz, 2H), 7.59 (dd, J=8.0, 1.2 Hz, 1H), 7.50 (t, J=8.0 Hz, 1H), 7.43 (t, J=8.0 Hz, 2H), 7.38 (dt, J=8.0, 1.2 Hz, 1H), 7.17 (dt, J=8.0, 1.2 Hz, 1H), 6.48 (broad s, 2H), 4.53 (t, J=7.0 Hz, 2H), 3.31 (q, J=6.0 Hz, 2H), 2.60 (s, 3H), 1.88 (quintet, J=7.0 Hz, 2H), 1.68 (quintet, J=7.0 Hz, 2H); MS (EI) m/e 373.1903 (373.1903 calcd for $C_{22}H_{23}N_5O$)

EXAMPLE 5

$N^1$-[4-(4-Amino-2-ethyl-1H-imidazo[4,5-c]quinolin-1-yl)butyl]benzamide

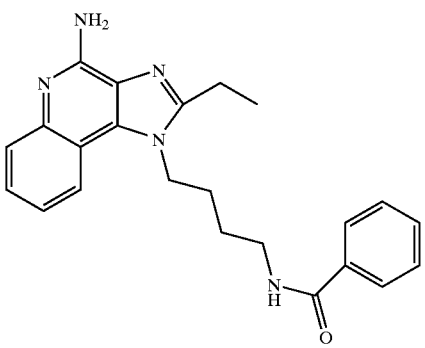

Using the general method of Example 1, 1-(4-aminobutyl)-2-ethyl-1H-imidazo[4,5-c]quinolin-4-amine (0.5 g, 1.76 mmol) was reacted with benzoyl chloride (0.25 g, 1.76 mmol) to provide $N^1$-[4-(4-amino-2-ethyl-1H-imidazo[4,5-c]quinolin-1-yl)butyl]benzamide as a solid, m.p. 203–206° C. $^1$H NMR (500 MHz, DMSO-$d_6$) δ8.48 (t, J=6.0 Hz, 1H), 8.00 (d, J=8.0 Hz, 1H), 7.79 (d, J=8.0 Hz, 2H), 7.60 (dd, J=8.0, 1.0 Hz, 1H), 7.50 (t, J=8.0 Hz, 1H), 7.43 (t, J=8.0 Hz, 2H), 7.38 (t, J=8.0 Hz, 1H), 7.17 (t, J=8.0 Hz, 1H), 6.47 (broad s, 2H), 4.53 (t, J=7.0 Hz, 2H), 3.32 (q, J=6.0 Hz, 2H), 2.95 (q, J=7.0 Hz, 2H), 1.87 (quintet, J=7.0 Hz, 2H), 1.70 (quintet, J=7.0 Hz, 2H), 1.35 (t, J=7.0 Hz, 3H); MS (EI) m/e 387.2058 (387.2059 calcd for $C_{23}H_{25}N_5O$).

EXAMPLE 6

N$^1$-[4-(4-Amino-2-butyl-1H-imidazo[4,5-c]quinolin-1-yl)butyl]benzamide

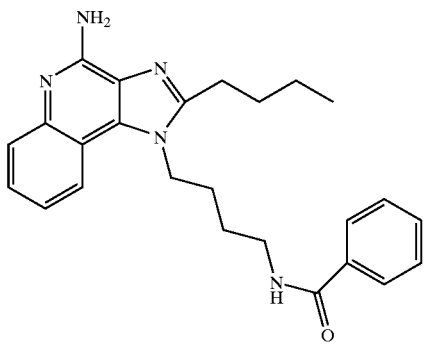

1-(4-Aminobutyl)-2-butyl-1H-imidazo[4,5-c]quinolin-4-amine (0.5 g, 1.6 mmol) was combined with pyridine (50 mL) and heated to 50° C. Benzoyl chloride (0.22 g, 1.6 mmol) was added via a pipette. After 1 hour analysis by HPLC indicated that all of the starting material was gone and that several products had formed. The reaction mixture was concentrated under vacuum. The residue was combined with dichloromethane and aqueous sodium bicarbonate. The organic layer was separated and then concentrated under vacuum. The residue was dissolved in dichloromethane and placed on a silica gel column. The column was eluted with 5% methanol in dichloromethane and then with 10% methanol in dichloromethane. The 10% methanol in dichloromethane fractions were combined and concentrated under vacuum to provide N$^1$-[4-(4-amino-2-butyl-1H-imidazo[4,5-c]quinolin-1-yl)butyl]benzamide as a solid, m.p. 174–175° C. $^1$H NMR (500 MHz, DMSO-d$_6$) δ8.48 (t, J=6.0 Hz, 1H), 8.00 (d, J=8.0 Hz, 1H), 7.78 (d, J=8.0 Hz, 2H), 7.60 (d, J=8.0 Hz, 1H), 7.50 (t, J=8.0 Hz, 1H), 7.43 (t, J=8.0 Hz, 2H), 7.39 (t, J=8.0 Hz, 1H), 7.18 (t, J=8.0 Hz, 1H), 6.50 (broad s, 2H), 4.54 (t, J=7.0 Hz, 2H), 3.32 (m, 2H), 2.91 (t, J=7.0 Hz, 2H), 1.86 (quintet, J=7.0 Hz, 2H), 1.77 (quintet, J=7.0 Hz, 2H), 1.70 (quintet, J=7.0 Hz, 2H), 1.41 (sextet, J=7.0 Hz, 2H), 0.91 (t, J=7.0 Hz, 3H); MS (CI) m/e 416 (M+H).

EXAMPLE 7

N$^1$-[4-(4-Amino-1H-imidazo[4,5-c]quinolin-1-yl)butyl]-4-(chloromethyl)benzamide

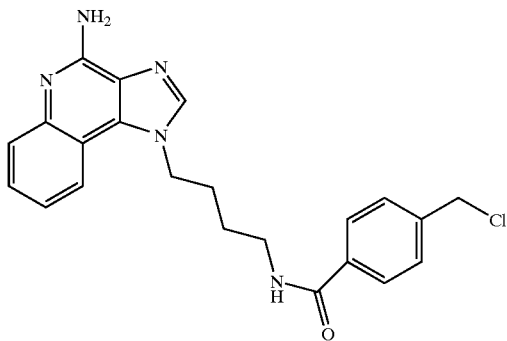

Part A

Oxalyl chloride (4.4 mL of 2M in chloroform, 8.8 mmol) was added to a suspension of 4-(chloromethyl)benzoic acid (1 g, 5.7 mmol) in dichloromethane. N,N-dimethylformamide (4 drops) was added to catalyze the reaction. After 1 hour analysis by HPLC indicated 100% clean conversion. The reaction mixture was concentrated under vacuum to provide 4-(chloromethyl)benzoyl chloride.

Part B

A solution of 4-(chloromethyl)benzoyl chloride (1.06 g, 5.6 mmol) in dichloromethane was added to a suspension of 1-(4-aminobutyl)-1H-imidazo[4,5-c]quinolin-4-amine (1.0 g, 3.9 mmol) in pyridine (250 mL). After 1 hour HPLC analysis indicated that the reaction was complete. The reaction mixture was concentrated under vacuum. The residue was combined with saturated aqueous sodium bicarbonate. A solid was isolated by filtration then dissolved in chloroform containing a small amount of methanol. The solution was washed with saturated aqueous sodium bicarbonate. The organic layer was concentrated under vacuum. The resulting residue was purified by column chromatography (silica gel eluting with 10% methanol in dichloromethane) to provide N$^1$-[4-(4-amino-1H-imidazo[4,5-c]quinolin-1-yl)butyl]-4-(chloromethyl)benzamide as a solid, m.p. 240–300 (dec.). $^1$H NMR (500 MHz, DMSO-d$_6$) δ8.49 (t, J=6.0 Hz, 1H), 8.21 (s, 1H), 8.03 (d, J=8.0 Hz, 1H), 7.76 (d, J=8.0 Hz, 2H), 7.61 (d, J=8.0 Hz, 1H), 7.46 (d, J=8.0 Hz, 2H), 7.42 (t, J=8.0 Hz, 1H), 7.20 (t, J=8.0 Hz, 1H), 6.80 (broad s, 2H), 4.78 (s, 2H), 4.62 (t, J=7.0 Hz, 2H), 3.28 (q, J=6.0 Hz, 2H), 1.89 (quintet, J=7.0 Hz, 2H), 1.56 (quintet, J=7.0 Hz, 2H); MS (CI) m/e 408 (M+H).

EXAMPLE 8

N$^1$-[4-(4-Amino-1H-imidazo[4,5-c]quinolin-1-yl)butyl]-4-[(2-tetrahydro-1H-1-pyrrolyl-1H-benzo[d]imidazol-1-yl)methyl]benzamide

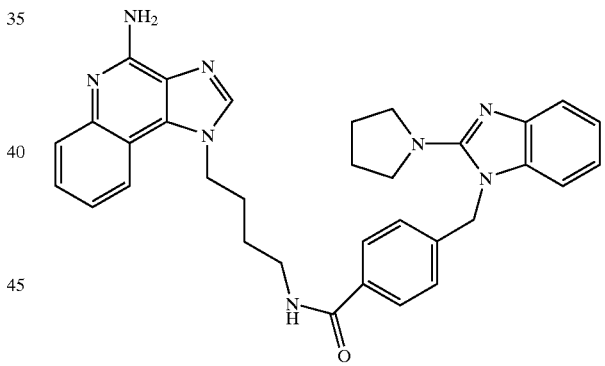

Part A

2-Hydroxy-1H-benzimidazole (62 g, 0.46 mole) was added to phosphorous oxychloride (200 mL) and the mixture was refluxed for 4.5 hours. The resulting solution was poured over 4 L of ice and the mixture was made strongly basic with ammonium hydroxide. The resulting solid was isolated by filtration, washed with water and dried to provide crude 2-chloro-1H-benzimidazole.

Part B

2-Chloro-1H-benzimidazole (10.0 g, 0.066 mol), pyrrolidine (18.5 g, 0.26 mol), and ethanol (100 mL) were combined. The resulting solution was heated at 160–170° C. for 6 hours and then the solvent was evaporated. The resulting residue was mixed with water. The mixture was made strongly acidic with hydrochloric acid and then made basic with ammonium hydroxide. The resulting solid was isolated by filtration, washed with water and then air dried to provide 11.8 g of crude product as a tan powder. This material was recrystallized from ethyl acetate/methanol to provide 4.9 g of 2-pyrrolidino-1H-benzimidazole. Analysis: Calculated for $C_{11}H_{13}N_3$: %C, 70.56; %H, 7.00; %N, 22.44; Found: %C, 70.13; %H, 7.05; %N, 22.70.

Part C

Sodium hydride (402 mg, 11 mmol) was added to a suspension of 2-pyrrolidino-1H-benzimidazole (1.9 g, 10.1 mmol) in dry N,N-dimethylformamide (30 mL). All solids dissolved. The solution was allowed to stir at ambient temperature for 15 minutes following the cessation of foaming. The solution was cooled to 5° C. and a solid formed. Methyl 4-(bromomethyl)benzoate (2.1 g, 01 mol) was added to the suspension and all the solids dissolved. The solution was allowed to stir at ambient temperature and a solid formed. The mixture was stirred at ambient temperature overnight and then it was poured into cold water. A solid was isolated by filtration, washed with water and dried to provide 3.0 g of crude product as an off-white solid. This material was recrystallized from methanol to provide methyl 4-[(2-pyrrolidinyl-1H-benzimidazol-1yl)methyl]benzoate. Analysis: Calculated for $C_{20}H_{21}N_3O_2$: %C, 71.62; %H, 6.31; %N, 12.53; Found: %C, 71.44; %H, 6.41; %N, 12.50.

Part D

Methyl 4-[(2-pyrrolidinyl-1H-benzimidazol-1yl)methyl] benzoate (2.5 g, 7.5 mmol) was added to a solution of sodium hydroxide (1.8 g, 45 mmol) in water (30 mL) and methanol (10 mL). The mixture was heated on a steam bath until all of the ester dissolved. Heating was continued for an additional 15 minutes and then the solution was diluted with an equal volume of water and neutralized with hydrochloric acid. The resulting precipitate was isolated by filtration, washed with water and dried to provide 1.9 g of crude product. This material was recrystallized from N,N-dimethylformamide to provide 4-[(2-pyrrolidinyl-1H-benzimidazol-1yl)methyl]benzoic acid. Analysis: Calculated for $C_{19}H_{19}N_3O_2$: %C, 71.01; %H, 5.96; %N, 13.07; Found: %C, 70.01; %H, 6.14; %N, 13.32.

Part E

Oxalyl chloride (4 mL) was added to a suspension of 4-[(2-pyrrolidinyl-1H-benzimidazol-1yl)methyl]benzoic acid (0.28 g, 0.872 mmol) in chloroform (50 mL). The mixture was heated at reflux for 1 hour and then concentrated under vacuum. The residue was diluted with toluene, concentrated under vacuum and then dried under vacuum at ambient temperature over the weekend to provide crude 4-[(2-pyrrolidinyl-1H-benzimidazol-1yl)methyl]benzoyl chloride.

Part F 1-(4-Aminobutyl)-1H-imidazo[4,5-c]quinolin-4-amine (0.20 g, 0.783 mmol) was added to a mixture of the acid chloride from Part E and pyridine (20 mL). After 10 minutes analysis by HPLC indicated that the reaction mixture contained product plus about 10% each of the acid chloride and the amine. The reaction mixture was concentrated under vacuum. The residue was combined with water, treated with 0.1 N sodium hydroxide and then extracted with dichloromethane. The dichloromethane extract was purified by column chromatography (silica gel eluting with 5–10% methanol in dichloromethane) to provide $N^1$-[4-(4-amino-1H-imidazo[4,5-c]quinolin-1-yl)butyl]-4-[(2-tetrahydro-1H-1-pyrrolyl-1H-benzo[d]imidazol-1-yl)methyl] benzamide as a solid, m.p. 150–153° C. MS (EI) m/e 558.2865 (558.2855 calcd for $C_{33}H_{34}N_8O$).

EXAMPLE 9

$N^1$-[5-(4-Amino-2-methyl-1H-imidazo[4,5-c] quinolin-1-yl)pentyl]benzamide

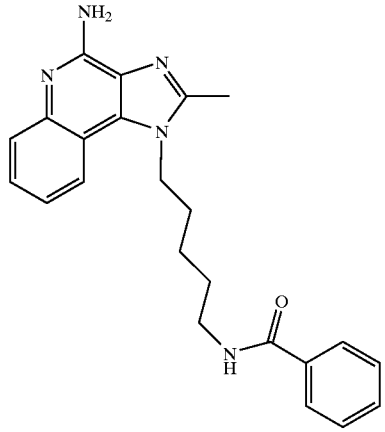

Part A

Under an argon atmosphere, 1,5-diaminopentane (25 g, 0.24 mol) and benzamide (9.9 g, 0.081 mol) were combined and heated at reflux overnight. The reaction mixture was concentrated under vacuum to remove the excess diamine. The residue was distilled at about 210° C. at 12 torr ($16 \times 10^2$ pascals) to provide 11.8 g of N-(5-aminopentyl)benzamide as a colorless oil.

Part B

Triethylamine (1 eq.) was added to a suspension of 4-chloro-3-nitroquinoline hydrochloride (13 g, 53 mmol) in chloroform. A suspension of N-(5-aminopentyl)benzamide (11 g, 53 mmol) in chloroform was added and the reaction mixture was heated to reflux. Progress of the reaction was monitored by HPLC. The reaction mixture was concentrated under vacuum. The residue was diluted with toluene, heated to reflux and then filtered while still hot. The filtrate was allowed to cool. The resulting precipitate was isolated by filtration to provide 16.9 g of $N^1$-{5-[(3-nitroquinolin-4-yl) amino]pentyl}benzamide as a yellow solid, m.p. 130–132° C. $^1$H NMR (500 MHz, DMSO-$d_6$) δ9.07 (s, 1H), 9.02 (broad s, 1H), 8.53 (d, J=8.0 Hz, 1H), 8.43 (t, J=6.0 Hz, 1H), 7.89 (dd, J=8.0, 1.2 Hz, 1H), 7.83 (dt, J=8.0, 1.2 Hz, 1H), 7.80 (d, J=8.0 Hz, 2H), 7.57 (dt, J=8.0, 1.2 Hz, 1H), 7.50 (t, J=8.0 Hz, 1H), 7.43 (t, J=8.0 Hz, 2H), 3.63 (q, J=6.0 Hz, 2H), 3.25 (q, J=6.0 Hz, 2H), 1.77 (quintet, J=7.0 Hz, 2H), 1.55 (quintet, J=7.0 Hz, 2H), 1.39 (quintet, J=7.0 Hz, 2H).

Part C

A catalytic amount of platinum on carbon was added to a suspension of $N^1$-{5-[(3-nitroquinolin-4-yl)amino] pentyl}benzamide (3.4 g, 9 mmol) in isopropyl alcohol (250 mL). The reaction mixture was placed under a hydrogen atmosphere at 50 psi ($3.4 \times 10^4$ pascals) on a Parr apparatus. After 2 hours the reaction mixture was filtered to remove the catalyst. The filtrate was concentrated under vacuum to provide crude $N^1$-{5-[(3-aminoquinolin-4-yl)amino] pentyl}benzamide. This material was combined with triethylorthoacetate (1.4 g, 9 mmol) and toluene (200 mL). The reaction mixture was heated overnight on a steam bath with a Vigreux column. The toluene was decanted from the reaction mixture and concentrated under vacuum to provide $N^1$-[5-(2-methyl-1H-imidazo[4,5-c]quinolin-1-yl)pentyl] benzamide as an oil.

Part D

3-Chloroperoxybenzoic acid (3 g, 9 mmol) was added to a solution of the oil from Part C in methyl acetate (50 mL).

The reaction mixture was stirred at ambient temperature overnight and then diluted with diethyl ether (50 mL). The resulting precipitate was isolated by filtration and then washed with diethyl ether to provide 1.6 g of 1-(5-benzamidopentyl)-2-methyl-1H-imidazo[4,5-c]quinoline-5N-oxide.

Part E

Ammonium hydroxide (50 mL) was added to a solution of 1-(5-benzamidopentyl)-2-methyl-1H-imidazo[4,5-c]quinoline-5N-oxide (1.6 g, 4.12 mmol) in dichloromethane (150 mL). Tosyl chloride (0.78 g, 4.12 mmol) was slowly added with rapid stirring of the reaction mixture. After 1 hour the organic layer was separated, washed with 1% sodium carbonate and then concentrated under vacuum. The resulting residue was combined with 1N hydrochloric acid (30 mL), treated with charcoal and then filtered. The filtrate was neutralized. An oil precipitated out. The oil solidified overnight to provide 0.63 g of $N^1$-[5-(4-amino-2-methyl-1H-imidazo[4,5-c]quinolin-1-yl)pentyl]benzamide as a solid, m.p. 110–120° C. $^1$H NMR (500 MHz, DMSO-$d_6$) δ8.50 (t, J=5.5 Hz, 1H), 8.12(d, J=8.0 Hz, 1H), 7.82 (d, J=8.5 Hz, 2H), 7.71 (d, J=8.5 Hz, 1H), 7.63 (broad s, 2H), 7.55 (t, J=8.5 Hz, 1H), 7.51 (t, J=8.3 Hz, 1H), 7.46 (t, J=8.0 Hz, 2H), 7.40 (t, J=8.0 Hz, 1H), 4.52 (t, J=7.5 Hz, 2H), 3.28 (q, J=6.0 Hz, 2H), 2.64 (s, 3H), 1.87 (quintet, J=7.0 Hz, 2H), 1.79 (quintet, J=7.0 Hz, 2H), 1.48(quintet, J=7.0 Hz, 2H); MS (CI) m/e 388 (M+H).

EXAMPLE 10

$N^1$-[5-(4-Amino-1H-imidazo[4,5-c]quinolin-1-yl)pentyl]benzamide Hydrochloride

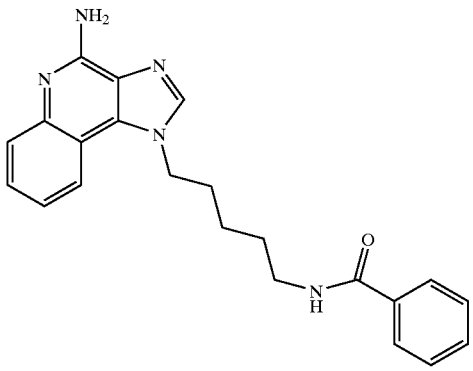

Part A

A catalytic amount of platinum on carbon was added to a suspension of $N^1$-{5-[(3-nitroquinolin-4-yl)amino]pentyl}benzamide (5 g, 13.2 mmol) in toluene (250 mL). The reaction mixture was placed under a hydrogen atmosphere at 50 psi (3.4×10$^4$ pascals) on a Parr apparatus. After about 2 hours an oily ball had formed in the bottom of the Parr bottle. Magnesium sulfate and additional catalyst were added and the hydrogenation was continued overnight. The reaction mixture was filtered to remove the catalyst. The residue in the Parr bottle was combined with isopropyl alcohol (150 mL), heated on a steam bath and then filtered. HPLC analysis indicated that both filtrates contained product so they were combined and concentrated under vacuum to provide crude $N^1$-{5-[(3-aminoquinolin-4-yl)amino]pentyl}benzamide. This material was combined with toluene (250 mL). Triethylorthoformate (4 g, 26.4 mmol) was added and the reaction mixture was heated at reflux with a Vigreux column for 2 hours. The reaction mixture was allowed to cool to ambient temperature. The resulting precipitate was isolated by filtration to provide 3.4 g of $N^1$-[5-(1H-imidazo[4,5-c]quinolin-1-yl)pentyl]benzamide as a solid, m.p. 171.5–172.5° C. $^1$H NMR (500 MHz, DMSO-$d_6$) δ9.22 (s, 1H), 8.43 (t, J=6.0 Hz, 2H), 8.38 (m, 1H), 8.18 (m, 1H), 7.80 (d, J=7.0 Hz, 2H), 7.73 (m, 2H), 7.51 (t, J=7.0 Hz, 1H), 7.45 (t, J=7.0 Hz, 2H), 4.72 (t, J=7.5 Hz, 2H), 3.25 (q, J=6.0 Hz, 2H), 1.94 (quintet, J=7.5 Hz, 2H), 1.58 (quintet, J=7.5 Hz, 2H), 1.40 (quintet, J=8.5 Hz, 2H).

Part B

3-Chloroperoxybenzoic acid (1.9 g, 5.58 mmol) was added to a solution of $N^1$-[5-(1H-inmidazo[4,5-c]quinolin-1-yl)pentyl]benzamide (2.0 g, 5.58 mmol) in chloroform. After 4 hours HPLC analysis indicated that the reaction was complete. The reaction was washed twice with 1% sodium carbonate (50 mL) and then concentrated under vacuum to provide 1-(5-benzamidopentyl)-1H-imidazo[4,5-c]quinoline-5N-oxide.

Part C

Ammonium hydroxide was added to a solution of 1-(5-benzamidopentyl)-1H-imidazo[4,5-c]quinoline-5N-oxide (2.1 g, 5.58 mmol) in dichloromethane. Tosyl chloride (1.06 g, 5.58 mmol) was slowly added with rapid stirring of the reaction mixture. After 1 hour the reaction was diluted with dichloromethane. The organic layer was separated, washed with 1% sodium carbonate and then concentrated under vacuum. The resulting residue was dissolved in isopropyl alcohol (100 mL) and then 6N hydrochloric acid (0.93 mL) was added. The resulting precipitate was suspended in water (150 mL), heated to reflux, treated with charcoal and then filtered. The filtrate was allowed to cool. The resulting precipitate was isolated by filtration and dried to provide 0.9 g of $N^1$-[5-(4-amino-1H-imidazo[4,5-c]quinolin-1-yl)pentyl]benzamide hydrochloride as a white crystalline solid, m.p. 217–219° C. Analysis: Calculated for $C_{22}H_{23}N_5O·HCl·1/2H_2O$: %C, 52.85; %H, 6.85; %N, 14.01; Found: %C, 52.62; %H, 6.44%; %N, 13.87. $^1$H NMR (500 MHz, DMSO-$d_6$) δ13.84 (broad s, 1H), 9.24 (broad s, 2H), 8.51 (s, 1H), 8.43 (t, J=6.0 Hz, 1H), 8.22 (d, J=8.0 Hz, 1H), 7.82 (d, J=8.0 Hz, 1H), 7.76 (d, J=8.0 Hz, 2H), 7.70 (t, J=8.0 Hz, 1H), 7.56 (t, J=8.0 Hz, 1H), 7.49 (t, J=8.0 Hz, 1H), 7.42 (t, J=8.0 Hz, 2H), 4.66 (t, J=7.0 Hz, 2H), 3.23 (q, J=6.0 Hz, 2H), 1.90 (quintet, J=7.0 Hz, 2H), 1.56 (quintet, J=7.0 Hz, 2H), 1.38 (quintet, J=7.0 Hz, 2H); MS (CI) m/e 374 (M+H).

EXAMPLE 11

$N^1$-[3-(4-Amino-1H-imidazo[4,5-c]quinolin-1-yl)propyl]benzamide Hydrochloride

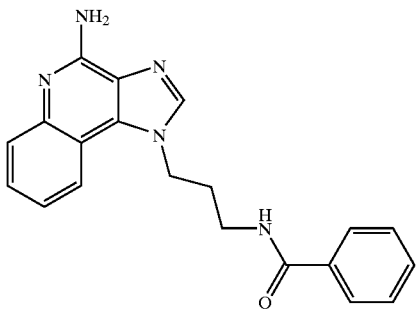

Part A

Benzamide (25 g, 0.20 mol) and 1,3-diaminopropane (45.9 g, 0.60 mol) were combined in a Parr vessel and heated to 150° C. for 15 hours. The vessel was cooled and the reaction mixture was concentrated under vacuum to remove excess diamine. The residue was dissolved in water (500 mL) and concentrated hydrochloric acid was added to adjust the pH to <1. The resulting precipitate (starting benzamide and diacylated product) was removed by filtration. The filtrate was washed with dichloromethane. The aqueous layer was made strongly basic by the addition of 50% sodium hydroxide and then it was extracted with dichloromethane (4×300 mL). The extracts were combined, washed with brine (300 mL), dried over sodium sulfate and then concentrated under vacuum to provide 11.9 g of N-(3-aminopropyl)benzamide as an oil.

Part B

Triethylamine (9.3 mL, 67 mmol) was added to a mixture of 4-chloro-3-nitroquinoline hydrochloride (16.4 g, 67 mmol) and dichloromethane (400 mL). A solution of N-(3-aminopropyl)benzamide (11.9 g, 67 mmol) in dichloromethane (100 mL) was added all a once. The reaction mixture was stirred at ambient temperature for 1 hour and then heated on a steam bath for 1 hour. The resulting precipitate was isolated by filtration to provide 6 g of $N^1$-{3-[(3-nitroquinolin-4-yl)amino]propyl}benzamide as a yellow solid, m.p. 209–211° C. $^1$H NMR (500 MHz, DMSO-$d_6$) δ9.07 (broad s, 1H), 9.05 (s, 1H), 8.54 (t, J=6.0 Hz, 1H), 8.51 (d, J=8.0 Hz, 1H), 7.89 (d, J=8.0 Hz, 1H), 7.82 (t, J=8.0 Hz, 1H), 7.76 (d, J=8.0 Hz, 2H), 7.55 (t, J=8.0 Hz, 1H), 7.50 (t, J=8.0 Hz, 1H), 7.43 (t, J=8.0 Hz, 2H), 3.69 (q, J=6.0 Hz, 2H), 3.35 (q, J=6.0 Hz, 2H), 2.00 (quintet, J=7.0 Hz, 2H).

Part C

A suspension of $N^1$-{3-[(3-nitroquinolin-4-yl)amino]propyl}benzamide (1.0 g, 2.8 mmol) in isopropyl alcohol (120 mL) was warmed to dissolve some of the material. A catalytic amount of platinum on carbon was added and the reaction mixture was placed under a hydrogen atmosphere at 50 psi (3.4×10$^4$ pascals) on a Parr apparatus. After 3 hours the reaction mixture was filtered to remove catalyst. The filtrate was concentrated under vacuum to provide crude $N^1$-{3-[(3-aminoquinolin-4-yl)amino]propyl}benzamide as an oil. Toluene (100 mL) was added to the oil followed by the addition of triethylorthoformate (0.8 g, 5.6 mmol). The reaction mixture was heated on a steam bath overnight. The reaction mixture was allowed to cool to ambient temperature. The resulting precipitate was isolated by filtration to provide 0.53 g of $N^1$-[3-(1H-imidazo[4,5-c]quinolin-1-yl)propyl]benzamide as an off white solid, m.p. 188–190° C. $^1$H NMR (500 MHz, DMSO-$d_6$) δ8.67 (t, J=5.5 Hz, 1H), 8.50 (s, 1H), 8.37 (d, J=7.5 Hz, 1H), 8.17 (dd, J=8.0, 1.5 Hz, 1H), 7.87 (d, J=7.0 Hz, 2H), 7.71 (dt, J=7.5, 1.5 Hz, 1H), 7.56 (dt, J=7.5, 1.0 Hz, 1H), 7.54 (d, J=8.0 Hz, 2H), 7.48 (t, J=7.0 Hz, 2H), 4.78 (t, J=7.0 Hz, 2H), 3.38 (q, J=6.0 Hz, 2H), 2.18 (quintet, J=7.0 Hz, 2H).

Part D

3-Chloroperoxybenzoic acid (0.55 g, 1.6 mmol) was slowly added at ambient temperature to a solution of $N^1$-[3-(1H-imidazo[4,5-c]quinolin-1-yl)propyl]benzamide (0.53 g, 1.6 mmol) in chloroform (50 mL). After 3 hours the reaction was washed with 1% sodium carbonate (2×30 mL) and then concentrated under vacuum to provide 0.32 g of 1-(3-benzamidopropyl)-1H-imidazo[4,5-c]quinoline-5N-oxide as a solid.

Part E

Ammonium hydroxide (20 mL) was added to a solution of 1-(3-benzamidopropyl)-1H-imidazo[4,5-c]quinoline-5N-oxide (0.32 g, 0.92 mmol) in dichloromethane (100 mL). Tosyl chloride (0.17 g, 0.92 mmol) was slowly added. The reaction mixture was stirred overnight at ambient temperature and then it was concentrated under vacuum to remove the dichloromethane. The resulting precipitate was isolated by filtration and then washed with water. This material was dissolved in isopropyl alcohol (20 mL/g). Concentrated hydrochloric acid (1 eq.) was added and then the volume of the reaction mixture was reduced by 10–20%. The resulting precipitate was isolated by filtration and washed with isopropyl alcohol to provide 0.25 g of $N^1$-[3-(4-amino-1H-imidazo[4,5-c]quinolin-1-yl)propyl]benzamide hydrochloride as a solid, m.p. 265–270° C. Analysis: Calculated for $C_{20}H_{19}N_5O \cdot HCl \cdot 1/2H_2O$: %C, 61.46; %H, 5.42; %N, 17.92; Found: %C, 61.79; %H, 5.34; %N, 17.61. $^1$H NMR (500 MHz, DMSO-$d_6$) δ13.74 (broad s, 1H), 9.30 (broad s, 2H), 8.73 (t, J=6.0 Hz, 1H), 8.61 (s, 1H), 8.22 (d, J=8.0 Hz, 1H), 7.87 (d, J=8.0 Hz, 2H), 7.84 (d, J=8.0 Hz, 1H), 7.71 (t, J=8.0 Hz, 1H), 7.54 (t, J=8.0 Hz, 1H), 7.48 (t, J=8.0 Hz, 2H), 7.43 (t, J=8.0 Hz, 1H), 4.75 (t, J=7.0 Hz, 2H), 3.39 (q, J=6.0 Hz, 2H), 217 (t, J=7.0 Hz, 2H); MS (EI) m/e 345.1593 (345.1590 calcd for $C_{20}H_{19}N_5O$).

EXAMPLE 12

$N^3$-[4-(4-Amino-1H-imidazo[4,5-c]quinolin-1-yl)butyl]-6-morpholinonicotinamide

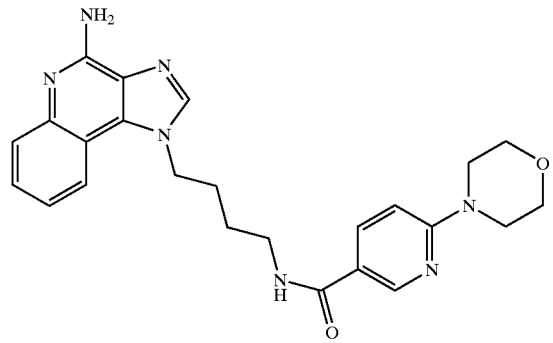

Part A

Carbonyl diimidazole (18.6 g, 0.115 mol) was added to a suspension of 6-chloronicotinic acid (16.6 g, 0.105 mol) in dichloromethane (250 mL). After all of the solid had dissolved the reaction solution was stirred at ambient temperature for 1 hour and then isopropyl alcohol (100 mL) was added. The dichloromethane was removed under vacuum. A catalytic amount of sodium isopropoxide was added to the solution and the solution was heated at reflux for 1 hour. The solution was then concentrated under vacuum. The resulting residue was slurried with water and then extracted with diethyl ether. The extract was dried over magnesium sulfate and then concentrated under vacuum to provide 23.9 g of isopropyl 6-chloronicotinate.

Part B

A solution of isopropyl 6-chloronicotinate (6.0 g, 0.03 mol) and morpholine (13 mL, 0.15 mol) in isopropyl alcohol (60 mL) was heated at reflux for 72 hours. The solution was allowed to cool to ambient temperature overnight. The resulting precipitate was isolated by filtration, washed with isopropyl alcohol and dried to provide isopropyl 6-morpholinonicotinate. The filtrate was diluted with water. The resulting precipitate was isolated by filtration, washed with water and dried to provide isopropyl 6-morpholinonicotinate. The combined yield was 8.3 g. The isopropyl 6-morpholinonicotinate was combined with 1 N sodium hydroxide (40 mL) and the resulting suspension was stirred at 50–60° C. until all of the solid had dissolved. The solution was stirred at ambient temperature overnight during which time a precipitate formed. This material was isolated by filtration and identified as starting material. The filtrate was neutralized with concentrated hydrochloric acid. The resulting precipitate was isolated by filtration, washed with water and dried to provide 3.3 g of crude product. This material was recrystallized from methanol/dichloromethane to provide 6-morpholinonicotinic acid as a solid, m.p. 259–261° C. Analysis: Calculated for $C_{10}H_{12}N_2O_3$: %C, 57.19; %H, 5.81; %N, 13.48; Found: %C, 57.50; %H, 5.71; %N, 13.53.

Part C

N,N-Dimethylformamide (1 mL) was slowly added to a solution of oxalyl chloride (0.13 g, 1 mmol) in chloroform (5 mL). 6-Morpholinonicotinic acid (0.21 g, 1 mmol) was added and the reaction mixture was stirred for 15 minutes. The reaction mixture was concentrated under vacuum, diluted with toluene and then concentrated under vacuum to provide 6-morpholinonicotinoyl chloride. This material was kept under vacuum at ambient temperature overnight and then used in the next step.

Part D

The acid chloride from Part C was dissolved in pyridine (20 mL) and then added all at once to a warm solution of 1-(4-aminobutyl)-1H-imidazo[4,5-c]quinolin-4-amine (0.25 g, 1 mmol) in pyridine (25 mL). The reaction mixture was concentrated under vacuum at 40° C. to remove the pyridine. The resulting residue was combined with water and 1N sodium hydroxide (25 mL). The mixture was extracted with dichloromethane. The extract was concentrated under vacuum. The resulting residue was recrystallized from isopropyl alcohol to provide $N^3$-[4-(4-amino-1H-imidazo[4,5-c]quinolin-1-yl)butyl]-6-morpholinonicotinamide as a solid, m.p. 160–170° C. (dec.). $^1$H NMR (500 MHz, DMSO-$d_6$) δ8.55 (d, J=2.5 Hz, 1H), 8.52 (s, 1H), 8.28 (t, J=6.0 Hz, 1H), 8.22 (d, J=8.0 Hz, 1H), 7.90 (dd, J=8.0, 2.5 Hz, 1H), 7.82 (d, J=8.0 Hz, 1H), 7.69 (t, J=8.0 Hz, 1H), 7.52 (d, J=8.0 Hz, 1H), 6.82 (d, J=8.0 Hz, 1H), 4.70 (t, J=7.0 Hz, 2H), 3.69 (t, J=5.0 Hz, 4H), 3.54 (t, J=5.0 Hz, 4H), 3.27 (q, J=6.0 Hz, 2H), 1.91(quintet, J=7.0 Hz, 2H), 1.58 (t, J=6.0 Hz, 2H); MS (EI) m/e 445.2209 (445.2226 calcd for $C_{24}H_{27}N_7O_2$).

EXAMPLE 13

$N^1$-[2-(4-Amino-1H-imidazo[4,5-c]quinolin-1-yl)ethyl]benzamide

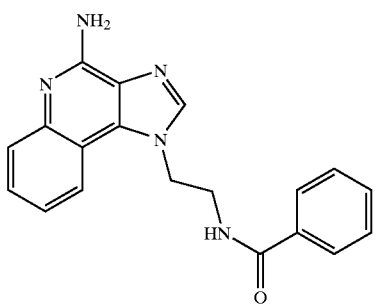

Part A

Triethylamine (66.8 g, 0.33 mol) was added to a solution of tert-butyl N-(2-aminoethyl)carbamate (55.0 g, 0.34 mol) in anhydrous dichloromethane (500 mL). 4-Chloro-3-nitroquinoline was slowly added and the reaction exothermed. The reaction mixture was allowed to stir at ambient temperature overnight. The resulting precipitate was isolated by filtration to provide product as a yellow solid. The filtrate was washed with water, dried over magnesium sulfate and then concentrated under vacuum. The resulting residue was slurried with hexane and filtered to provide additional product as a yellow solid. The two crops were combined to provide 101 g of tert-butyl N-[2-(3-nitroquinolin-4-yl)aminoethyl]carbamate as a yellow solid, m.p. 157–158.

Part B

Platinum on carbon (1 g of 10%) and sodium sulfate (2 g) were added to a slurry of tert-butyl N-[2-(3-nitroquinolin-4-yl)aminoethyl]carbamate (100 g, 0.30 mol) in toluene (500 mL). The mixture was placed under a hydrogen atmosphere at 50 psi (3.4×10$^4$ pascals) on a Parr apparatus at ambient temperature overnight. The reaction mixture was filtered. The filtrate was concentrated to provide 73 g of tert-butyl N-[2-(3-aminoquinolin-4-yl)aminoethyl] carbamate as a dark gold oil.

Part C

Triethyl orthoformate (11.3 g, 73.4 mmol) was added to a solution of tert-butyl N-[2-(3-aminoquinolin-4-yl) aminoethyl]carbamate (21 g, 69.4 mmol) in anhydrous toluene (250 mL). The reaction mixture was heated at reflux for 5 hours and then allowed to slowly cool to ambient temperature. The resulting precipitate was isolated by filtration and dried to provide 17.6 g of tert-butyl N-[2-(1H-imidazo[4,5-c]quinolin-1-yl)ethyl]carbamate as a light tan solid, m.p. 154–155° C.

Part D

3-Chloroperoxybenzoic acid (17.4 g, 60.6 mmol) was added in small portions to a solution of tert-butyl N-[2-(1H-imidazo[4,5-c]quinolin-1-yl)ethyl]carbamate (17.2 g, 55.1 mmol) in chloroform (250 mL). The reaction was maintained at ambient temperature overnight and then quenched with 5% sodium carbonate solution. The layers were separated. The organic layer was dried over magnesium sulfate and then concentrated under vacuum to provide 15.0 g of 1-[2-(tert-butylcarbamyl)ethyl]-1H-imidazo[4,5-c] quinoline-5N-oxide as an off white solid, m.p. 213–215° C.

Part E

Trichloroacetyl isocyanate (9.5 g, 50.2 mmol) was slowly added to a stirred solution of 1-[2-(tert-butylcarbamyl) ethyl]-1H-imidazo[4,5-c]quinoline-5N-oxide (15.0 g, 45.7 mmol) in chloroform (200 mL). After 2 hours the reaction was quenched with concentrated ammonium hydroxide (100 mL). Water (100 mL) was added and the layers were separated. The aqueous layer was extracted with chloroform. The organic layers were combined, dried over magnesium sulfate and then concentrated under vacuum to provide a white solid. This material was slurried in warm methyl acetate and then filtered to provide 15 g of tert-butyl N-[2-(4-amino-1H-imidazo[4,5-c]quinolin-1-yl)ethyl] carbamate as a white solid, m.p. 215° C. $^1$H NMR (500 MHz, DMSO-$d_6$) δ8.13 (t, J=8.0 Hz, 1H), 8.03 (s, 1H), 7.61(d, J=8.0 Hz, 1H), 7.44 (t, J=8.0 Hz, 1H), 7.23 (t, J=8.0 Hz, 1H), 7.06 (t, J=6.0 Hz, 1H), 6.56 (broad s, 2H), 4.63 (t, J=7.0 Hz, 2H), 3.43 (q, J=6.0 Hz, 2H), 1.32 (s, 9H); MS (EI) m/e 327.1696 (327.1695 calcd for $C_{17}H_{21}N_5O_2$)

Part F

Tert-butyl N-[2-(4-amino-1H-imidazo[4,5-c]quinolin-1-yl)ethyl]carbamate (14.8 g, 45.2 mmol), trifluoroacetic acid (100 mL) and acetonitrile (100 mL) were combined and maintained at ambient temperature overnight. The acetonitrile was removed and the reaction mixture was heated at reflux for 2 hours. The reaction mixture was concentrated under vacuum to provide a tan solid. This material was dissolved in a minimal amount of hot water. The solution was adjusted to pH 14 and allowed to cool. The solution was concentrated under vacuum. The resulting residue was extracted with refluxing ethanol. The ethanol extract was concentrated under vacuum to provide 3.0 g of 1-(2-aminoethyly-1H-imidazo[4,5-c]quinolin-4-amine as a tan solid, m.p. 265° C. $^1$H NMR (500 MHz, DMSO-d$_6$) δ8.14 (s, 1H), 8.08 (dd, J=8.0, 1.5 Hz, 1H), 7.62 (dd, J=8.0, 1.5 Hz, 1H), 7.44 (dt, J=8.0, 1.5 Hz, 1H), 7.25 (dt, J=8.0, 1.5 Hz, 1H), 6.58 (broad s, 2H), 4.54 (t, J=7.0 Hz, 2H), 3.01 (t, J=7.0 Hz, 2H), 1.60 (broad s, 2H); MS (EI) m/e 227.1171 (227.1171 calcd for C$_{12}$H$_{13}$N$_5$).

Part G

A mixture of 1-(2-aminoethyl)-1H-imidazo[4,5-c]quinolin-4-amine (0.40 g, 1.76 mmol) and anhydrous pyridine (60 mL) was heated until a clear solution was obtained. The solution was then cooled with an ice bath. Benzoyl chloride (0.25 g, 1.76 mmol) was added. The reaction mixture was maintained at ambient temperature overnight and then concentrated under vacuum. The residue was slurried with water (200 mL) and a solid was isolated by filtration. This material was recrystallized from isopropyl alcohol to provide 0.15 g of N$^1$-[2-(4-amino-1H-imidazo[4,5-c]quinolin-1-yl)ethyl]benzamide as a white powder, m.p. 295° C. $^1$H NMR (500 MHz, DMSO-d$_6$) δ8.50 (t, J=6.0 Hz, 1H), 8.23 (d, J=8.0 Hz, 1H), 8.04 (s, 1H), 7.75(d, J=8.0 Hz, 2H), 7.64 (d, J=8.0 Hz, 1H), 7.49 (t, J=8.0 Hz, 1H), 7.43 (t, J=8.0, 1H), 7.41 (t, J=8.0 Hz, 2H), 7.25 (t, J=8.0 Hz, 1H), 6.28 (broad s, 2H), 4.80(t, J=7.0 Hz, 2H), 3.80(q, J=6.0 Hz, 2H); MS (EI) m/e 331.1429 (331.1433 calcd for C$_{19}$H$_{17}$N$_5$O).

EXAMPLE 14

N$^1$-[4-(4-Amino-1H-imidazo[4,5-c]quinolin-1-yl)butyl]-2-phenoxybenzamide

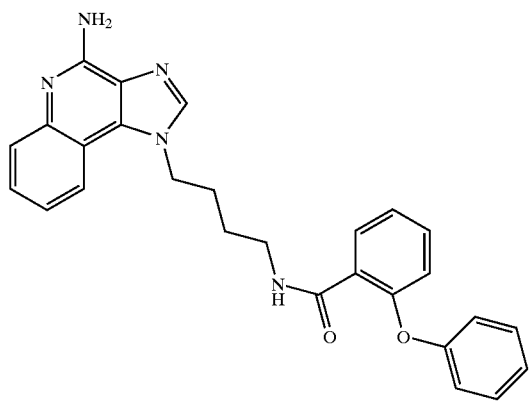

Under a nitrogen atmosphere, a mixture of 1-(4-aminobutyl)-1H-imidazo[4,5-c]quinolin-4-amine (0.125 g, 0.49 mmol) and anhydrous pyridine (40 mL) was warmed with a heat gun to dissolve the solid. The resulting solution was allowed to cool to ambient temperature. A solution of 2-phenoxybenzoyl chloride (0.11 g, 0.47 mmol) in pyridine (5 mL) was added. The reaction mixture was maintained at ambient temperature for 18 hours and then concentrated under vacuum. The resulting solid residue was purified by flash chromatography (silica gel eluting with 9:1 dichloromethane:methanol) to provide 0.12 g of N$^1$-[4-(4-amino-1H-imidazo[4,5-c]quinolin-1-yl)butyl]-2-phenoxybenzamide as a white solid, m.p. 93–94° C. $^1$H NMR (500 MHz, DMSO-d$_6$) δ8.23 (t, J=6.0 Hz, 1H), 8.14 (s, 1H), 8.00 (d, J=8.0 Hz, 1H), 7.62 (d, J=8.0 Hz, 1H), 7.54 (dd, J=8.0, 1.5 Hz, 1H), 7.43 (dt, J=8.0, 1.5 Hz, 1H), 7.42 (dt, J=8.0, 1.5 Hz, 1H), 7.30 (t, J=8.0 Hz, 2H), 7.22 (t, J=8.0 Hz, 1H), 7.18 (t, J=8.0 Hz, 1H), 7.07 (t, J=8.0 Hz, 1H), 6.89 (m, 3H), 6.59 (broad s, 2H), 4.55 (t, J=7.0 Hz, 2H), 3.23 (q, J=6.0 Hz, 2H), 1.81 (quintet, J=7.0 Hz, 2H), 1.47 (quintet, J=7.0 Hz, 2H); MS (EI) m/e 451.2004 (451.2008 calcd for C$_{27}$H$_{25}$N$_5$O$_2$).

EXAMPLE 15

N$^1$-[4-(4-Amino-1H-imidazo[4,5-c]quinolin-1-yl)butyl]-3-benzoylbenzamide

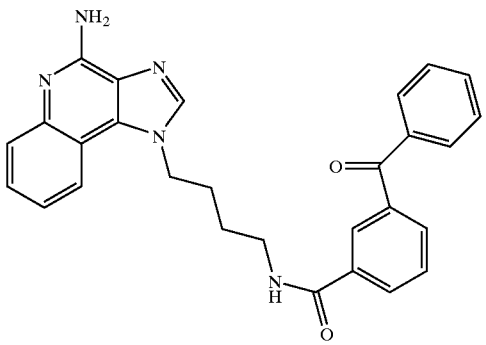

Using the method of Example 14, 1-(4-aminobutyl)-1H-imidazo[4,5-c]quinolin-4-amine (0.2 g, 0.78 mmol) was reacted with 3-benzoylbenzoyl chloride (0.18 g, 0.73 mmol) to provide 0.19 g of N$^1$-[4-(4-amino-1H-imidazo[4,5-c]quinolin-1-yl)butyl]-3-benzoylbenzamide as a white crystalline solid, m.p. 103–105° C. $^1$H NMR (500 MHz, DMSO-d$_6$) δ8.70 (t, J=6.0 Hz, 1H), 8.22 (s, 1H), 8.16 (broad s, 1H), 8.08 (d, J=8.0 Hz, 1H), 8.03 (d, J=8.0 Hz, 1H), 7.85 (d, J=8.0 Hz, 1H), 7.73 (d, J=8.0 Hz, 2H), 7.70 (t, J=8.0 Hz, 1H), 7.64 (t, J=8.0 Hz, 1H), 7.61 (d, J=8.0 Hz, 1H), 7.57 (t, J=8.0 Hz, 2H), 7.40 (t, J=8.0 Hz, 1H), 7.19 (t, J=8.0 Hz, 1H), 6.67 (broad s, 2H), 4.63 (t, J=7.0 Hz, 2H), 3.32 (q, J=6.0 Hz, 2H), 1.91 (quintet, J=7.0 Hz, 2H), 1.59 (quintet, J=7.0 Hz, 2H); MS (EI) m/e 463.2022 (463.2008 calcd for C$_{28}$H$_{25}$N$_5$O$_2$).

EXAMPLE 16

N$^1$-[4-(4-Amino-1H-imidazo[4,5-c]quinolin-1-yl)butyl]-3-phenylpropanamide

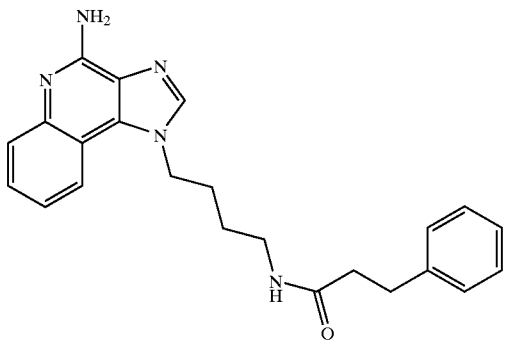

Using the method of Example 14, 1-(4-aminobutyl)-1H-imidazo[4,5-c]quinolin-4-amine (0.2 g, 0.78 mmol) was reacted with hydrocinnamoyl chloride (0.11 mL, 0.74 mmol) to provide 0.14 g of N$^1$-[4-(4-amino-1H-imidazo[4,5-c]

quinolin-1-yl)butyl]-3-phenylpropanamide as a white solid, m.p. 148–150° C. $^1$H NMR (500 MHz, DMSO-$d_6$) δ8.19 (s, 1H), 8.03 (d, J=8.0 Hz, 1H), 7.82 (t, J=6.0 Hz, 1H), 7.63 (d, J=8.0 Hz, 1H), 7.45 (t, J=8.0 Hz, 1H), 7.27 (t, J=8.0 Hz, 1H), 7.22 (t, J=8.0 Hz, 2H), 7.15 (m, 3H), 6.66 (broad s, 2H), 4.58 (t, J=7.0 Hz, 2H), 3.06 (q, J=6.0 Hz, 2H), 2.75 (t, J=7.0 Hz, 2H), 2.31 (t, J=7.0 Hz, 2H), 1.79 (quintet, J=7.0 Hz, 2H), 1.40 (t, J=7.0 Hz, 2H); MS (EI) m/e 387.2067 (387.2059 calcd for $C_{23}H_{25}N_5O$).

EXAMPLE 17

$N^1$-[2-(4-Amino-1H-imidazo[4,5-c]quinolin-1-yl)ethyl]-3-phenylpropanamide

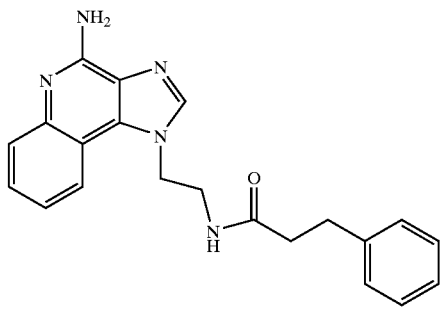

Using the method of Example 14, 1-(2-aminoethyl)-1H-imidazo[4,5-c]quinolin-4-amine (100 mg, 0.44 mmol) was reacted with hydrocinnamoyl chloride (0.065 mL, 0.44 mmol) to provide 0.06 g of $N^1$-[2-(4-amino-1H-imidazo[4,5-c]quiolin-1-yl)ethyl]-3-phenylpropanamide as a white solid, m.p. 254–256° C. $^1$H NMR (500 MHz, DMSO-$d_6$) δ8.16 (d, J=8.0 Hz, 1H), 8.07 (t, J=6.0 Hz, 1H), 7.97 (s, 1H), 7.62 (dd, J=8.0, 1.0 Hz, 1H), 7.45 (dt, J=8.0, 1.0 Hz, 1H), 7.26 (m, 3H), 7.16 (m, 3H), 6.6 (broad s, 2H), 4.61 (t, J=7.0 Hz, 2H), 3.54 (q, J=6.0 Hz, 2H), 2.75 (t, J=7.0 Hz, 2H), 2.31 (t, J=7.0 Hz, 2H), MS (EI) m/e 359.1745 (359.1746 calcd for $C_{21}H_{21}N_5O$).

EXAMPLE 18

$N^1$-[4-(4-Amino-1H-imidazo[4,5-c]quinolin-1-yl)butyl]-2-(4-benzoylphenoxy)acetamide

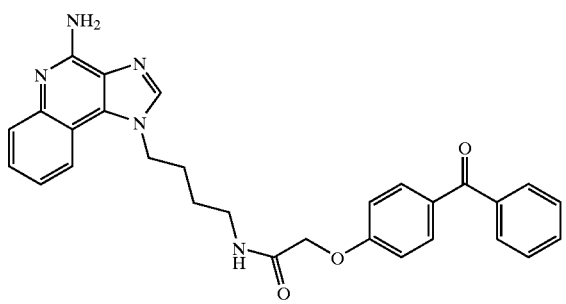

1-(4-Aminobutyl)-1H-imidazo[4,5-c]quinolin-4-amine (99.6 mg, 0.39 mmol) and 2-(4-benzoylphenoxy)acetic acid (100 mg, 0.39 mmol) were combined in pyridine (10 mL). The mixture was warmed until homogeneous and then allowed to cool. 1-[3-(dimethylamino)propyl]-3-ethylcarbodiimide hydrochloride (82 mg, 0.43 mole) was added. The reaction mixture was maintained at ambient temperature overnight and then concentrated under vacuum. The residue was partitioned between chloroform and saturated potassium carbonate solution. The layers were separated. The aqueous layer was extracted with chloroform. The organic layers were combined, dried over magnesium sulfate and then concentrated under vacuum to provide a gold oil. The oil was purified by column chromatography (silica gel eluting with 10% methanol in dichloromethane) to provide about 70 mg of $N^1$-[4-(4-amino-1H-imidazo[4,5-c]quinolin-1-yl)butyl]-2-(4-benzoylphenoxy)acetamide as a white solid, m.p. 73–98° C. $^1$H NMR (500 MHz, DMSO-$d_6$) δ8.22 (t, J=6.0 Hz, 1H), 8.18 (s, 1H), 8.03 (d, J=8.3 Hz, 1H), 7.73 (d, J=8.0 Hz, 2H), 7.68 (d, J=8.0 Hz, 2H), 7.65 (t, J=8.0 Hz, 1H), 7.60 (dd, J=8.0, 1.0 Hz, 1H), 7.55 (t, J=8.0 Hz, 2H), 7.42 (dt, J=8.0, 1.0 Hz, 1H), 7.25 (t, J=8.0, 1.0 Hz, 1H), 7.07 (d, J=8.0 Hz, 2H), 6.58 (broad s, 2H), 4.61 (t, J=7.0 Hz, 2H), 4.56 (s, 2H), 3.18 (q, J=6.0 Hz, 2H), 1.86 (quintet, J=7.0 Hz, 2H), 1.50 (quintet, J=7.0 Hz, 2H); MS (EI) m/e 493.2106 (493.2114 calcd for $C_{29}H_{27}N_5O_3$).

EXAMPLE 19

N-[4-Amino-1H-imidazo[4,5-c]quinolin-1-yl]butyl-5-[(2-oxo-2,3-dihydro-1H-benzo[d]imidazol-5-yl)oxy]pentamide

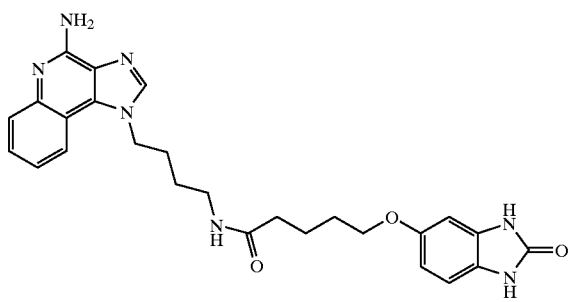

Using the general method of Example 18, 1-(4-aminobutyl)-1H-imidazo[4,5-c]quinolin-4-amine (100 mg, 0.392 mmol) was coupled with 5-[(2-oxo-2,3-dihydro-1H-benzo[d]imidazol-5-yl)oxy]pentanoic acid (98.1 mg, 0.392 mmol) to provide 20 mg of N-[4-amino-1H-imidazo[4,5-c]quinolin-1-yl]butyl-5-[(2-oxo-2,3-dihydro-1H-benzo[d]imidazol-5-yl)oxy]pentamide as an off-white solid, m.p.150–157° C. $^1$H NMR (500 MHz, DMSO-$d_6$) δ10.51 (s, 1H), 10.36 (s, 1H), 8.23 (s, 1H), 8.05(d, J=8.0 Hz, 1H), 7.81 (t, J=6.0 Hz, 1H), 7.64 (t, J=6.0 Hz, 1H), 7.47 (t, J=8.0 Hz, 1H), 7.29 (t, J=8.0 Hz, 1H), 6.93 (broad s, 2H), 6.78(d, J=8.0 Hz, 1H), 6.48 (s, 1H), 6.47 (d, J=8.0 Hz, 1H), 4.61 (t, J=7.0 Hz, 2H), 3.82 (broad s, 2H), 3.08 (q, J=6.0 Hz, 2H), 2.05 (t, J=7.0 Hz, 2H), 1.84 (quintet, J=7.0 Hz, 2H), 1.58 (broad s, 4H), 1.44 (quintet, J=7.0 Hz, 2H); MS (EI) m/e 487.2329 (487.2332 calcd for $C_{26}H_{29}N_7O_3$).

EXAMPLE 20

N¹-[4-(4-Amino-1H-imidazo[4,5-c]quinolin1 -yl) butyl]-4-benzoylbenzamide

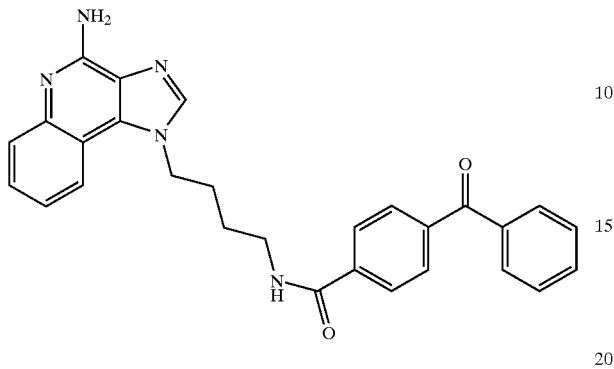

Using the general method of Example 14, 1-(4-aminobutyl)-1H-imidazo[4,5-c]quinolin-4-amine (0.51 g, 2.0 mmol) was reacted with 4-benzoylbenzoyl chloride (2.0 mmol) to provide 0.15 g of N¹-[4-(4-amino-1H-imidazo[4,5-c]quinolin1-yl)butyl]-4-benzoylbenzamide as a white solid, m.p. 159–161° C. ¹H NMR (500 MHz, CDCl$_3$) δ8.06 (s, 1H), 7.96 (d, J=8.0 Hz, 1H), 7.91 (d, J=8.0 Hz, 1H), 7.85 (d, J=8.0 Hz, 2H), 7.81 (d, J=8.0 Hz, 2H), 7.76 (d, J=8.0 Hz, 2H), 7.60 (m, 2H), 7.49 (t, J=8.0 Hz, 2H), 7.48 (t, J=8.0 Hz, 1H), 7.24 (broad s, 1H), 6.86 (broad s, 1H), 6.60 (t, J=6 Hz, 1H), 4.69 (t, J=7.0 Hz, 2H), 3.62 (q, J=6.0 Hz, 2H), 2.14 (quintet, J=7.0 Hz, 2H), 1.82 (quintet, J=7.0 Hz, 2H); MS (EI) m/e 463.2002 (463.2008 calcd for C$_{28}$H$_{25}$N$_5$O$_2$).

EXAMPLE 21

N⁶-[4-(4-Anino-1H-imidazo[4,5-c]quinolin-1-yl) butyl]-6-quinolinecarboxamide

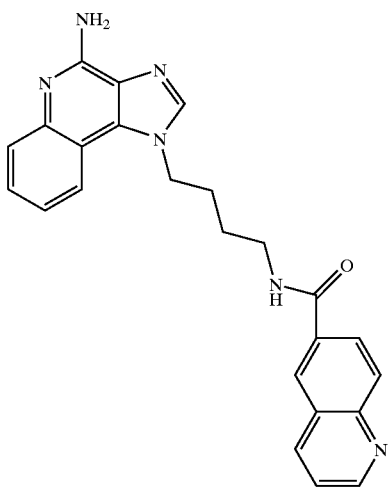

Using the general method of Example 18, 1-(4-aminobutyl)-1H-imidazo[4,5-c]quinolin-4-amine (0.5 g, 1.96 mmol) was coupled with 6-quinolinecarboxylic acid (0.34 g, 1.96 mmol) to provide 0.08 g of N⁶-[4-(4-amino-1H-imidazo[4,5-c]quinolin-1-yl)butyl]-6-quinolinecarboxamide as a tan powder, m.p. 122–127° C. (foaming). ¹H NMR (300 MHz, DMSO-d$_6$) δ8.98 (m, 1H), 8.73 (t, J=5.4 Hz, 1H), 8.43 (m, 2H), 8.23 (s, 1H), 8.13–8.03 (m, 3H), 7.60 (m, 2H), 7.40 (m, 1H), 7.20 (m, 1H), 6.58 (broad s, 2H), 4.66 (t, J=6.7 Hz, 2H), 3.37 (m, 2H), 1.96 (m, 2H), 1.64 (m, 2H); MS (EI) m/e 410.1847 (410.1855 calcd for C$_{24}$H$_{22}$N$_6$O).

EXAMPLE 22

N¹-[3-(4-Amino-2-methyl-1H-imidazo[4,5-c] quinolin-1-yl)propyl]benzamide

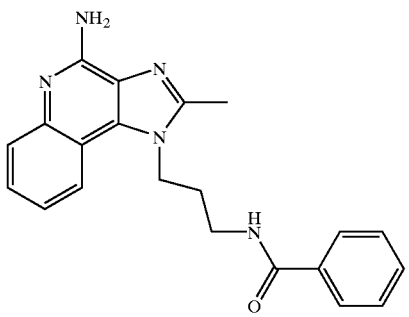

Part A

Using the general method of Example 11 Part C, N¹-{3-[(3-nitroquinolin-4-yl)amino]propyl}benzamide (2.0 g, 5.7 mmol) was reduced to the diamine and then reacted with triethylorthoacetate to provide 0.74 g of N¹-[3-(2-methyl-1H-imidazo[4,5-c]quinolin-1-yl)propyl]benzamide as a sticky dark yellow solid.

Part B

Using the general method of Example 11 Part D, the material from Part A was oxidized to provide 0.35 g of 1-(3-benzamidopropyl)-2-methyl-1H-imidazo[4,5-c] quinoline-5N-oxide as a solid.

Part C

Ammonium hydroxide (20 mL) was added to a solution of 1-(3-benzamidopropyl)-2-methy-1H-imidazo[4,5-c] quinoline-5N-oxide (0.35 g, 0.97 mmol) in dichloromethane (100 mL). Tosyl chloride (0.185 g, 0.97 mmol) was slowly added with vigorous stirring. The reaction mixture was stirred overnight at ambient temperature and then it was concentrated under vacuum to remove the dichloromethane. The resulting solid was recrystallized from dichloromethane to provide 0.1 g of N¹-[3-(4-amino-2-methyl-1H-imidazo[4, 5-c]quinolin-1-yl)propyl]benzamide as a solid, m.p. 230–231.4° C.

EXAMPLE 23

N$^1$-[6-(4-Amino-1H-imidazo[4,5-c]quinolin-1-yl)hexyl]benzamide

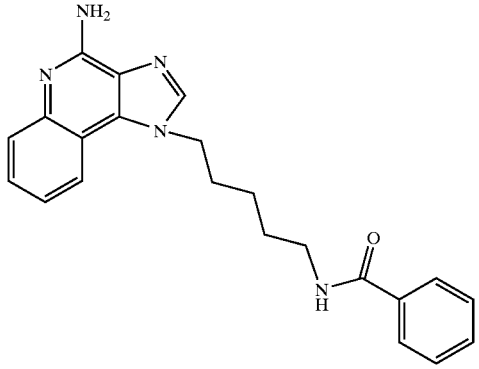

Part A

Using the general method of Example 9 Part A, hexamethylenediamine (348.63 g, 3 mol) was reacted with benzamide (121.14 g, 1 mole) to provide 136.5 g of N-(6-aminohexyl)benzamide.

Part B

Using the general method of Example 9 Part B, 4-chloro-3-nitroquinoline hydrochloride (10 g, 41 mnmol) was reacted with N-(6-aminohexyl)benzamide to provide 12.85 g of N$^1$-{6-[(3-nitroquinolin-4-yl)amino]hexyl}benzamide as a yellow crystalline solid.

Part C

Using the general method of Example 9 Part C, 12.3 g of the material from part B was reduced and then reacted with triethylorthoformate (8.94 g, 6 mmol) to provide 6.4 g of N$^1$-[6-(1H-imidazo[4,5-c]quinolin-1-yl)hexyl]benzamide as a brown oil.

Part D

3-Chloroperoxybenzoic acid (5.9 g, 17 mmol) was slowly added to a solution of the material from Part C in chloroform. The solution turned orange. After 2 hours the reaction mixture was washed twice with aqueous sodium carbonate and then concentrated under vacuum to provide 6.0 g of 1-(6-benzamidohexyl)-1H-imidazo[4,5-c]quinoline-5N-oxide as an orange oil.

Part E

Ammonium hydroxide was added to a solution of the material from Part D in dichloromethane. Tosyl chloride (2.94 g, 15 mmol) was slowly added with vigorous stirring. The reaction mixture was allowed to stir at ambient temperature overnight and then it was concentrated under vacuum. The resulting crude material was recrystallized from propyl acetate to provide 0.91 g of N$^1$-[6-(4-amino-1H-imidazo[4,5-c]quinolin-1-yl)hexyl]benzamide as a beige crystalline solid, m.p. 146–155° C.

EXAMPLE 24

N$^1$-[4-(4-Amino-2-butyl-1H-imidazo[4,5-c]quinolin-1-yl)butyl]-5-(2-oxoperhydrothieno[3,4-d]imidazol-4-yl)pentanamide

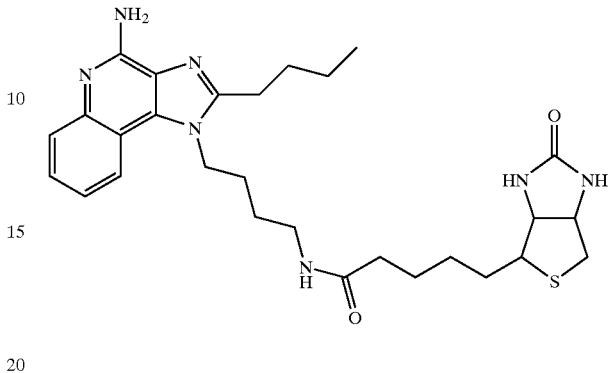

D-biotinyl N-hydroxysuccinimide (0.57 g, 1.67 mmol) was added to a solution of 1-(4-aminobutyl)-2-butyl-1H-imidazo[4,5-c]quinolin-4-amine (0.52 g, 1.67 mmol) in pyridine (25 mL). The reaction was maintained at ambient temperature overnight and then concentrated to dryness. The residue was partitioned between dichioromethane and aqueous saturated potassium carbonate. The organic layer was dried over magnesium sulfate and then concentrated to provide 0.4 g of N$^1$-[4-(4-amino-2-butyl-1H-imidazo[4,5-c]quinolin-1-yl)-5-(2-oxoperhydrothieno[3,4-d]imidazol-4-yl)pentamide as a solid, m.p. 214–215° C. Analysis: Calculated for $C_{28}H_{39}N_7O_2S$: %C, 62.54; %H, 7.31; %N, 18.23; Found: %C, 61.67; %H, 7.37; %N, 17.62.

EXAMPLE 25

N$^1$-[4-(4-Amino-1H-imidazo[4,5-c]quinolin-1-yl)butyl]-5-(2-oxoperhydrothieno[3,4-d]imidazol-4-yl)pentanamide

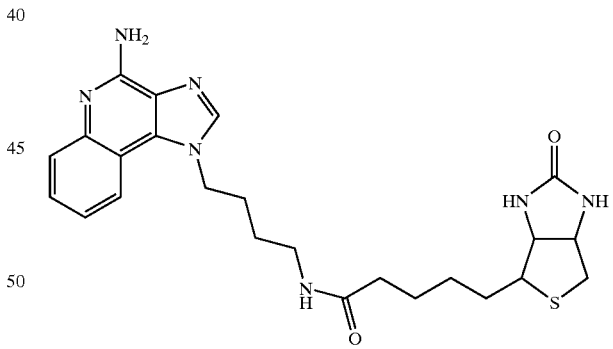

A solution of 1-(4-aminobutyl)-1H-imidazo[4,5-c]quinolin-4-amine (0.38 g, 1.49 mmol) in pyridine (20 mL) was added to a solution of N-hydroxysuccinimidobiotin (0.51 g, 1.49 mmol) in pyridine (20 mL). The reaction was maintained at ambient temperature overnight and then concentrated to dryness. The residue was partitioned between dichloromethane and aqueous saturated potassium carbonate. The organic layer was dried over magnesium sulfate and then concentrated to provide 0.58 g of N$^1$-[4-(4-amino-1H-imidazo[4,5-c]quinolin-1-yl)-5-(2-oxoperhydrothieno[3,4-d]imidazol-4-yl)pentamide as a solid, m.p. 104–106° C. High resolution mass spec: Theoretical mass=481.2260, Measured mass=481.2261.

EXAMPLE 26

N[1]-[2-(4-Amino-2-butyl-1H-imidazo[4,5-c]quinolin-1-yl)ethyl]-5-(2-iminoperhydrothieno[3,4-d]imidazol-4-yl)pentanamide

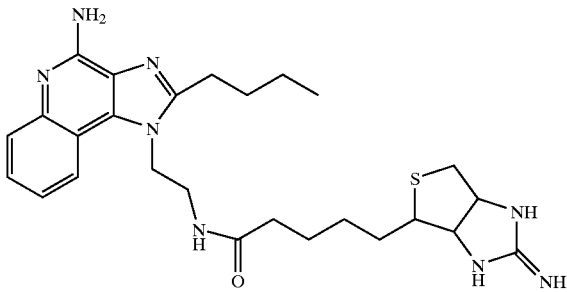

A solution of N-hydroxysuccinimidoiminobiotin (0.74 g, 1.76 mmol) in pyridine (10 mL) was slowly added to a solution of 1-(2-aminoethyl)-2-butyl-1H-imidazo[4,5-c]quinolin-4-amine (0.50 g, 1.76 mmol) in pyridine (30 mL). The reaction was maintained at ambient temperature overnight and then concentrated to dryness. The residue was partitioned between dichloromethane and aqueous saturated potassium carbonate. The organic layer was dried over magnesium sulfate and then concentrated to dryness. The residue was recrystallized from ethanol to provide 0.5 g of N[1]-[2-(4-amino-2-butyl-1H-imidazo[4,5-c]quinolin-1-yl)ethyl]-5-(2-iminoperhydrothieno[3,4-d]imidazol-4-yl)pentanamide as a solid, m.p. 95–96° C. High resolution mass spec: Theoretical mass=508.2733, Measured mass=508.2723.

EXAMPLE 27

N[1]-[2-(4-Amino-1H-imidazo[4,5-c]quinolin-1-yl)ethyl]-5-(2-oxoperhydrothieno[3,4-d]imidazol-4-yl)pentanamide

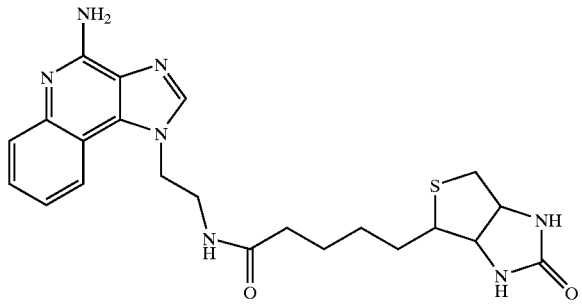

Using the general method of Example 24, N-hydroxysuccinimidobiotin (0.6 g, 1.76 mmol) was reacted with 1-(2-aminoethyl)-1H-imidazo[4,5-c]quinolin-4-amine (0.4 g, 1.76 mmol) to provide 0.6 g of N[1]-[2-(4-amino-1H-imidazo[4,5-c]quinolin-1-yl)ethyl]-5-(2-oxoperhydrothieno[3,4-d]imidazol-4-yl)pentanamide as a solid, m.p. 169° C.

EXAMPLE 28

N[1]-[2-(4-Amino-2-butyl-1H-imidazo[4,5-c]quinolin-1-yl)ethyl]-5-(2-oxoperhydrothieno[3,4-d]imidazol-4-yl)pentanamide

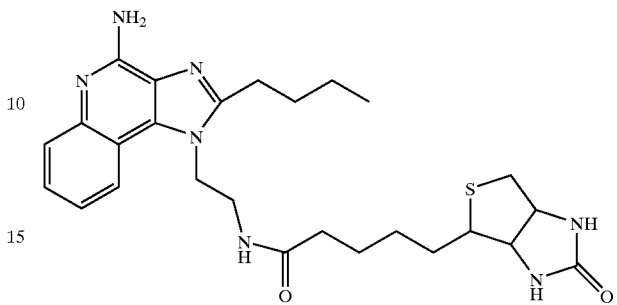

Using the general method of Example 25, 1-(4-aminoethyl)-2-butyl-1H-imidazo[4,5-c]quinolin-4-amine (0.4 g, 1.47 mmol) was reacted with N-hydroxysuccinimidobiotin (0.5 g, 1.47 mmol) to provide 0.44 g of N[1]-[2-(4-amino-2-butyl-1H-imidazo[4,5-c]quinolin-1-yl)ethyl]-5-(2-oxoperhydrothieno[3,4-d]imidazol-4-yl)pentanamide as a white solid, m.p. 124–126° C. High resolution mass spec: Theoretical mass=509.25, Measured mass=509.2580.

EXAMPLE 29

N[1]-[2-(4-Amino-2-(ethoxymethyl)-1H-imidazo[4,5-c]quinolin-1-yl)ethyl]-5-(2-oxoperhydrothieno[3,4-d]imidazol-4-yl)pentanamide Ditrifluoroacetate

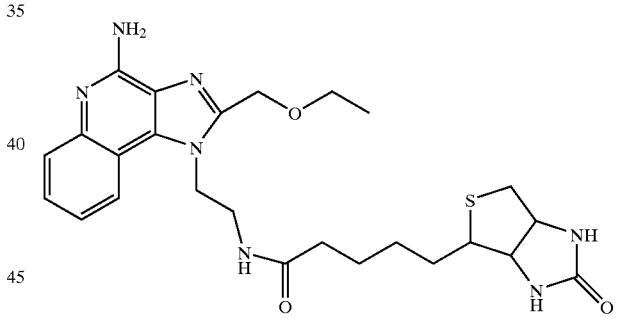

Triethylamine (1.2 g, 11.4 mmol) was added in a single portion to a slurry of 1-(2-aminoethyl)-2-(ethoxymethyl)-1H-imidazo[4,5-c]quinolin-4-amine hydrochloride (3.39 g, 10.53 mmol) in chloroform (150 mL). The reaction mixture became clear. N-hydroxysuccinimidobiotin (3.0 g, 8.79 mmol) was then slowly added. After 2 hours the turbid reaction mixture was heated to reflux. The reaction mixture was maintained at reflux overnight and became clear. The reaction mixture was allowed to cool to ambient temperature and then it was quenched with water. The layers were separated. The organic layer was dried over magnesium sulfate and then concentrated to provide an off-white solid. This material was recrystallized from 8:2 ethanol:water to provide a white solid. A portion of this material was purified by prep HPLC eluting with water/acetonitrile/trifluoroacetic acid to provide 0.6 g of N[1]-[2-(4-amino-2-(ethoxymethyl)-1H-imidazo[4,5-c]quinolin-1-yl)ethyl]-5-(2-oxoperhydrothieno[3,4-d]imidazol-4-yl)pentanamide as the ditrifluoroacetate salt, m.p. 171–175° C. Analysis: Calcu-

EXAMPLE 30

N¹-[4-(4-Amino-2-butyl-1H-imidazo[4,5-c]quinolin-1-yl)butyl]-6-(5-methyl-2-oxo-4-imidazolinyl)hexaneamide

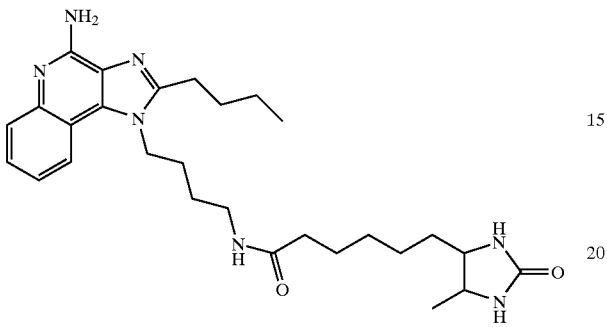

1-(4-Aminobutyl)-2-butyl-1H-imidazo[4,5-c]quinolin-4-amine (0.13 g, 0.47 mmol), D-desthiobiotin (0.10 g, 0.47 mmol) and chloroform (200 mL) were combined and stirred at ambient temperature until a clear solution was obtained. 1-[3-(dimethylamino)propyl-3-ethylcarbodiimide hydrochloride (0.094 g, 0.49 mmol) was added and the reaction mixture was maintained at ambient temperature overnight. The reaction mixture was poured onto a silica gel column. The chloroform was allowed to run off and then the column was eluted with 10% methanol in dichloromethane. The pure fractions were combined and concentrated to provide N¹-[4-(4-amino-2-butyl-1H-imidazo[4,5-c]quinolin-1-yl)butyl]-6-(5-methyl-2-oxo-4-imidazolinyl)hexaneamide as a white solid.

EXAMPLE 31

N¹-[4-(4-Amino-1H-imidazo[4,5-c]quinolin-1-yl)butyl]-2-ethoxy-1-naphthamide

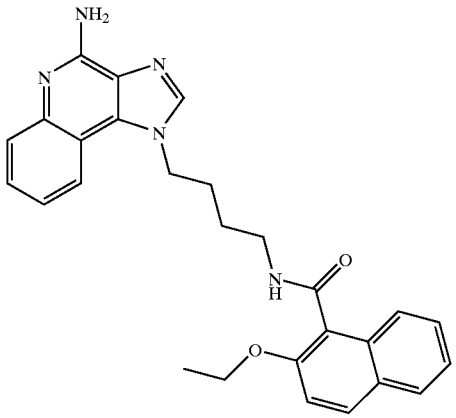

According to the general method of Example 14, 1-(4-aminobutyl)-1H-imidazo[4,5-c]quinolin-4-amine and 2-ethoxy-1-naphthoyl chloride were combined to provide N¹-[4-(4-amino-1H-imidazo[4,5-c]quinolin-1-yl)butyl]-2-ethoxy-1-naphthamide as a white powder, m.p. 219° C. (decomposition). ¹H NMR (300 MHz, DMSO-$d_6$) $\delta$ 8.33 (t, J=5.8 Hz, 1H), 8.22 (s, 1H), 8.09 (d, J=8.0 Hz, 1H), 7.91 (d, J=8.7 Hz, 1H), 7.87–7.84 (m, 1H), 7.64–7.56 (m, 2H), 7.47–7.22 (m, 5H), 6.60 (s, 2H), 4.69 (t, J=7.2 Hz, 2H), 4.09 (q, J=7.2 Hz, 2H), 3.37 (m, 2H), 2.01 (m, 2H), 1.64 (m, 2H), 1.18 (t, J=7.2 Hz, 3H); MS (EI) m/e 453.2157 (453.2165 calcd for $C_{27}H_{27}N_5O_2$).

EXAMPLE 32

N¹-[4-(4-Amino-1H-imidazo[4,5-c]quinolin-1-yl)butyl]-4-cyanobenzamide

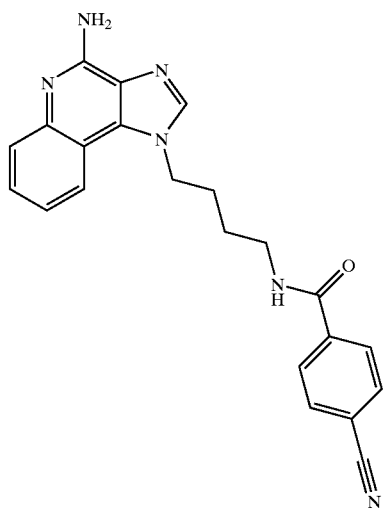

According to the general method of Example 14, 1-(4-aminobutyl)-1H-imidazo[4,5-c]quinolin-4-amine and 4-cyanobenzoyl chloride were combined to provide N¹-[4-(4-amino-1H-imidazo[4,5-c]quinolin-1-yl)butyl]-4-cyanobenzamide as a white powder, m.p. 222.8–225.3 ° C. ¹H NMR (300 MHz, DMSO-$d_6$) $\delta$ 8.73 (t, J=5.7 Hz, 1H), 8.22 (s, 1H), 8.03 (d, J=8.1 Hz, 1H), 7.93 (s, 4H), 7.61 (dd, J=8.4, 1.2 Hz, 1H), 7.43 (dt, J=7.6, 1.5 Hz, 1H), 7.21 (dt, J=7.6, 1.2 Hz, 1H), 6.61 (s, 2H), 4.64 (t, J=7.2 Hz, 2H), 3.33 (m, 2H), 1.96 (quintet, J=7.2 Hz, 2H), 1.58 (quintet, J=7.2 Hz, 2H); IR (KBr) 3441, 3337, 3136, 2945, 2228, 1641, 1545, 1531, 1481, 1396, 1309, 1257, 857, 755 cm⁻¹; MS (El) m/e 384.1699 (384.1699 calcd for $C_{22}H_{20}N_6O$).

lated for: $C_{25}H_{33}N_7O_3S \cdot 2\ C_2HF_3O_2$: %C, 47.09; %H, 4.77; %N, 13.26; Found: %C, 47.06; %H, 5.17; %N, 13.31.

EXAMPLE 33

N¹-[4-(4-Amino-1H-imidazo[4,5-c]quinolin-1-yl)butyl]-3-cyanobenzamide

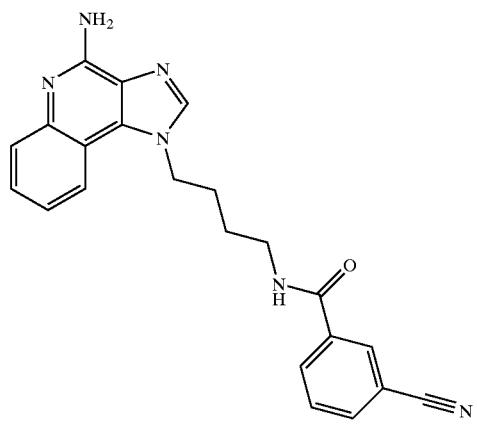

According to the general method of Example 14, 1-(4-aminobutyl)-1H-imidazo[4,5-c]quinolin-4-amine and 3-cyanobenzoyl chloride were combined to provide N¹-[4-(4-amino-1H-imidazo[4,5-c]quinolin-1-yl)butyl]-3-cyanobenzamide as a white crystalline solid, m.p. 200.0–201.0° C. (decomposition). $^1$H NMR (300 MHz, DMSO-$d_6$) δ8.68 (t, J=5.7 Hz, 1H), 8.22 (s, 1H), 8.17 (t, J=1.8 Hz, 1H), 8.10–7.97 (m, 3H), 7.69–7.60 (m, 2H), 7.42 (dt, J=7.5, 1.2 Hz, 1H), 7.20 (dt, J=7.5, 1.5 Hz, 1H), 6.62 (s, 2H), 4.63 (t, J=6.9 Hz, 2H), 3.32 (m, 2H), 1.91 (quintet, J=7.5 Hz, 2H), 1.59 (quintet, J=7.5 Hz, 2H); IR (KBr) 3455, 3295, 3072, 2941, 2231, 1638, 1581, 1527, 1479, 1396, 1312, 1251, 1205 cm$^{-1}$; MS (EI) m/e 384.1699 (384.1699 calcd for $C_{22}H_{20}N_6O$).

EXAMPLE 34

N¹-[4-(4-Amino-1H-imidazo[4,5-c]quinolin-1-yl)butyl]-4-phenylbenzamide

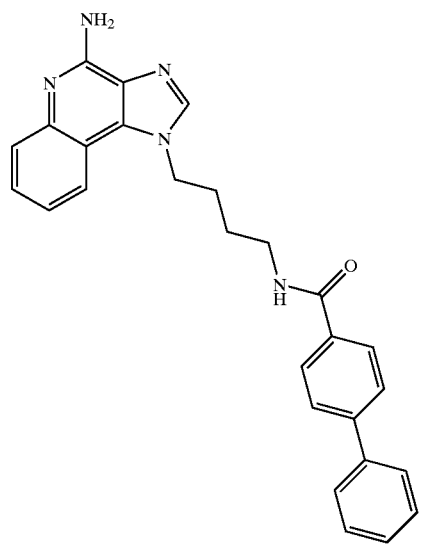

According to the general method of Example 14, 1-(4-aminobutyl)-1H-imidazo[4,5-c]quinolin-4-amine and 4-biphenylcarbonyl chloride were combined to provide N¹-[4-(4-amino-1H-imidazo[4,5-c]quinolin-1-yl)butyl]-4-phenylbenzamide as a white powder, m.p. 215.4° C. (decomposition). $^1$H NMR (300 MHz, DMSO-$d_6$) δ8.54 (t, J=5.7 Hz, 1H), 8.22 (s, 1H), 8.05 (d, J=7.2 Hz, 1H), 7.88 (d, J=5.4 Hz, 2H), 7.75–7.70 (m, 4H), 7.62 (dd, J=8.4, 1.5 Hz, 1H), 7.52–7.38 (m, 4H), 7.22 (dt, J=7.5, 1.2 Hz, 1H), 6.61 (s, 2H), 4.65 (t, J=7.2 Hz, 2H), 3.30 (m, 2H), 1.93 (quintet, J=7.5 Hz, 2H), 1.60 (quintet, J=7.5 Hz, 2H); MS (EI) m/e 435.2054 (435.2059 calcd for $C_{27}H_{25}N_5O$).

EXAMPLE 35

N¹-[4-(4-Amino-1H-imidazo[4,5-c]quinolin-1-yl)butyl]-2-phenoxyacetamide

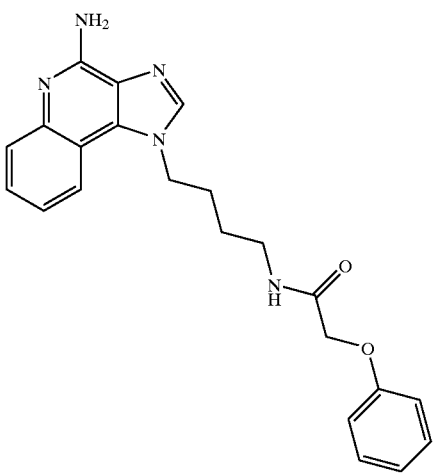

According to the general method of Example 14, 1-(4-aminobutyl)-1H-imidazo[4,5-c]quinolin-4-amine and phenoxyacetyl chloride were combined to provide N¹-[4-(4-amino-1H-imidazo[4,5-c]quinolin-1-yl)butyl]-2-phenoxyacetamide as an off white powder, m.p. 61.5° C. (decomposition). $^1$H NMR (300 MHz, DMSO-$d_6$) δ8.19 (s, 1H), 8.12 (t, J=6.0 Hz, 1H), 8.03 (d, J=8.4 Hz, 1H), 7.62 (dd, J=8.4, 1.2 Hz, 1H), 7.44 (dt, J=7.5, 1.2 Hz, 1H), 7.29–7.21 (m, 3H), 6.96–6.88 (m, 3H), 6.62 (s, 2H), 4.60 (t, J=7.2 Hz, 2H), 4.42 (s, 2H), 3.16 (q, J=6.9 Hz, 2H), 1.83 (quintet, J=7.2 Hz, 2H), 1.47 (quintet, J=7.2 Hz, 2H); IR (KBr) 3311, 3180, 2937, 1664, 1618, 1583, 1527, 1493, 1480, 1396, 1244, 755 cm$^{-1}$; MS (EI) m/e 389.1844 (389.1852 calcd for $C_{22}H_{23}N_5O_2$).

EXAMPLE 36

N$^1$-[4-(4-Amino-1H-imidazo[4,5-c]quinolin-1-yl)butyl]-2-ethylhexanamide

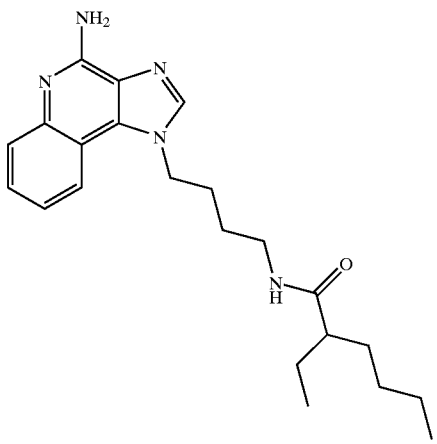

According to the general method of Example 14, 1-(4-aminobutyl)-1H-imidazo[4,5-c]quinolin-4-amine and 2-ethylhexanoyl chloride were combined to provide N$^1$-[4-(4-amino-1H-imidazo[4,5-c]quinolin-1-yl)butyl]-2-ethylhexanamide as a tan powder, m.p. 163.0–164.0° C. $^1$H NMR (300 MHz, DMSO-d$_6$) δ8.19 (s, 1H), 8.03 (d, J=8.1 Hz, 1H), 7.79 (m, 1H), 7.61 (dd, J=8.1, 1.2 Hz 1H), 7.44 (dt, J=7.5, 1.2 Hz, 1H), 7.26 (dt, J=7.5, 1.2 Hz, 1H), 6.63 (s, 2H), 4.61 (t, J=6.9 Hz, 2H), 3.12–3.05 (m, 2H), 1.94–1.82 (m, 3H), 1.49–1.03 (m, 10H), 0.76 (t, J=7.2 Hz, 3H), 0.67 (t, J=7.2 Hz, 3H), MS (EI) m/e 381.2533 (381.2529 calcd for C$_{22}$H$_{31}$N$_5$O).

EXAMPLE 37

N$^1$-[4-(4-Amino-1H-imidazo[4,5-c]quinolin-1-yl)butyl]-(trans)-2-phenylcyclopropane-1-carboxamide

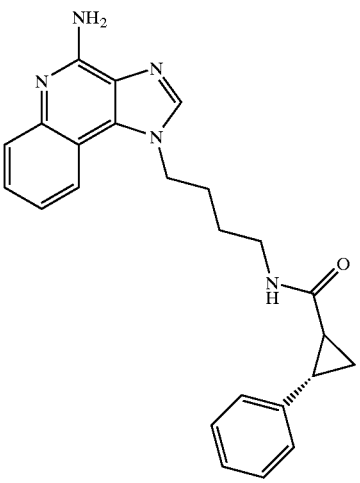

According to the general method of Example 14, 1-(4-aminobutyl)-1H-imidazo[4,5-c]quinolin-4-amine and trans-2-phenyl-1-cyclopropanecarbonyl chloride were combined to provide N$^1$-[4-(4-amino-1H-imidazo[4,5-c]quinolin-1-yl)butyl]-(trans)-2-phenylcyclopropane-1-carboxamide as an off white solid, m.p. 77.0° C. $^1$H NMR (300 MHz, DMSO-d$_6$) δ7.90 (dd, J=8.1, 1.2 Hz, 1H), 7.81 (dd, J=8.1, 1.2 Hz, 1H), 7.78 (s, 1H), 7.50 (dt, J=8.1, 1.5 Hz, 1H), 7.33–7.15 (m, 4H), 7.05–7.02 (m, 2H), 5.84 (broad s, 1H), 5.51 (s, 2H), 4.52 (t, J=7.2 Hz, 2H), 3.32 (q, J=6.6 Hz, 2H), 2.49–2.43 (m, 1H), 2.07–1.95 (m, 3H), 1.64–1.51 (m, 3H), 1.25–1.18 (m, 1H); IR (KBr) 3304, 3179, 2939, 1640, 1582, 1527, 1479, 1396, 1250, 755, 735, 689 cm$^{-1}$; MS (EI) m/e 399.2059 (399.2059 calcd for C$_{24}$H$_{25}$N$_5$O).

EXAMPLE 38

N$^1$-[4-(4-Amino-1H-imidazo[4,5-c]quinolin-1-yl)butyl]-1-naphthamide

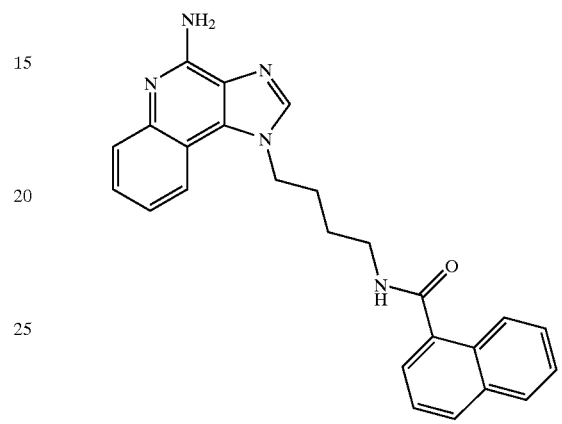

According to the general method of Example 14, 1-(4-aminobutyl)-1H-imidazo[4,5-c]quinolin-4-amine and 1-naphthoyl chloride were combined to provide N$^1$-[4-(4-amino-1H-imidazo[4,5-c]quinolin-1-yl)butyl]-1-naphthamide as an off white powder, m.p. 174.5° C. (decomposition). $^1$H NMR (300 MHz, DMSO-d$_6$) δ8.52 (t, J=5.6 Hz, 1H), 8.49 (s, 1H), 8.24 (m, 3H), 8.10 (d, J=8.1 Hz, 1H), 7.97 (m, 2H), 7.80 (d, J=8.2 Hz, 1H), 7.65 (t, J=7.3 Hz, 1H), 7.57–7.41 (m, 5H), 4.75 (t, J=6.9 Hz, 2H), 2.03–1.98 (m, 2H), 1.69–1.64 (m, 2H); MS (EI) m/e 409.1903 (409.1903 calcd for C$_{25}$H$_{23}$N$_5$O).

EXAMPLE 39

N$^1$-[4-(4-Amino-1H-imidazo[4,5-c]quinolin-1-yl)butyl]-3-phenoxybenzamide

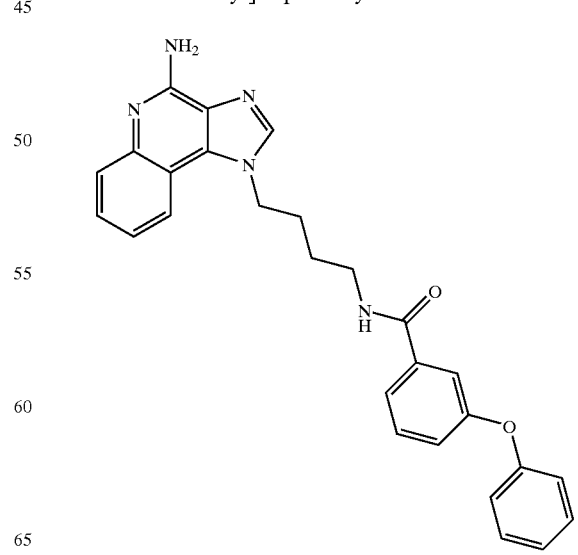

According to the general method of Example 14, 1-(4-aminobutyl)-1H-imidazo[4,5-c]quinolin-4-amine and 3-phenoxybenzoyl chloride were combined to provide $N^1$-[4-(4-amino-1H-imidazo[4,5-c]quinolin-1-yl)butyl]-3-phenoxybenzamide as a white powder, m.p. 105.0–107.0° C. $^1$H NMR (300 MHz, DMSO-$d_6$) δ 8.54 (t, J=5.4 Hz, 1H), 8.34 (s, 1H), 8.10 (d, J=8.1 Hz, 1H), 7.69 (dd, J=8.1, 1.2 Hz, 1H), 7.58–7.29 (m, 9H), 7.19–7.13 (m, 2H), 7.04–6.99 (m, 2H), 4.65 (t, J=7.2 Hz, 2H), 3.28 (m, 2H), 1.89 (quintet, J=7.2 Hz, 2H), 1.58 (quintet, J=7.2 Hz, 2H); MS (EI) m/e 451.2012 (451.2008 calcd for $C_{27}H_{25}N_5O_2$).

EXAMPLE 40

$N^3$-[4-(4-Amino-1H-imidazo[4,5-c]quinolin-1-yl)butyl]-3-quinolinecarboxamide

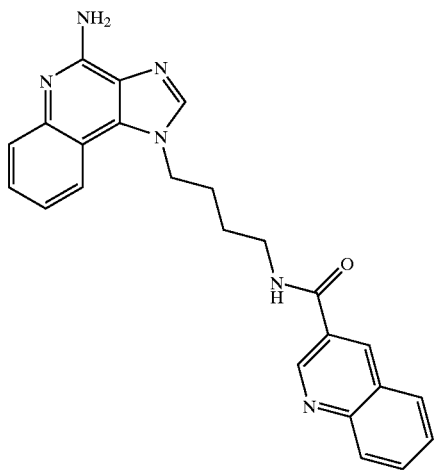

According to the general method of Example 14, 1-(4-arninobutyl)-1H-imidazo[4,5-c]quinolin-4-amine and quinoline-3-carbonyl chloride were combined to provide $N^3$-[4-(4-amino-1H-imidazo[4,5-c]quinolin-1-yl)butyl]-3-quinolinecarboxamide as a white crystalline solid, m.p. 116.0–118.0° C. (decomposition). $^1$H NMR (300 MHz, DMSO-$d_6$) δ 9.24 (d, J=2.1 Hz, 1H), 8.86 (t, J=5.1 Hz, 1H), 8.74 (d, J=2.1 Hz, 1H), 8.25 (s, 1H), 8.09–8.05 (m, 3H), 7.86 (dt, J=7.5, 1.0 Hz, 1H), 7.69 (t, J=7.5 Hz, 1H), 7.61 (d, J=7.5 Hz, 1H), 7.40 (t, J=7.5 Hz, 1H), 7.21 (t, J=7.5 Hz, 1H), 6.68 (s, 2H), 4.67 (t, J=6.9 Hz, 2H), 1.97 (quintet, J=7.2 Hz, 2H), 1.65 (quintet, J=7.2 Hz, 2H); MS (EI) m/e 410.1864 (410.1855 calcd for $C_{24}H_{22}N_6O$).

EXAMPLE 41

$N^1$-[4-(4-Amino-1H-imidazo [4,5-c]quinolin-1-yl)butyl]-2-phenoxypropanamide

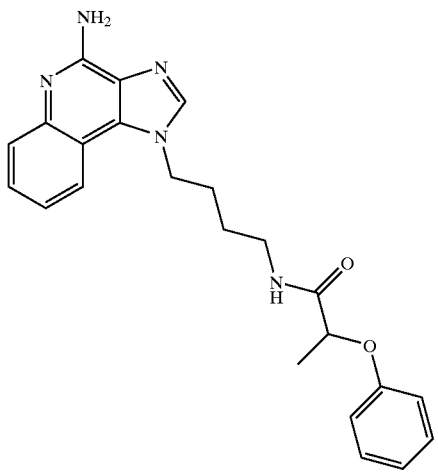

According to the general method of Example 14, 1-(4-aminobutyl)-1H-imidazo[4,5-c]quinolin-4-amine and 2-phenoxypropionyl chloride were combined to provide $N^1$-[4-(4-amino-1H-imidazo[4,5-c]quinolin-1-yl)butyl]-2-phenoxypropanamide as a white powder, m.p. 85.0–87.5° C. $^1$H NMR (300 MHz, DMSO-$d_6$) δ 8.15 (s, 1H), 8.07 (t, J=6.0 Hz, 1H), 8.00 (d, J=8.4 Hz, 1H), 7.62 (dd, J=8.4, 1.2 Hz, 1H), 7.43 (dt, J=7.5, 1.2 Hz, 1H), 7.28–7.16 (m, 3H), 6.91–6.81 (m, 3H), 6.57 (s, 2H), 4.62–4.53 (m, 3H), 3.10 (q, J=6.9 Hz, 2H), 1.76 (quintet, J=7.1 Hz, 2H), 1.43 (quintet, J=7.1 Hz, 2H), 1.33 (d, J=6.6 Hz, 3H); MS (EI) m/e 403.2005 (403.2008 calcd for $C_{23}H_{25}N_5O_2$).

EXAMPLE 42

$N^3$-[4-(4-Amino-1H-imidazo[4,5-c]quinolin-1-yl)butyl]-1-benzyl-1H-3-indolecarboxamide

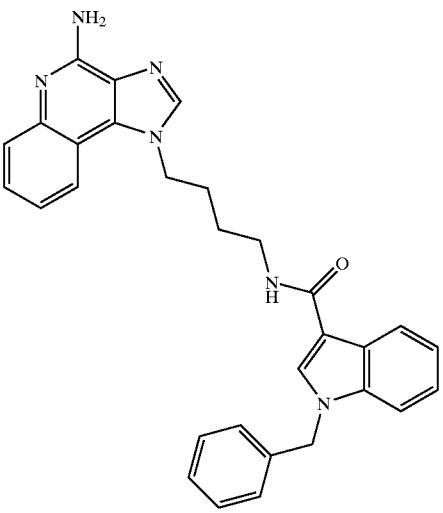

According to the general method of Example 14, 1-(4-aminobutyl)-1H-imidazo[4,5-c]quinolin-4-amine and 1-benzylindole-3-carbonyl chloride were combined to provide $N^3$-[4-(4-amino-1H-imidazo[4,5-c]quinolin-1-yl)butyl]-1-benzyl-1H-3-indolecarboxamide as a white powder, m.p. 139.0° C. (decomposition). $^1$H NMR (300 MHz, DMSO-$d_6$) δ8.24 (s, 1H), 8.14 (t, J=7.8 Hz, 1H), 8.04 (m, 2H), 7.93 (m, 1H), 7.62 (d, J=8.4 Hz, 1H), 7.51 (d, J=7.8 Hz, 1H), 7.44–7.09 (m, 9H), 6.63 (s, 2H), 5.44 (s, 2H), 4.66 (t, J=6.6 Hz, 2H), 1.97–1.92 (m, 2H), 1.62–1.57 (m, 2H); MS (EI) m/e 488.2326 (488.2325 calcd for $C_{30}H_{28}N_6O$).

EXAMPLE 43
$N^2$-[4-(4-Amino-1H-imidazo[4,5-c]quinolin-1-yl)butyl]-2-naphthamide

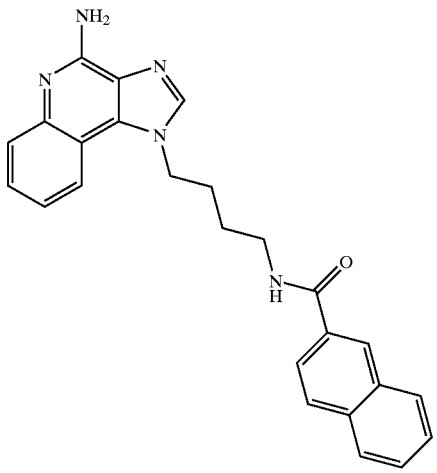

According to the general method of Example 14, 1-(4-aminobutyl)-1H-imidazo[4,5-c]quinolin-4-amine and 2-naphthoyl chloride were combined to provide $N^2$-[4-(4-amino-1H-imidazo[4,5-c]quinolin-1-yl)butyl]-2-naphthamide as a white powder, m.p. 257.0° C. (decomposition). $^1$H NMR (300 MHz, DMSO-$d_6$) δ8.85 (broad s, 2H), 8.69 (broad s, 1H), 8.57 (s, 1H), 8.38 (s, 1H), 8.25 (d, J=8.4 Hz, 1H), 7.99–7.80 (m, 5H), 7.75–7.50 (m, 4H), 4.75 (t, J=6.9 Hz, 2H), 3.39 (m, 2H), 1.98 (quintet, J=7.2 Hz, 2H), 1.68 (quintet, J=7.2 Hz, 2H); MS (EI) m/e 409.1909 (409.1903 calcd for $C_{25}H_{23}N_5O$).

EXAMPLE 44
$N^3$-[4-(4-Amino-1H-imidazo[4,5-c]quinolin-1-yl)butyl]-2,6-dimethoxynicotinamide

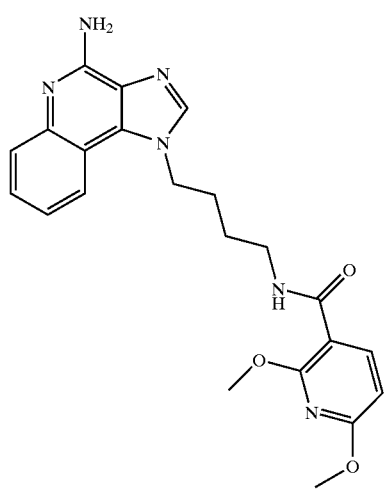

According to the general method of Example 14, 1-(4-aminobutyl)-1H-imidazo[4,5-c]quinolin-4-amine and 2,6-dimethoxynicotinoyl chloride were combined to provide $N^3$-[4-(4-amino-1H-imidazo[4,5-c]quinolin-1-yl)butyl]-2,6-dimethoxynicotinamide as an off white powder, m.p. 175.0–177.0° C. $^1$H NMR (300 MHz, DMSO-$d_6$) 8.21 (s, 1H), 8.11–8.02 (m, 3H), 7.62 (d, J=8.2 Hz, 1H), 7.42 (t, J=7.5 Hz, 1H), 7.20 (t, J=7.5 Hz, 1H), 6.58 (broad s, 2H), 6.46 (d, J=8.3 Hz, 1H), 4.63 (t, J=7.0 Hz, 2H), 3.90 (s, 3H), 3.88 (s, 3H), 3.30 (m, 2H), 1.90 (m, 2H), 1.57 (m, 2H); MS (EI) m/e 420.1909 (420.1910 calcd for $C_{22}H_{24}N_6O_3$).

EXAMPLE 45
$N^8$-[4-(4-Amino-1H-imidazo[4,5-c]quinolin-1-yl)butyl]-8-quinolinecarboxamide

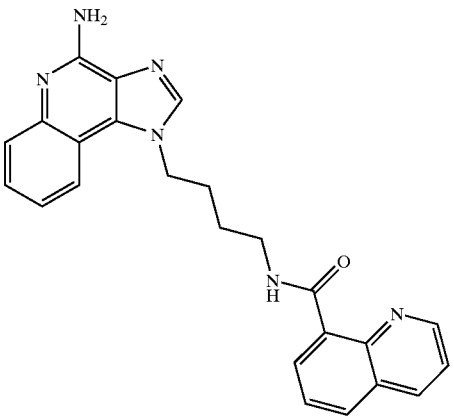

According to the general method of Example 14, 1-(4-aminobutyl)-1H-imidazo[4,5-c]quinolin-4-amine and quinoline-8-carbonyl chloride were combined to provide $N^8$-[4-(4-amino-1H-imidazo[4,5-c]quinolin-1-yl)butyl]-8-quinolinecarboxamide as a tan powder, m.p. 91.0–93.0° C. $^1$H NMR (300 MHz, DMSO-$d_6$) δ10.80 (t, J=5.5 Hz, 1H), 8.79 (dd, J=4.3, 1.8 Hz, 1H), 8.55–8.49 (m, 2H), 8.24 (s, 1H), 8.17 (dd, J=8.1, 1.5 Hz, 1H), 8.06 (d, J=7.2 Hz, 1H), 7.73 (t, J=7.8 Hz, 1H), 7.63–7.59 (m, 2H), 7.40 (dt J=7.1, 1.2 Hz, 1H), 7.14 (dt, J=7.1, 1.2 Hz, 1H), 6.57 (broad s, 2H), 4.68 (t, J=7.0 Hz, 2H), 3.51 (m, 2H), 2.02 (m, 2H), 1.69 (m, 2H); MS (EI) m/e 410.1858 (410.1855 calcd for $C_{24}H_{22}N_6O$).

EXAMPLE 46
$N^1$-[4-(4-Amino-1H-imidazo[4,5-c]quinolin-1-yl)butyl]-2-(4-isobutylphenyl)propanamide

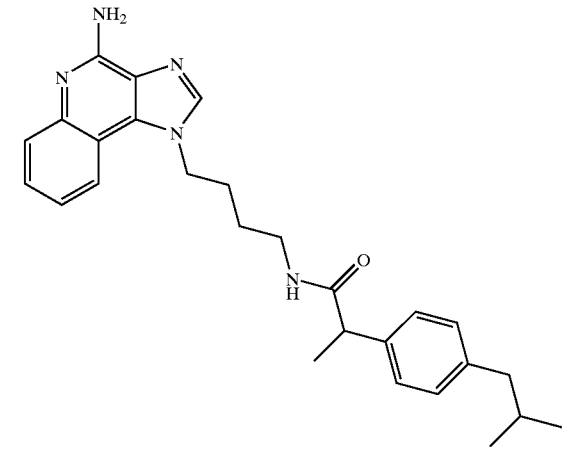

According to the general method of Example 14, 1-(4-aminobutyl)-1H-imidazo[4,5-c]quinolin-4-amine and 4-isobutyl-α-methylphenylacetyl chloride were combined to provide $N^1$-[4-(4-amino-1H-imidazo[4,5-c]quinolin-1-yl)butyl]-2-(4-isobutylphenyl)propanamide as a white powder, m.p. 172.0–173.0° C. $^1$H NMR (300 MHz, DMSO-$d_6$) δ 8.14 (s, 1H), 8.01 (d, J=7.6 Hz, 1H), 7.90 (t, J=5.6 Hz, 1H), 7.63 (dd, J=8.1, 1.0 Hz, 1H), 7.44 (dt, J=7.0, 1.0 Hz, 1H), 7.25 (dt, J=7.0 Hz, 1H), 7.14 (d, J=8.0 Hz, 2H), 6.97 (d, J=8.0 Hz, 2H), 6.58 (broad s, 2H), 4.55 (t, J=7.0 Hz, 2H), 3.47 (q, J=7.1 Hz, 1H), 3.06 (m, 2H), 2.34 (d, J=7.1 Hz, 2H), 1.80–1.69 (m, 3H), 1.44 (m, 2H), 1.24 (d, J=7.0 Hz, 3H), 0.82 (d, J=6.6 Hz, 6H); MS (EI) m/e 443.2687 (443.2685 calcd for $C_{27}H_{33}N_5O$).

EXAMPLE 47

$N^3$-[4-(4-Amino-1H-imidazo[4,5-c]quinolin-1-yl)butyl]nicotinamide

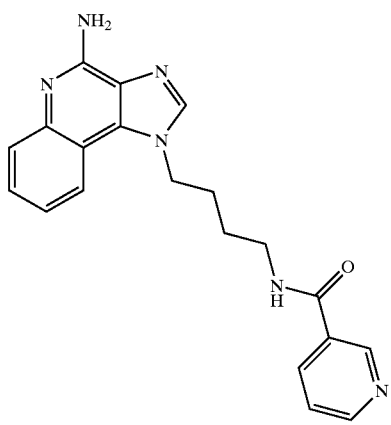

According to the general method of Example 14, 1-(4-aminobutyl)-1H-imidazo[4,5-c]quinolin-4-amine and nicotinoyl chloride hydrochloride were combined to provide $N^3$-[4-(4-amino-1H-imidazo[4,5-c]quinolin-1-yl)butyl]nicotinamide as a white powder, m.p. 188.6–189.5° C. $^1$H NMR (300 MHz, DMSO-$d_6$) δ 8.95 (dd, J=2.2, 0.7 Hz, 1H), 8.70–8.65 (m, 2H), 8.22 (s, 1H), 8.11 (dt, J=8.3, 2.0 Hz, 1H), 8.04 (dd, J=8.2, 0.9 Hz, 1H), 7.61 (dd, J=8.3, 1.1 Hz, 1H), 7.50–7.39 (m, 2H), 7.23–7.18 (m, 1H), 6.58 (broad s, 2H), 4.64 (t, J=7.0 Hz, 2H), 3.30 (m, 2H), 1.93 (m, 2H), 1.60 (m, 2H); MS (EI) m/e 360.1696 (360.1699 calcd for $C_{20}H_{20}N_6O$).

EXAMPLE 48

$N^4$-[4-(4-Amino-1H-imidazo[4,5-c]quinolin-1-yl)butyl]isonicotinamide

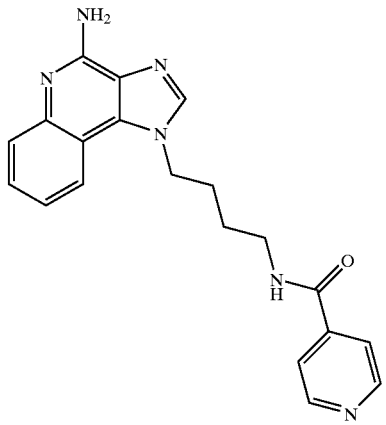

According to the general method of Example 14, 1-(4-aminobutyl)-1H-imidazo[4,5-c]quinolin-4-amine and isonicotinoyl chloride hydrochloride were combined to provide $N^4$-[4-(4-amino-1H-imidazo[4,5-c]quinolin-1-yl)butyl]isonicotinamide as a white crystalline solid, m.p. 213.0–213.7° C. $^1$H NMR (300 MHz, DMSO-$d_6$) δ 8.76 (m, 1H), 8.69 (d, J=5.6 Hz, 2H), 8.22 (s, 1H), 8.04 (d, J=8.0 Hz, 1H), 7.67 (d, J=5.7 Hz, 2H), 7.62 (d, J=8.2 Hz, 1H), 7.43 (t, J=7.5 Hz, 1H), 7.21 (t, J=7.5 Hz, 1H), 6.62 (broad s, 2H), 4.64 (t, J=6.8 Hz, 2H), 3.30 (m, 2H), 1.92 (m, 2H), 1.58 (m, 2H); MS (EI) m/e 360.1699 (360.1699 calcd for $C_{20}H_{20}N_6O$).

EXAMPLE 49

$N^4$-[4-(4-Amino-1H-imidazo[4,5-c]quinolin-1-yl)butyl]-4-quinolinecarboxamide

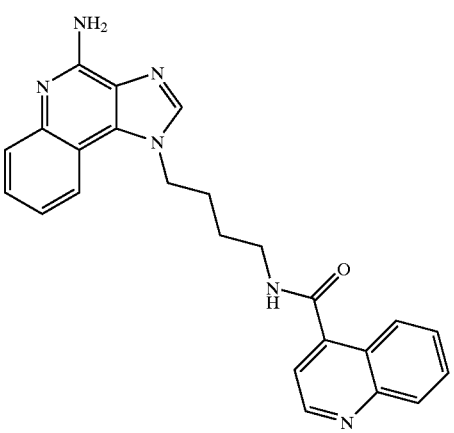

According to the general method of Example 14, 1-(4-aminobutyl)-1H-imidazo[4,5-c]quinolin-4-amine and quinoline-4-carbonyl chloride were combined to provide N4-[4-(4-amino-1H-imidazo[4,5-c]quinolin-1-yl)butyl]-4-quinolinecarboxamide as a white crystalline solid, m.p. 214.5–215.2° C. $^1$H NMR (300 MHz, DMSO-$d_6$) δ8.89 (d, J=4.3 Hz, 1H), 8.76 (t, J=5.6 Hz, 1H), 8.24 (s, 1H), 8.10–8.01 (m, 3H), 7.78 (ddd, J=8.4, 6.9, 1.5 Hz, 1H), 7.64 (dd, J=8.4, 1.1 Hz, 1H), 7.56 (ddd, J=8.3, 6.9, 1.4 Hz, 1H), 7.44 (ddd, J=8.3, 7.0, 1.3 Hz, 1H), 7.34 (d, J=4.3 Hz, 1H), 7.24 (ddd, J=8.3, 7.0, 1.3 Hz, 1H), 6.60 (broad s, 2H), 4.68 (t, J=6.9 Hz, 2H), 3.38 (q, J=7.0 Hz, 2H), 2.00 (m, 2H), 1.63 (m, 2H); MS (EI) m/e 410.1860 (410.1855 calcd for $C_{24}H_{22}N_6O$).

EXAMPLE 50

N4-[4-(4-Amino-2-(2-methoxyethyl)-1H-imidazo[4,5-c]quinolin-1-yl)butyl]-2-phenyl-4-quinolinecarboxamide

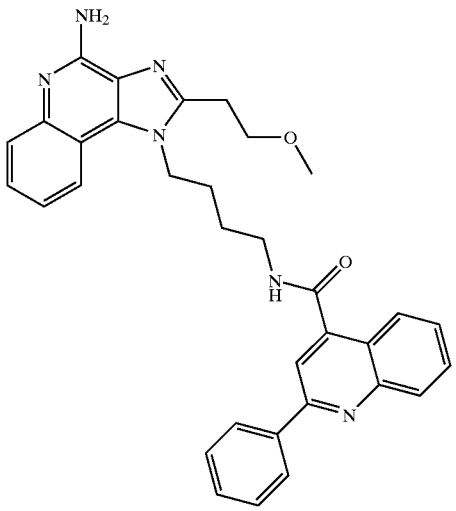

1-[3-(Dimethylamino)propyl]-3-ethylcarbodiimide hydrochloride (0.57 g, 3.0 mmol) was added dropwise to a chilled (0° C.) solution of 2-phenyl-4-quinolinecarboxylic acid (0.5 g, 3.7 mmol), 1-hydroxybenzotriazole (0.5 g, 3.7 mmol), pyridine (2.2 ml), and dichloromethane (20 ml). The reaction was maintained for 15 min followed by the dropwise addition of 1-(4-aminobutyl)-2-(2-methoxyethyl)-1H-imidazo[4,5-c]quinolin-4-amine (0.8 g, 2.55 mmol) in dichloromethane (100 ml). The reaction was maintained at room temperature overnight. The solvent was removed in vacuo and the residue was purified by flash column chromatography (silica gel, 9:1 dichloromethane:methanol). The fractions containing product were combined, washed with saturated aqueous sodium bicarbonate, dried (MgSO$_4$), filtered, and concentrated to provide 0.62 g of N4-[4-(4-amino-2-(2-methoxyethyl)-1H-imidazo[4,5-c]quinolin-1-yl)butyl]-2-phenyl-4-quinolinecarboxamide as a yellow crystalline solid, m.p. 118° C. (decomposition). $^1$H NMR (300 MHz, DMSO-$d_6$) δ8.88 (t, J=5.7 Hz, 1H), 8.24–8.21 (m, 2H), 8.13–8.01(m, 4H), 7.83–7.78 (m, 1H), 7.62–7.48 (m, 5H), 7.36 (m, 1H), 7.20 (dt, J=7.6, 1.2 Hz, 1H), 6.54 (broad s, 2H), 4.62 (t, J=7.2 Hz, 2H), 3.83 (t, J=6.7 Hz, 2H), 3.45 (m, 2H), 3.29–3.20 (m, 5H), 1.96 (m, 2H), 1.79 (m, 2H); MS (EI) m/e 544.2589 (544.2587 calcd for $C_{33}H_{32}N_6O_2$)

EXAMPLE 51

N3-[4-(4-Amino-1H-imidazo[4,5-c]quinolin-1-yl)butyl]-2-(pentylsulfanyl)nicotinamide

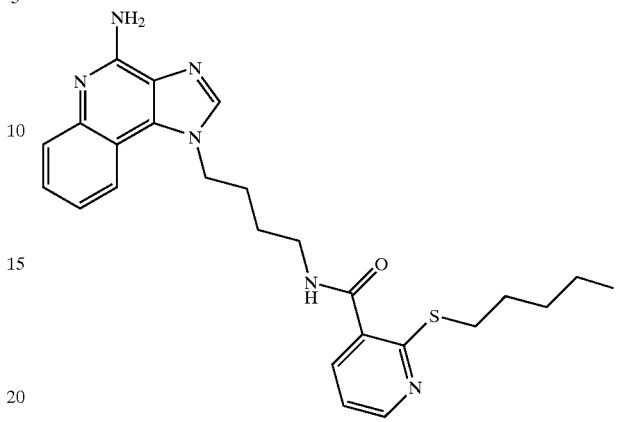

According to the general method of Example 14, 1-(4-aminobutyl)-1H-imidazo[4,5-c]quinolin-4-amine and 2-(n-pentylthio)pyridine-3-carbonyl chloride were combined to provide N3-[4-(4-amino-1H-imidazo[4,5-c]quinolin-1-yl)butyl]-2-(pentylsulfanyl)nicotinamide as a tan powder, m.p. 158.0–161.0° C. $^1$H NMR (300 MHz, DMSO-$d_6$) δ8.47–8.41 (m, 2H), 8.21 (s, 1H), 8.06 (d, J=8.2 Hz, 1H), 7.63 (dd, J=8.3, 1.1 Hz, 1H), 7.54 (dd, J=7.6, 1.8 Hz, 1H), 7.47–7.41 (m, 1H), 7.26–7.21 (m, 1H), 7.08 (dd, J=7.5, 4.8 Hz, 1H), 6.57 (broad s, 2H), 4.64 (t, J=6.9 Hz, 2H), 3.27 (m, 2H), 2.98 (t, J=7.3 Hz, 2H), 1.96 (m, 2H), 1.62–1.46 (m, 4H), 1.35–1.20 (m, 4H), 0.83 (t, J=7.1 Hz, 3H); MS (EI) m/e 462.2196 (462.2202 calcd for $C_{25}H_{30}N_6OS$).

EXAMPLE 52

N3-[4-(4-Amino-1H-imidazo[4,5-c]quinolin-1-yl)butyl]-6-cyanonicotinamide

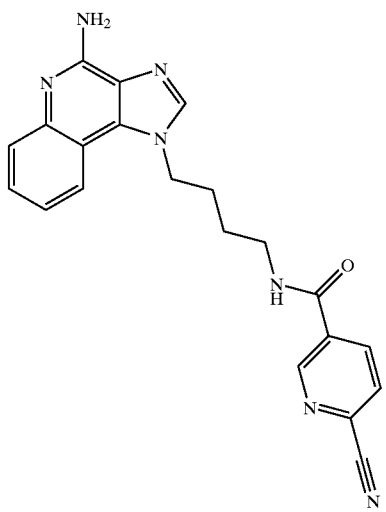

According to the general method of Example 14, 1-(4-aminobutyl)-1H-imidazo[4,5-c]quinolin-4-amine and 6-cyanopyridine-3-carbonyl chloride were combined to provide N3-[4-(4-amino-1H-imidazo[4,5-c]quinolin-1-yl)butyl]-6-cyanonicotinamide as an off white powder, m.p.

125.0–129.0° C. $^1$H NMR (300 MHz, DMSO-$d_6$) δ9.05 (dd, J=2.1, 0.8 Hz, 1H), 8.88 (t, J=5.6 Hz, 1H), 8.31 (dd, J=8.1, 2.1 Hz, 1H), 8.21 (s, 1H), 8.14 (dd, J=8.1, 0.8 Hz, 1H), 8.03 (m, 1H), 7.62 (dd, J=8.3, 1.1 Hz, 1H), 7.42 (m, 1H), 7.20 (m, 1H), 6.59 (broad s, 2H), 4.64 (t, J=6.9 Hz, 2H), 3.30 (m, 2H), 1.93 (m, 2H), 1.59 (m, 2H); MS (EI) m/e 385.1648 (385.1651 calcd for $C_{21}H_{19}N_7O$).

EXAMPLE 53
N$^3$-[4-(4-Amino-1H-imidazo[4,5-c]quinolin-1-yl) butyl]-6-chloronicotinamide

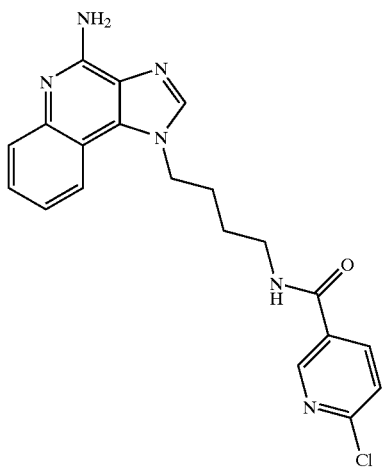

According to the general method of Example 14, 1-(4-aminobutyl)-1H-imidazo[4,5-c]quinolin-4-amine and 6-chloropyridine-3-carbonyl chloride were combined to provide N$^3$-[4-(4-amino-1H-imidazo[4,5-c]quinolin-1-yl)butyl]-6-chloronicotinamide as an off white crystalline solid, m.p. 144.0–148.0° C. (decomposition). $^1$H NMR (300 MHz, DMSO-$d_6$) δ8.77 (dd, J=2.5, 0.6 Hz, 1H), 8.73 (t, J=5.6 Hz, 1H), 8.22 (s, 1H), 8.16 (dd, J=8.3, 2.5 Hz, 1H), 8.03 (m, 1H), 7.63 (d, J=0.5 Hz, 1H), 7.60 (d, J=0.5 Hz, 1H), 7.45– 7.40 (m, 1H), 7.23–7.18 (m, 1H), 6.61 (broad s, 2H), 4.63 (t, J=6.9 Hz, 2H), 3.30 (m, 2H), 1.92 (m, 2H), 1.58 (m, 2H). MS (EI) m/e 394.1298 (394.1309 calcd for $C_{20}H_{19}N_6OCl$).

EXAMPLE 54
N$^3$-[4-(4-Amino-1H-imidazo[4,5-c]quinolin-1-yl) butyl]-6-(2,2,2-trifluoroethoxy)nicotinamide

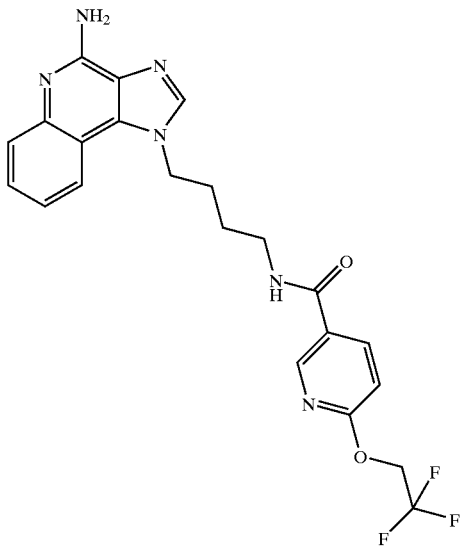

According to the general method of Example 14, 1-(4-aminobutyl)-1H-imidazo[4,5-c]quinolin-4-amine and 6-(2,2,2-trifluoroethoxy)pyridine-3-carbonyl chloride were combined to provide N$^3$-[4-(4-amino-1H-imidazo[4,5-c] quinolin-1-yl)butyl]-6-(2,2,2-trifluoroethoxy)nicotinamide as a white crystalline solid, m.p. 192.0–194.0° C. (decomposition). $^1$H NMR (300 MHz, DMSO-$d_6$) δ8.62 (d, J=1.9 Hz, 1H), 8.58 (t, J=5.6 Hz, 1H), 8.25 (s, 1H), 8.15 (dd, J=8.6, 2.4 Hz, 1H), 8.06 (d, J=7.6 Hz, 1H), 7.64 (d, J=7.8 Hz, 1H), 7.45 (t, J=7.1 Hz, 1H), 7.24 (t, J=7.1 Hz, 1H), 7.04 (d, J=8.6 Hz, 1H), 6.82 (broad s, 2H), 5.06 (q, J=9.1 Hz, 2H), 4.64 (t, J=6.9 Hz, 2H), 3.30 (m, 2H), 1.91 (m, 2H), 1.60 (m, 2H); MS (EI) m/e 458.1678 (458.1678 calcd for $C_{22}H_{21}N_6O_2F_3$).

EXAMPLE 55
N$^2$-{4-[4-Amino-2-(2-methoxyethyl)-1H-imidazo[4,5-c]quinolin-1-yl]butyl}-2-quinolinecarboxamide

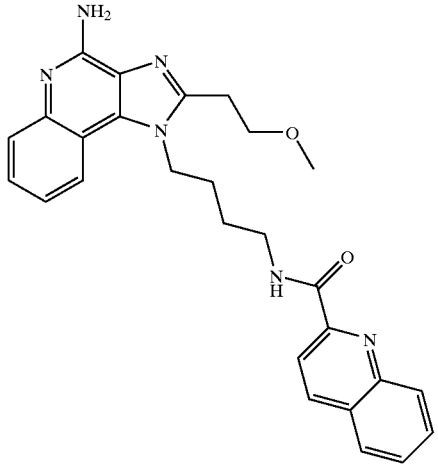

According to the general method of Example 14, 1-(4-aminobutyl)-2-(2-methoxyethyl)-1H-imidazo[4,5-c] quinolin-4-amine and quinoline-2-carbonyl chloride were combined in dichloromethane and triethylamine (3 equivalents) to provide N$^2$-{4-[4-amino-2-(2-methoxyethyl)-1H-imidazo[4,5-c]quinolin-1-yl]butyl}-2-quinolinecarboxamide as a white solid, m.p. 78.1–79.9° C. $^1$H NMR (300 MHz, DMSO-$d_6$) δ9.02 (t, J=6.1 Hz, 1H), 8.55 (d, J=8.5 Hz, 1H), 8.23 (d, J=8.5 Hz, 1H), 8.10 (t, J=7.6 Hz, 1H), 8.02 (d, J=7.6 Hz, 1H), 7.90–7.84 (m, 1H), 7.75–7.70 (m, 1H), 7.58 (dd, J=8.3, 1.0 Hz, 1H), 7.35–7.30 (m, 1H), 7.18–7.13 (m, 2H), 6.48 (broad s, 2H), 4.58 (m, 2H), 3.79 (t, J=6.7 Hz, 2H), 3.44 (m, 2H), 3.22 (m, 5H), 1.91–1.78 (m, 4H); MS (EI) m/e 468.2276 (468.2274 calcd for $C_{27}H_{28}N_6O_2$).

EXAMPLE 56
N¹-[4-(4-Amino-1H-imidazo[4,5-c]quinolin-1-yl)butyl]-2-(2-fluoro-4-biphenylyl)propanamide

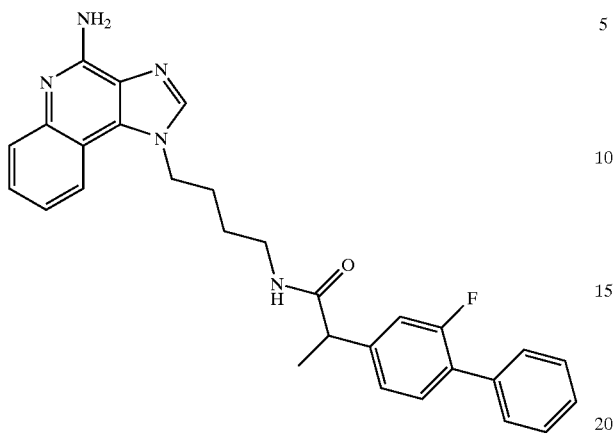

According to the general method of Example 14, 1-(4-aminobutyl)-2-(2-methoxyethyl)-1H-imidazo[4,5-c]quinolin-4-amine and 2-(2-fluoro-4-biphenylyl)propionyl chloride were combined to provide N¹-[4-(4-amino-1H-imidazo[4,5-c]quinolin-1-yl)butyl]-2-(2-fluoro-4-biphenylyl)propanamide as a white powder, m.p. 76.1–79.9° C. ¹H NMR (300 MHz, DMSO-$d_6$) δ8.17 (s, 1H), 8.03 (m, 2H), 7.62 (d, J=8.3 Hz, 1H), 7.49–7.14 (m, 10H), 6.59 (broad s, 2H), 4.58 (t, J=6.9 Hz, 2H), 3.59 (q, J=7.0 Hz, 1H), 3.09 (pentet, J=6.7 Hz, 2H), 1.82 (m, 2H), 1.45 (m, 2H), 1.30 (d, J=7.0 Hz, 3H); MS (EI) m/e 481.2268 (481.2278 calcd for $C_{29}H_{28}FN_5O$).

EXAMPLE 57
N¹-{4-[4-Amino-2-(2-methoxyethyl)-1H-imidazo[4,5-c]quinolin-1-yl]butyl}-1-isoquinolinecarboxamide

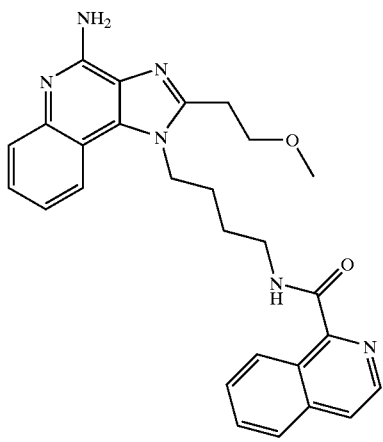

According to the general method of Example 50, 1-(4-aminobutyl)-2-(2-methoxyethyl)-1H-imidazo[4,5-c]quinolin-4-amine and isoquinoline-1-carboxylic acid were combined to provide N¹-{4-[4-amino-2-(2-methoxyethyl)-1H-imidazo[4,5-c]quinolin-1-yl]butyl}-1-isoquinolinecarboxamide as a yellow crystalline solid, m.p. 61.0–63.0° C. ¹H NMR (300 MHz, DMSO-$d_6$) δ8.94 (t, J=5.9 Hz, 1H), 8.87 (d, J=8.5 Hz, 1H), 8.51 (d, J=5.6 Hz, 1H), 8.05–7.96 (m, 3H), 7.84–7.96 (m, 1H), 7.70–7.65 (m, 1H), 7.61 (dd, J=8.3, 1.1 Hz, 1H), 7.37 (dt, J=7.7, 1.0 Hz, 1H), 7.19 (dt, J=7.6, 1.2 Hz, 1H), 6.53 (broad s, 2H), 4.60 (t, J=7.2 Hz, 2H), 3.81 (t, J=6.7 Hz, 2H), 3.41 (m, 2H), 3.28–3.12 (m, 5H), 1.92–1.76 (m, 4H); MS (EI) m/e 468.2261 (468.2274 calcd for $C_{27}H_{28}N_6O_2$).

EXAMPLE 58
N²-{4-[4-Amino-2-(2-methoxyethyl)-1H-imidazo[4,5-c]quinolin-1-yl]butyl}-5-butyl-2-pyridinecarboxamide

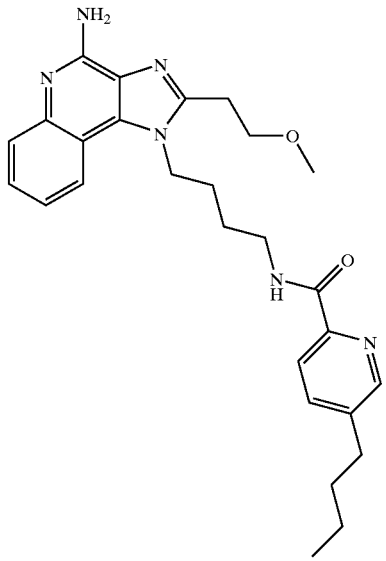

According to the general method of Example 50, 1-(4-aminobutyl)-2-(2-methoxyethyl)-1H-imidazo[4,5-c]quinolin-4-amine and fusaric acid were combined to provide N²-{4-[4-amino-2-(2-methoxyethyl)-1H-imidazo[4,5-c]quinolin-1-yl]butyl}-5-butyl-2-pyridinecarboxamide as a tan solid, m.p. 54.9–55.2° C. ¹H NMR (300 MHz, DMSO-$d_6$) δ8.81 (t, J=6.1 Hz, 1H), 8.44 (m, 1H), 7.98 (d, J=7.3 Hz, 1H), 7.94 (dd, J=8.0, 0.7 Hz, 1H), 7.80 (dd, J=8.0, 2.2 Hz, 1H), 7.60 (dd, J=8.3, 1.2 Hz, 1H), 7.39–7.34 (m, 1H), 7.16–7.10 (m, 1H), 6.52 (broad s, 2H), 4.55 (t, J=6.9 Hz, 2H), 3.79 (t, J=6.7 Hz, 2H), 3.23 (s, 3H), 3.18 (t, J=6.7 Hz, 2H), 2.67 (t, J=7.6 Hz, 2H), 1.83–1.72 (m, 4H), 1.63–1.53 (m, 2H), 1.34–1.24 (m, 2H), 0.90 (t, J=7.3 Hz, 3H); MS (EI) m/e 474.2750 (474.2743 calcd for $C_{27}H_{34}N_6O_2$).

EXAMPLE 59
N³-{4-[4-Amino-2-(2-methoxyethyl)-1H-imidazo[4,5-c]quinolin-1-yl]butyl}-3-indolecarboxamide

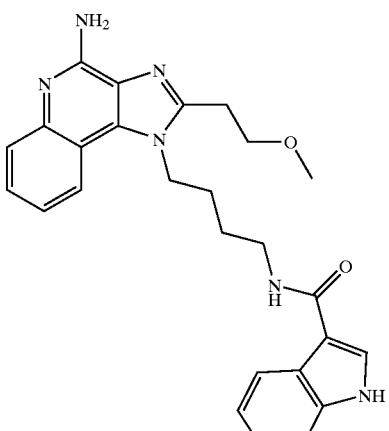

According to the general method of Example 50, 1-(4-aminobutyl)-2-(2-methoxyethyl)-1H-imidazo[4,5-c]quinolin-4-amine and indole-3-carboxylic acid were combined to provide N³-{4-[4-amino-2-(2-methoxyethyl)-1H-imidazo[4,5-c]quinolin-1-yl]butyl}-3-indolecarboxamide as a white powder, m.p. 225.5–227.4° C. ¹H NMR (300 MHz, DMSO-d₆) δ11.50 (broad s, 1H), 8.13 (d, J=7.9 Hz, 1H), 8.06 (d, J=10.2 Hz, 1H), 7.95–7.89 (m, 2H), 7.61 (d, J=8.3 Hz, 1H), 7.43–7.35 (m, 2H), 7.20–7.05 (m, 3H), 6.48 (broad s, 2H), 4.58 (t, J=7.2 Hz, 2H), 3.80 (t, J=6.6 Hz, 2H), 3.33 (m, 2H), 3.24–3.18 (m, 5H), 1.88 (m, 2H), 1.70 (m, 2H); ¹³C NMR (75 MHz, DMSO-d₆) δ165.0, 152.0, 151.0, 145.1, 136.4, 132.6, 127.8, 126.8, 126.6, 126.4, 122.1, 121.5, 121.4, 120.6, 120.3, 115.1, 112.1, 111.0, 70.5, 58.4, 45.1, 38.2, 27.7, 27.5, 27.0; MS (EI) m/e 456.2282 (456.2274 calcd for $C_{26}H_{28}N_6O_2$).

EXAMPLE 60

N¹-{4-[4-Amino-2-(2-methoxyethyl)-1H-imidazo[4,5-c]quinolin-1-yl]butyl}-4-(1-pyrrolyl)benzamide

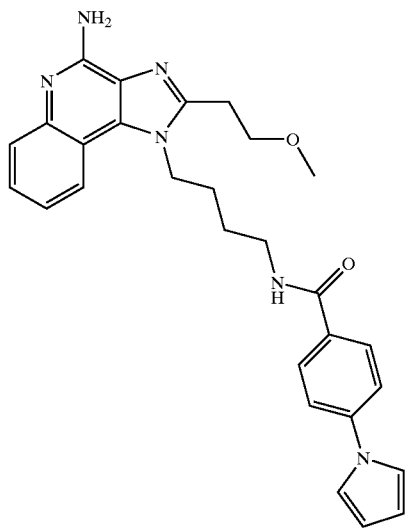

According to the general method of Example 50, 1-(4-aminobutyl)-2-(2-methoxyethyl)-1H-imidazo[4,5-c]quinolin-4-amine and 4-(1-pyrrolyl)benzoic acid were combined to provide N¹-{4-[4-amino-2-(2-methoxyethyl)-1H-imidazo[4,5-c]quinolin-1-yl]butyl}-4-(1-pyrrolyl)benzamide as an off white powder, m.p. 173.0–174.9° C. ¹H NMR (300 MHz, DMSO-d₆) δ8.52 (t, J=5.5 Hz, 1H), 8.02 (d, J=7.9 Hz, 1H), 7.90 (d, J=8.7 Hz, 2H), 7.67 (d, J=8.7 Hz, 2H), 7.61 (dd, J=8.4, 1.1 Hz, 1H), 7.48 (t, J=2.2 Hz, 2H), 7.39 (m, 1H), 7.19 (dt, J=7.6, 1.1 Hz, 1H), 6.53 (broad s, 2H), 6.30 (t, J=2.2 Hz, 2H), 4.57 (t, J=7.0 Hz, 2H), 3.82 (t, J=6.7 Hz, 2H), 3.33 (m, 2H), 3.26 (s, 3H), 3.20 (t, J=6.7 Hz, 2H), 1.87 (m, 2H), 1.71 (m, 2H); MS (EI) m/e 482.2421 (482.2430 calcd for $C_{28}H_{30}N_6O_2$).

EXAMPLE 61

N²-{4-[4-Amino-2-(4-methoxybenzyl)-1H-imidazo[4,5-c]quinolin-1-yl]butyl}-2-quinolinecarboxamide

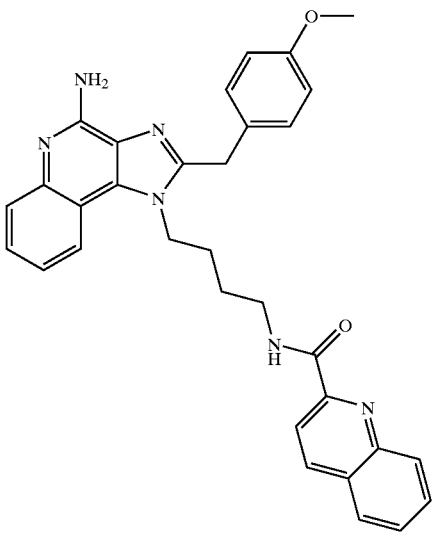

Quinoline-2-carbonyl chloride (0.28 g in 10 ml dichloromethane, 1.46 nmmol) was added dropwise to a stirring solution of 1-(4-aminobutyl)-2-(4-methoxybenzyl)-1H-imidazo[4,5-c]quinolin-4-amine (0.49 g, 1.3 mmol), dichloromethane (140 ml) and triethylamine (0.5 ml). The reaction was maintained for 17 hours and then concentrated in vacuo. The yellow residue was partitioned between dichloromethane and saturated aqueous sodium bicarbonate. The organic fraction was dried (MgSO₄), filtered, and concentrated. The crude residue was purified by flash column chromatography (silica gel, gradient elution using dichloromethane to 95:5 dichloromethanemethanol) to provide 0.19 g of N²-{4-[4-amino-2-(4-methoxybenzyl)-1H-imidazo[4,5-c]quinolin-1-yl]butyl}-2-quinolinecarboxamide as an off white solid, m.p. 95.1–97.4° C. ¹H NMR (300 MHz, DMSO-d₆) δ8.97 (t, J=6.0 Hz, 1H), 8.56 (d, J=8.4 Hz, 1H), 8.16–8.07 (m, 3H), 7.96 (d, J=7.7 Hz, 1H), 7.87 (m, 1H), 7.72 (m, 1H), 7.58 (dd, J=8.3, 1.1 Hz, 1H), 7.31 (m, 1H), 7.23 (d, J=8.7 Hz, 2H), 7.08 (m, 1H), 6.82 (d, J=8.7 Hz, 2H), 6.58 (broad s, 2H), 4.50 (m, 2H), 4.33 (s, 2H), 3.63 (s, 3H), 3.34 (m, 2H), 1.65 (m, 4H); MS (EI) m/e 530.2431 (530.2430 calcd for $C_{32}H_{30}N_6O_2$).

EXAMPLE 62

N³-{4-[4-Amino-2-(2-methoxyethyl)-1H-imidazo[4,5-c]quinolin-1-yl]butyl}-6-(1-pyrrolyl)nicotinamide

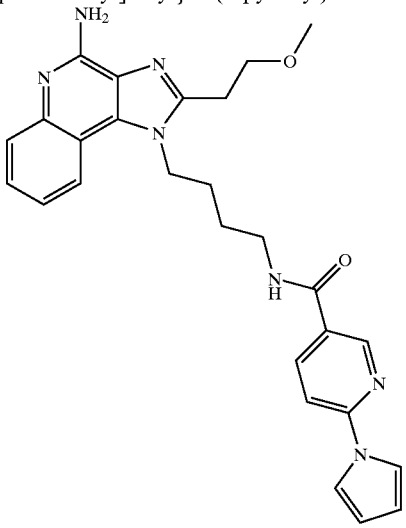

According to the general method of Example 50, 1-(4-aminobutyl)-2-(2-methoxyethyl)-1H-imidazo[4,5-c]quinolin-4-amine and 2-pyrrolopyridine-5-carboxylic acid were combined to provide $N^3${4-[4-amino-2-(2-methoxyethyl)-1H-imidazo[4,5-c]quinolin-1-yl]butyl}-6-(1-pyrcolyl)nicotinamide as a yellow crystalline solid, m.p. 77.0–80.0° C. $^1$H NMR (300 MHz, CDCl$_3$) 8.72 (d, J=2.3 Hz, 1H), 8.07 (dd, J=8.4, 2.4 Hz 1H), 7.92 (d, J=7.3 Hz, 1H), 7.82 (d, J=7.4 Hz, 1H), 7.55 (t, J=2.2 Hz, 2H), 7.49 (m, 1H), 7.37 (m, 2H), 6.39 (d, J=2.2 Hz, 2H), 6.20 (m, 1H), 5.42 (broad s, 2H), 4.59 (t, J=7.5 Hz, 2H), 3.90 (t, J=7.4 Hz, 2H), 3.56 (q, J=6.7 Hz, 2H), 3.36 (s, 3H), 3.20 (t, J=6.4 Hz, 2H), 2.05 (m, 2H), 1.82 (m, 2H); MS (EI) m/e 483.2376 (483.2383 calcd for C$_{27}$H$_{29}$N$_7$O$_2$).

EXAMPLE 63

$N^5$-{4-[4-Amino-2-(2-methoxyethyl)-1H-imidazo[4,5-c]quinolin-1-yl]butyl}-5-indolecarboxamide

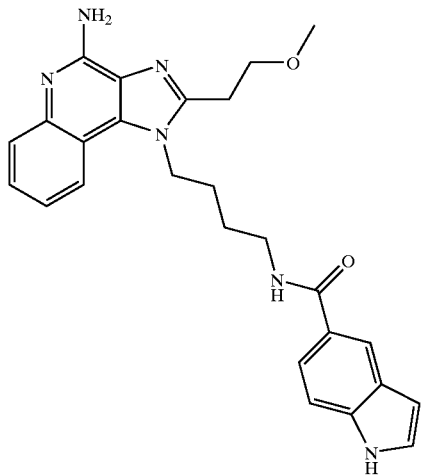

According to the general method of Example 50, 1-(4-aminobutyl)-2-(2-methoxyethyl)-1H-imidazo[4,5-c]quinolin-4-amine and indole-5-carboxylic acid were combined to provide $N^5$-{4-[4-amino-2-(2-methoxyethyl)-1H-imidazo[4,5-c]quinolin-1-yl]butyl}-5-indolecarboxamide as an off white solid. $^1$H NMR (300 MHz, DMSO-d$_6$) δ11.31 (s, 1H), 8.34 (t, J=5.5 Hz, 1H), 8.06 (m, 2H), 7.63–7.58 (m, 2H), 7.42–7.38 (m, 3H), 7.22 (t, J=7.1 Hz, 1H), 6.67 (broad s, 2H), 6.50 (s, 1H), 4.58 (m, 2H), 3.81 (t, J=6.6 Hz, 2H), 3.34 (m, 2H), 3.25 (s, 3H), 3.21 (t, J=6.6 Hz, 2H), 1.89 (m, 2H), 1.72 (m, 2H); MS (EI) m/e 456.2264 (456.2274 calcd for C$_{26}$H$_{28}$N$_6$O$_2$).

EXAMPLE 64

$N^1$-[4-(4-Amino-1H-imidazo[4,5-c]quinolin-1-yl)butyl]-4-phenoxybenzamide

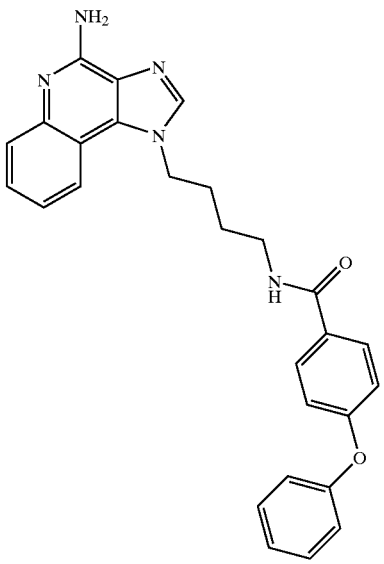

According to the general method of Example 14, 1-(4-arninobutyl)-1H-imidazo[4,5-c]quinolin-4-amine and 4-phenoxybenzoyl chloride were combined to provide $N^1$-[4-(4-amino-1H-imidazo[4,5-c]quinolin-1-yl)butyl]-4-phenoxybenzamide as a white powder, m.p. 90.5–91.5° C. $^1$H NMR (500 MHz, DMSO-d$_6$) δ8.42 (t, J=5.7 Hz, 1H), 8.21 (s, 1H), 8.03 (d, J=7.9 Hz, 1H), 7.81 (d, J=8.9 Hz, 2H), 7.62 (d, J=7.9 Hz, 1H), 7.45–7.40 (m, 3H), 7.21 (m, 2H), 7.07 (d, J=7.6 Hz, 2H), 6.99 (d, J=8.9 Hz, 2H), 6.61 (broad s, 2H), 4.63 (t, J=7.0 Hz, 2H), 3.25 (m, 2H), 1.92 (m, 2H), 1.58 (m, 2H); MS (EI) m/e 451.2008 (451.2008 calcd for C$_{27}$H$_{25}$N$_5$O$_2$).

EXAMPLE 65

$N^5$-{4-[4-Amino-2-(2-methoxyethyl)-1H-imidazo[4,5-c]quinolin-1-yl]butyl}-5-(2-phenyl-1-ethynyl)nicotinamide

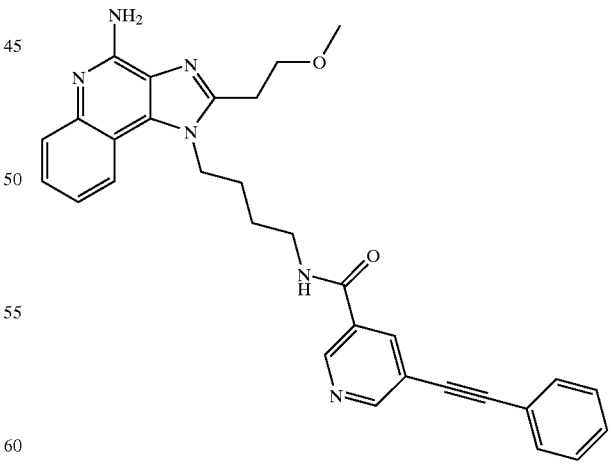

According to the general method of Example 50, 1-(4-aminobutyl)-2-(2-methoxyethyl)-1H-imidazo[4,5-c]quinolin-4-amine and 5-(phenylethynyl)pyridine-3-carboxylic acid were combined to provide $N^5$-{4-[4-amino-2-(2-methoxyethyl)-1H-imidazo[4,5-c]quinolin-1-yl]butyl}-5-(2-phenyl-1-ethynyl)nicotinamide as a yellow solid, m.p. 76.0–78.0° C. $^1$H NMR (300 MHz, DMSO-d6) δ8.95 (d, J=2.1 Hz, 1H), 8.87 (d, J=2.0 Hz, 1H), 8.79 (t, J=2.1 Hz, 1H), 8.31 (d, J=2.0 Hz, 1H), 8.02 (d, J=8.1 Hz, 1H), 7.61 (m, 3H), 7.48 (m, 3H), 7.40 (m, 1H), 7.19 (m, 1H), 6.56 (broad s, 2H), 4.57 (t, J=7.4 Hz, 2H), 3.82 (t, J=6.7 Hz, 2H), 3.37 (m, 2H), 3.27 (s, 3H), 3.21 (t, J=6.7 Hz, 2H), 1.89 (m, 2H), 1.72 (m, 2H); MS (CI) m/e 519 (M+H).

EXAMPLE 66

$N^3$-[4-(4-Amino-2-phenyl-1H-imidazo[4,5-c]quinolin-1-yl)butyl]nicotinamide

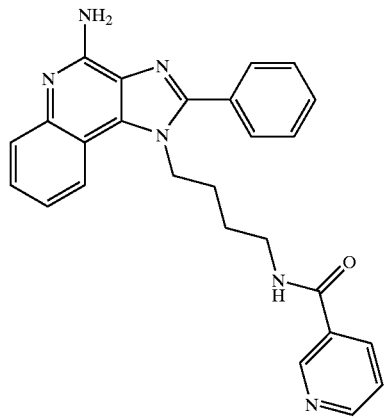

Part A

A solution of benzoyl chloride (5.3 g, 37.7 mmol) in dichloromethane (100 mL) was slowly added to a solution of tert-butyl N-{4-[(3-aminoquinolin-4-yl)amino]butyl}carbamate (12.5 g, 37.7 mmol) in dichloromethane (250 mL) at ambient temperature. The reaction mixture was maintained at ambient temperature overnight. The resulting precipitate was isolated by filtration and dried to provide 11.0 g of tert-butyl N-(4-{[3-(benzoylamino)quinolin-4-yl]amino}butyl)carbamate hydrochloride as a white solid.

Part B

Triethylamine (7.26 g, 71.7 mmol) was added to a solution of the material from Part A in ethanol (200 mL) and heated at reflux for 2 days. The reaction mixture was concentrated to provide an orange syrup. HPLC mass spec analysis showed that the syrup contained the desired product and starting material. The syrup was taken up in dichloromethane (100 mL) and then cooled in an ice bath. Triethylamine (5 mL) and benzoyl chloride (1.9 mL) were added. The reaction mixture was maintained at ambient temperature for 2 days at which time analysis by HPLC indicated that the reaction was not complete. The reaction mixture was concentrated under vacuum. The residue was taken up in isopropyl alcohol (150 mL). Triethylamine (5 mL) was added and the reaction mixture was heated at reflux overnight. The reaction mixture was concentrated under vacuum. The residue was purified by flash chromatography (silica gel; eluting with 10% methanol in dichloromethane). The fractions containing product were combined and concentrated under vacuum. The residue was recrystallized from acetonitrile to provide 6.7 g of tert-butyl N-[4-(2-phenyl-1H-imidazo[4,5-c]quinolin-1-yl)butyl]carbamate as a solid, m.p. 158–159° C.

Part C

3-Chloroperoxybenzoic acid (1.05 eq of 65%) was slowly added in small portions to a solution of tert-butyl N-[4-(2-phenyl-1H-imidazo[4,5-c]quinolin-1-yl)butyl]carbamate (6.56 g, 15.75 mmol) in dichloromethane (120 mL). After 3 hours the reaction was quenched with 1% aqueous sodium bicarbonate (200 mL). The layers were separated. The aqueous layer was extracted with dichloromethane (2×50 mL). The organic fractions were combined, dried over magnesium sulfate and then concentrated under vacuum to provide a pale orange syrup. The syrup was triturated with diethyl ether to provide 6.8 g of 1-[4-(tert-butylcarbamyl)butyl]-2-phenyl-1H-imidazo[4,5-c]quinoline-5N-oxide as a pale tan solid, m.p. 178–181° C.

Part D

A solution of 1-[4-(tert-butylcarbamyl)butyl]-2-phenyl-1H-imidazo[4,5-c]quinoline-5N-oxide (6.8 g, 15.75 mmol) in dichloromethane (100 mL) was chilled in an ice bath. Concentrated ammonium hydroxide (30 mL) was added. Tosyl chloride (3.0 g, 15.75 mmol) was added in small portions over a period of 30 minutes. The reaction mixture was allowed to warm to ambient temperature overnight. The reaction was quenched with water (350 mL). The layers were separated. The aqueous layer was extracted with dichloromethane. The organic fractions were combined, dried over magnesium sulfate and then concentrated under vacuum to provide a tan solid. This material was purified by flash chromatography (silica gel eluting with 10% methanol in dichloromethane) to provide 4.8 g of product. The bulk of the material was carried on to the next step. A small portion was recrystallized from toluene to provide tert-butyl N-[4-(4-amino-2-phenyl-1H-imidazo[4,5-c]quinolin-1-yl)butyl]carbamate as a solid, m.p. 182–183° C. Analysis: Calculated for $C_{25}H_{29}N_5O_2$: %C, 69.58; %H, 6.77; %N, 16.22; Found: %C, 69.86; %H, 6.95; %N, 15.80.

Part E

The material from Part D was dissolved in methanol (15 mL) and 1 N hydrochloric acid (100 mL) and then heated at reflux for 2 hours. The reaction mixture was concentrated under vacuum to a volume of about 50 mL. Addition of concentrated ammonium hydroxide to pH 12 did not produce a precipitate. The pH was adjusted to 7 with 1 N hydrochloric acid. The mixture was extracted with dichloromethane and then with ethyl acetate. The aqueous layer was concentrated to dryness. The residue was dissolved in water (50 mL) and then extracted continuously with refluxing chloroform for 36 hours. The chloroform extract was concentrated under vacuum to provide a light tan solid. This material was recrystallized from acetonitrile to provide 2.5 g of 1-(4-aminobutyl)-2-phenyl-1H-imidazo[4,5-c]quinolin-4-amine as an off white solid, m.p. 175–177° C. Analysis: Calculated for $C_{20}H_{21}N_5$: %C, 72.48; %H, 6.39; %N, 21.13; Found: %C, 72.72; %H, 6.32; %N, 20.71.

Part F

According to the general method of Example 61, 1-(4-aminobutyl)-2-phenyl-1H-imidazo[4,5-c]quinolin-4-amine and nicotinoyl chloride hydrochloride were combined to provide $N^3$-[4-(4-amino-2-phenyl-1H-imidazo[4,5-c]quinolin-1-yl)butyl]nicotinamide as a white crystalline solid, m.p. 84.5–86.1° C. $^1$H NMR (300 MHz, DMSO-d$_6$) δ8.91 (s, 1H), 8.69 (m, 1H), 8.56 (m, 1H), 8.07 (m, 2H), 7.75–7.41 (m, 8H), 7.21 (m, 1H), 6.72 (broad s, 2H), 4.60 (m, 2H), 3.15 (t, J=6.0 Hz, 2H), 1.86 (m, 2H), 1.40 (m, 2H); MS (CI) m/e 437 (M+H).

EXAMPLE 67

N -[4-(4-Amino-2-phenyl-1H-imidazo[4,5-c]quinolin-1-yl)butyl]-2-quinolinecarboxamide

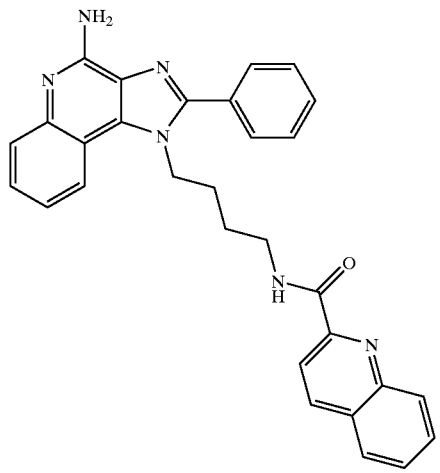

According to the general method of Example 61, 1-(4-aminobutyl)-2-phenyl-1H-imidazo[4,5-c]quinolin-4-amine and quinoline-2-carbonyl chloride were combined to provide N-[4-(4-amino-2-phenyl-1H-imidazo[4,5-c]quinolin-1-yl)butyl]-2-quinolinecarboxamide as an off white crystalline solid, m.p. 81.1–83.9° C. $^1$H NMR (300 MHz, DMSO-$d_6$) δ8.90 (t, J=6.0 Hz, 1H), 8.55 (d, J=8.5 Hz, 1H), 8.12–8.07 (m, 4H), 7.90–7.84 (m, 1H), 7.75–7.54 (m, 7H), 7.36 (t, J=7.5 Hz, 1H), 7.18 (t, J=7.5 Hz, 1H), 6.70 (broad s, 2H), 4.61 (m, 2H), 3.23 (m, 2H), 1.88 (m, 2H), 1.49 (m, 2H); MS (CI) m/e 487 (M+H).

EXAMPLES 68–102

The compounds shown in the table below were prepared using the synthetic method described in Reaction Scheme II above.

A solution of 1-(4-aminobutyl)-1H-imidazo[4,5-c]quinolin-4-amine (36 μmol) in 10 mL of dichloromethane in a screw-capped test tube was cooled down to −5° C. The acid chloride (45 μmol) was added as a 0.3 M solution in dichloromethane. Argon was bubbled through the mixture during addition and for an additional 15 seconds, and the mixture was allowed to stand at −5° C. overnight. To this mixture was added approximately 90 mg of an aminomethyl polystyrene resin (0.62 meq/g, 100–200 mesh), and the mixture was warmed to reflux and shaken at 600 rpm for 3 hours. The compounds were purified by eluting through a short plug of silica gel with 10:1 dichloromethane-methanol, collecting ca. 1 mL fractions and pooling the product fractions (fractions analyzed by tlc in 9:1 dichloromethane-methanol to identify product). Compounds were analyzed by 500 MHz $^1$H nmr and APCI-MS (plug injection or an LC/MS protocol).

| Example No. | Structure | APCI-MS m/e | 500 MHz $^1$H NMR |
|---|---|---|---|
| 68 | 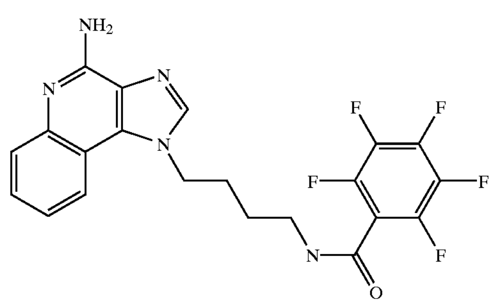 | 450.10 | (DMSO-$d_6$)δ8.93(t, J=5.2Hz, 1H), 8.23(s, 1H), 8.06 (d, J=8.2Hz, 1H), 7.63(d, J=8.5Hz, 1H), 7.46(t, J=7.8Hz, 1H), 7.27(t, J=7.6Hz, 1H), 6.75(bs, 2H), 4.65(t, J=7Hz, 2H), 3.31(q, J=6Hz, 2H), 1.92(quintet, J=8Hz, 2H), 1.56 (quintet, J=7Hz, 2H) |
| 69 | 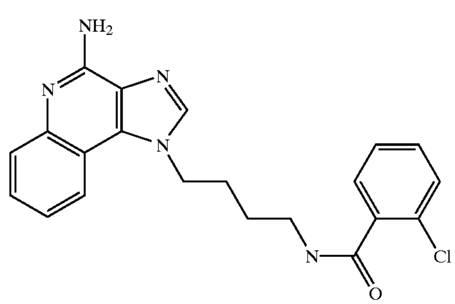 | 394.12 | (DMSO-$d_6$)δ8.40(t, J=5.8Hz, 1H), 8.23(s, 1H), 8.08 (d, J=8.2Hz, 1H), 7.64(d, J=8.5Hz, 1H), 7.47(t, J=8.2Hz, 1H), 7.43(d, J=7.9Hz, 1H), 7.39(dt, J=1.5Hz, J=7Hz, 1H), 7.30(t, J=6.4Hz, 1H), 7.28(t, J=10.4Hz, 1H), 7.23(dd, J=1.5Hz, J=7.3Hz, 1H), 6.75(bs, 2H), 4.65(t, J=7Hz, 2H), 3.26(q, J=6Hz, 2H), 1.95(quintet, J=8Hz,2H), 1.56 (quintet, J=7.5Hz, 2H) |

| Example No. | Structure | APCI-MS m/e | 500 MHz $^1$H NMR |
|---|---|---|---|
| 70 | 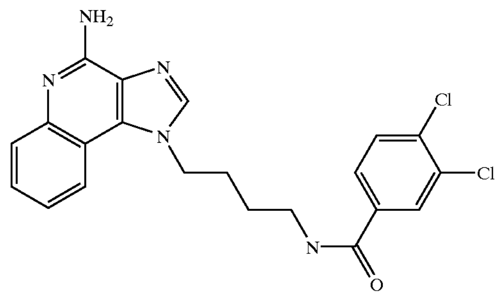 | 428.07 | (DMSO-d$_6$)δ8.47(t, J=5.8Hz, 1H), 8.22(s, 1H), 8.07 (d, J=8.2Hz, 1H), 7.64(d, J=8.8Hz, 1H), 7.63 (d, J=2.1Hz, 1H), 7.47(t, J=8.2Hz, 1H), 7.40(dd, J=2.1Hz, J=10.4Hz, 1H), 7.29(t, J=7.0Hz, 1H), 7.26(d, J=8.2Hz, 1H), 6.75(bs, 2H), 4.65(t, J=5.5Hz, 2H), 3.25(q, J=6.5Hz, 2H), 1.94(quintet, J=8Hz, 2H), 1.54(quintet, J=7Hz, 2H), |
| 71 | 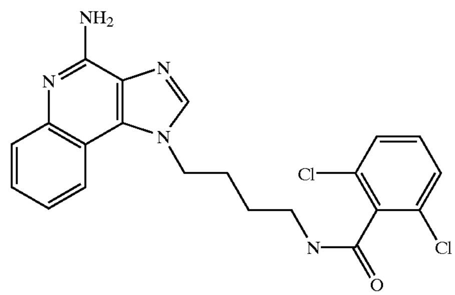 | 428.06 | (DMSO-d$_6$)δ8.65(t, J=6.1Hz, 1H), 8.23(s, 1H), 8.08 (d, J=7.9Hz, 1H), 7.64(d, J=8.2Hz, 1H), 7.47(t, J=7.9Hz, 1H), 7.43(d, J=9Hz, 1H), 7.44(d, J=7Hz, 1H), 7.38 (dd, J=9.2Hz, J=7Hz, 1H), 7.28(t, J=7.9Hz, 1H), 6.8(bs, 2H), 4.65(t, J=6.5Hz, 2H), 3.28(m, 2H), 1.96 (quintet, J=7.5Hz, 2H), 1.57(quintet, J=8Hz, 2H) |
| 72 | 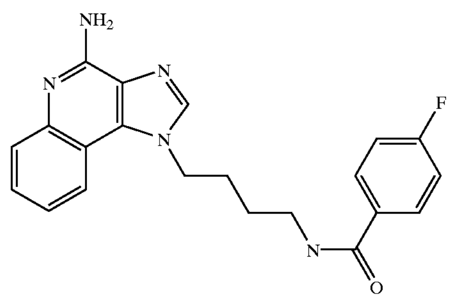 | 378.11 | (DMSO-d$_6$)δ8.50(t, J=5.8Hz, 1H), 8.23(s, 1H), 8.04 (d, J=8.2Hz, 1H), 7.84(dd, J=2.1Hz, J=5.8Hz, 2H), 7.62 (d, J=7.3Hz, 1H), 7.44(t, J=7Hz, 1H), 7.26(t, J=6.7Hz, 2H), 7.22(t, J=8.2Hz, 1H), 6.74(bs, 2H), 4.63(t, J=7Hz, 2H), 3.28(m, 2H), 1.91(quintet, J=7.5Hz, 2H), 1.57 (quintet, J=8Hz, 2H) |
| 73 | 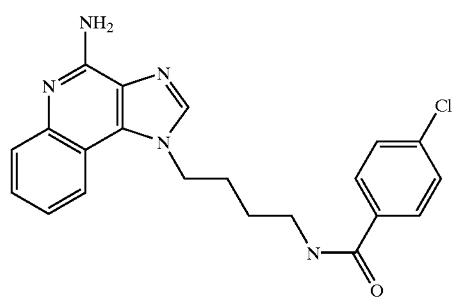 | 394.07 | (DMSO-d$_6$)δ8.56(t, J=5.6Hz, 1H), 8.24(s, 1H), 8.05 (d, J=7.9Hz, 1H), 7.79(d, J=8.5Hz, 2H), 7.63 (d, J=8.2Hz, 1H), 7.50(d, J=8.9Hz, 2H), 7.46(t, J=7.6Hz, 1H), 7.23(t, J=7.6Hz, 1H), 6.8(bs, 2H), 4.64(t, J=7Hz, 2H), 3.29(q, J=6.5Hz, 2H), 1.91(quintet, J=7.5Hz, 2H), 1.57 (quintet, J=7.5Hz, 2H) |
| 74 | 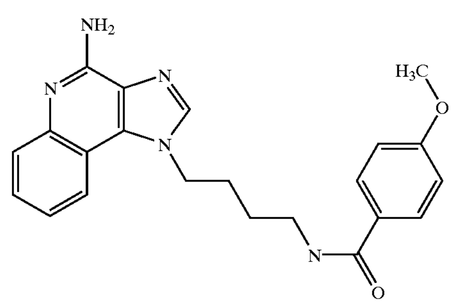 | 390.13 | (DMSO-d$_6$)δ8.33(t, J=5.6Hz, 1H), 8.24(s, 1H), 8.05 (d, J=8.2Hz, 1H), 7.76(d, J=8.8Hz, 2H), 7.63 (d, J=8.2Hz, 1H), 7.45(t, J=8.2Hz, 1H), 7.24(t, J=7.9Hz, 1H), 6.95(d, J=8.8Hz, 2H), 6.81(bs, 2H), 4.64(t, J=7Hz, 2H), 3.80(s, 3H), 3.28(quintet, J=5.5Hz, 2H), 1.90 (quintet, J=8Hz, 2H), 1.57(quintet, J=8.5Hz, 2H) |

| Example No. | Structure | APCI-MS m/e | 500 MHz $^1$H NMR |
|---|---|---|---|
| 75 | 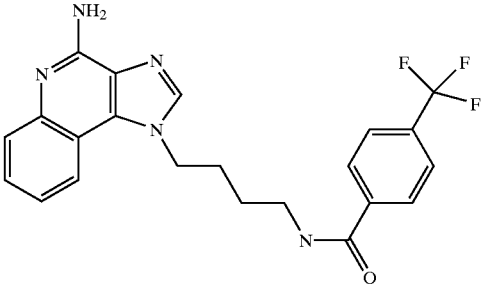 | 428.10 | (DMSO-d$_6$)δ8.71(t, J=5.6Hz, 1H), 8.27(s, 1H), 8.06 (d, J=7.9Hz, 1H), 7.96(d, J=8.2Hz, 2H), 7.64 (d, J=7.9Hz, 2H), 7.64(d, J=7.9Hz, 1H), 7.46(t, J=7.3Hz, 1H), 7.25(t, J=7Hz, 1H), 6.9(bs, 2H), 4.65(t, J=7Hz, 2H), 3.31(m, 2H), 1.92(quintet, J=8Hz, 2H), 1.59 (quintet, J=7.5Hz, 2H) |
| 76 | 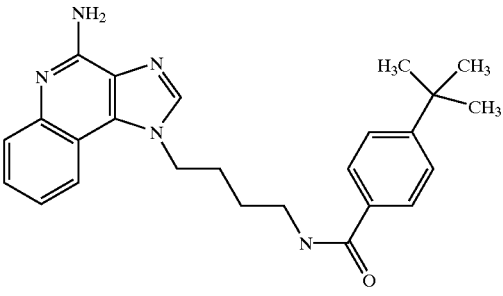 | 416.22 | (DMSO-d$_6$)δ8.54(s, 1H), 8.39(t, J=5.5Hz, 1H), 8.22 (d, J=8.2Hz, 1H), 7.82(d, J=8.2Hz, 1H), 7.70(t, J=4Hz, 1H), 7.68(d, J=4.3Hz, 2H), 7.52(t, J=8Hz, 1H), 7.43 (d, J=7.8Hz, 2H), 4.72(t, J=7Hz, 2H), 3.30(q, J=6.5Hz, 2H), 1.91(quintet, J=7.5Hz, 2H), 1.59(quintet, J=7.5Hz, 2H), 1.29(s, 9H) |
| 77 | 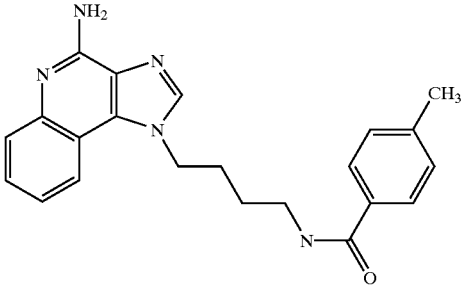 | 374.18 | (DMSO-d$_6$)δ8.54(s, 1H), 8.38(t, J=5.8Hz, 1H), 8.23 (d, J=8.2Hz, 1H), 7.82(d, J=8.6Hz, 1H), 7.71(t, J=8.2Hz, 1H), 7.659(d, J=8.2Hz, 2H), 7.54(t, J=8.2Hz, 1H), 7.22 (d, J=7.9Hz, 2H), 4.71(t, J=6.5Hz, 2H), 3.28(q, J=6Hz, 2H), 2.34(s, 3H), 1.92(quintet, J=8Hz, 2H), 1.60 (quintet, J=7.5Hz, 2H) |
| 78 | 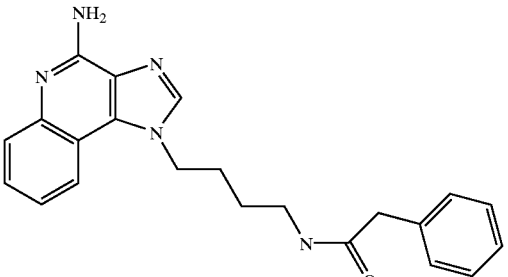 | 374.18 | (DMSO-d$_6$)δ8.50(s, 1H), 8.22(d, J=8.2Hz, 1H), 8.06 (t, J=5.8Hz, 1H), 7.84(d, J=8.5Hz, 1H), 7.74(t, J=7Hz, 1H), 7.58, (t, J=7.6Hz, 1H), 7.21(m, 2H), 7.18(m, 3H), 4.67 (t, J=7Hz, 2H), 3.33(s, 2H), 3.09(q, J=6Hz, 2H), 1.84 (quintet, J=8Hz, 2H), 1.48(quintet, J=7.5Hz, 2H) |
| 79 | 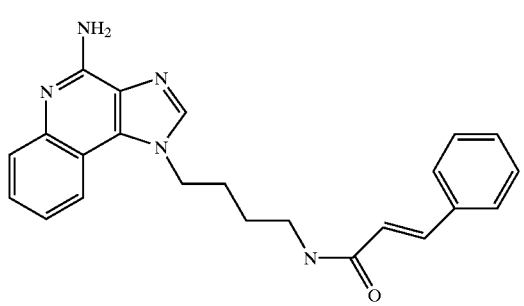 | 386.15 | (DMSO-d$_6$)δ8.55(s, 1H), 8.24(d, J=8.2Hz, 1H), 8.16 (t, J=5.8Hz, 1H), 7.82(d, J=8.6Hz, 1H), 7.72(t, J=7.3Hz, 1H), 7.58(t, J=7.3Hz, 1H), 7.53(d, J=6.7Hz, 2H), 7.40(m, 4H), 6.57(d, J=15.9Hz, 1H), 4.72(t, J=7Hz, 2H), 3.23 (q, J=6Hz, 2H), 1.91(quintet, J=7.5Hz, 2H), 1.55 (quintet, J=7.5Hz, 2H) |

| Example No. | Structure | APCI-MS m/e | 500 MHz $^1$H NMR |
|---|---|---|---|
| 80 | 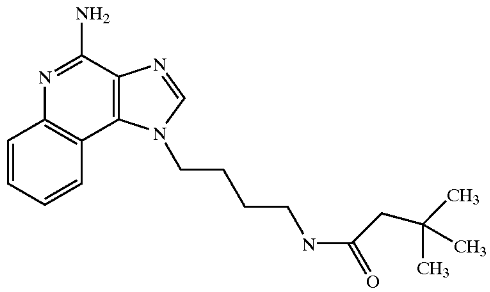 | 354.19 | (DMSO-d$_6$)δ8.53(s, 1H), 8.24(d, J=8.2Hz, 1H), 7.83 (d, J=8.2Hz, 1H), 7.74(m, 2H), 7.58(t, J=7.8, 1H), 4.70 (t, J=7Hz, 2H), 3.06(q, J=6Hz, 2H), 1.86(s, 2H), 1.86 (quintet, J=8.5Hz, 2H), 1.44(quintet, J=7.5Hz, 2H), 0.84 (s, 9H) |
| 81 | 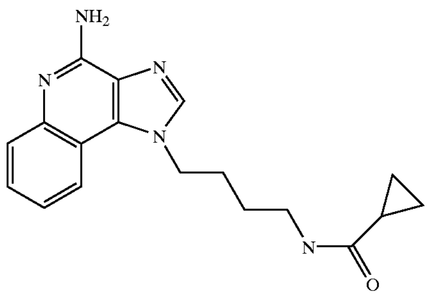 | 324.15 | (DMSO-d$_6$)δ8.53(s, 1H), 8.23(d, J=8.5Hz, 1H), 8.06 (t, J=5.5Hz, 1H), 7.84(d, J=8.2Hz, 1H), 7.74(t, J=8.2Hz, 1H), 7.59(t, J=8.2Hz, 1H), 4.69(t, J=7Hz, 2H), 3.09 (q, J=6Hz, 2H), 1.86(quintet, J=7Hz, 2H), 1.47(m, 3H), 0.59(m, 4H) |
| 82 | 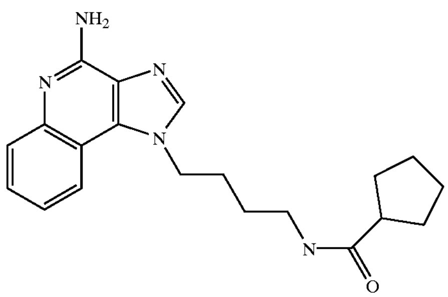 | 352.16 | (DMSO-d$_6$)δ8.52(s, 1H), 8.23(d, J=7.9Hz, 1H), 7.83 (d, J=8.2Hz, 1H), 7.74(m, 2H), 7.60(t, J=7.6Hz, 1H), 4.69 (t, J=7.5Hz, 2H), 3.06(q, J=6Hz, 2H), 2.42 (quintet, J=8Hz, 1H), 1.84(quintet, J=7.5Hz, 2H), 1.59 (m, 2H), 1.55(m, 2H), 1.48(m, 6H) |
| 83 | 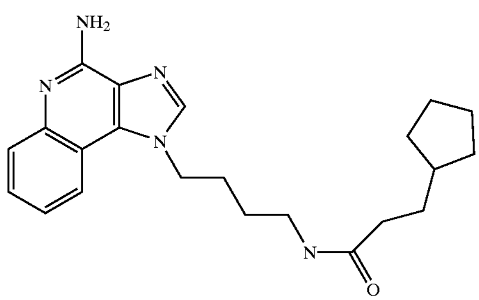 | 380.16 | (DMSO-d$_6$)δ8.52(s, 1H), 8.22(d, J=8.2Hz, 1H), 7.83 (d, J=8.2Hz, 1H), 7.77(t, J=5.8Hz, 1H), 7.73(t, J=8.2Hz, 1H), 7.58(t, J=8.2Hz, 1H), 4.68(t, J=7Hz, 2H), 3.06 (q, J=6Hz, 2H), 1.98(t, J=8Hz, 2H), 1.84 (quintet, J=7.5Hz, 2H), 1.62(m, 3H), 1.48(m, 8H), 0.97 (m, 2H) |
| 84 | 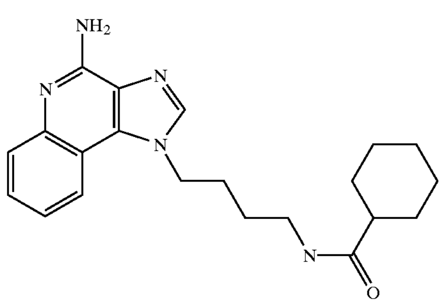 | 366.15 | (DMSO-d$_6$)δ9.2(b, 2H), 8.52(s, 1H), 8.22(d, J=8.2Hz, 1H), 7.83(d, J=8.5Hz, 1H), 7.74(t, J=8.2Hz, 1H), 7.65 (t, J=5.8Hz, 1H), 7.58(t, J=7.9Hz, 1H), 4.68(t, J=7Hz, 2H), 3.04(q, J=6.5Hz, 2H), 1.95(m, 1H), 1.83 (quintet, J=8Hz, 2H), 1.60(m, 3H), 1.50(m, 2H), 1.43 (quintet, J=7.5Hz, 2H), 1.14(m, 5H) |

-continued

| Example No. | Structure | APCI-MS m/e | 500 MHz $^1$H NMR |
|---|---|---|---|
| 85 | 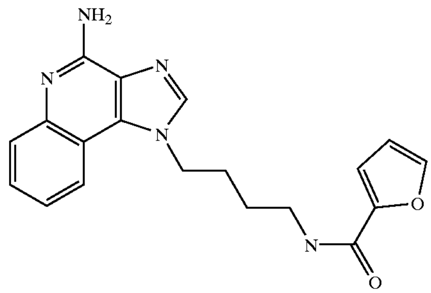 | 350.18 | (DMSO-d$_6$)δ9.0(bs, 2H), 8.54(s, 1H), 8.39(t, J=5Hz, 1H), 8.22(d, J=5Hz, 1H), 7.82(d, J=10Hz, 1H), 7.80(s, 1H, 7.72 (t, J=10Hz, 1H), 7.54(t, J=10Hz, 1H), 7.02(dd, J=1Hz, J=3Hz, 1H), 6.60(dd, J=1.7Hz, J=3.5Hz, 1H), 4.70 (t, J=7.5Hz, 2H), 3.25(q, J=6Hz, 2H), 1.90 (quintet, J=7.5Hz, 2H), 1.58(quintet, J=7Hz, 2H) |
| 86 | 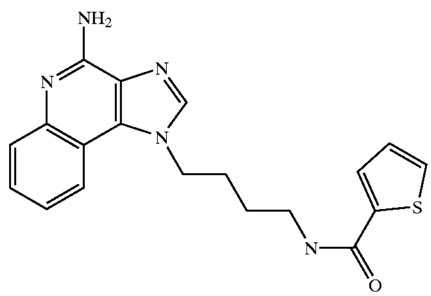 | 366.25 | (DMSO-d$_6$)δ8.51(t, J=5.5Hz, 1H), 8.32(s, 1H), 8.10 (d, J=8.6Hz, 1H), 7.72(dd, J=0.9Hz, J=4.9Hz, 1H), 7.68 (m, 2H), 7.52(t, J=7.9Hz, 1H), 7.34(bs, 2H), 7.31 (t, J=7.9Hz, 1H), 7.11(dd, J=4Hz, J=4.9Hz, 1H), 4.66 (t, J=7.5Hz, 2H), 3.27(q, J=6Hz, 2H), 1.91 (quintet, J=7.5Hz, 2H), 1.58(quintet, J=8Hz, 2H) |
| 87 | 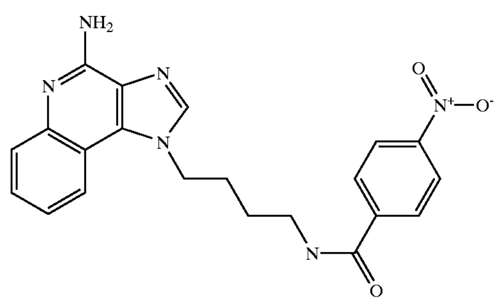 | 405.21 | (DMSO-d$_6$)δ8.80(t, J=5.8Hz, 1H), 8.28(s, 1H), 8.27 (d, J=8.6Hz, 2H), 8.07(d, J=8Hz, 1H), 7.98(d, J=8.9Hz, 2H), 7.65(d, J=8.6Hz, 1H), 7.47(t, J=7.9Hz, 1H), 7.27 (t, J=7.9Hz, 1H), 7.07(bs, 2H), 4.66(t, J=7Hz, 2H), 1.93 (quintet, J=8Hz, 2H), 1.60(quintet, J=7.5Hz, 2H) |
| 88 | 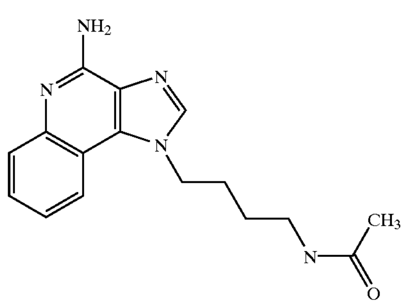 | 298.16 | (DMSO-d$_6$)δ8.33(s, 1H), 8.11(d, J=8.1Hz, 1H), 7.83 (t, J=6Hz, 1H), 7.71(d, J=8.1Hz, 1H), 7.56(t, J=8.1Hz, 1H), 7.39(t, J=7.8Hz, 1H), 4.63(t, J=7Hz, 2H), 3.05 (q, J=6.5Hz, 2H), 1.85(quintet, J=7.5Hz, 2H), 1.74(s, 3H), 1.44(quintet, J=7.5Hz, 2H) |
| 89 | 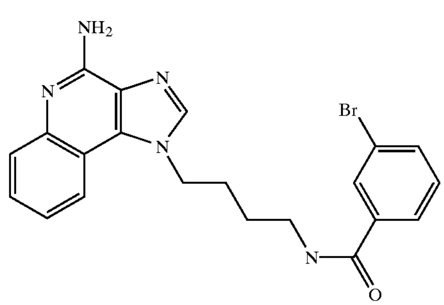 | 439.30 | (DMSO-d$_6$)δ8.59(t, 1H), 8.43(s, 1H), 8.16 (d, J=7.6Hz, 1H), 7.94(d, J=1.7Hz, 1H), 7.75(t, J=6.8Hz, 2H), 7.71(d, J=8.1Hz, 1H), 7.60(m, 1H), 7.40(t, J=7.8Hz, 2H), 4.68(t, J=6.5Hz, 2H), 3.30(q, J=6Hz, 2H), 1.91 (quintet, J=6Hz, 2H), 1.59(quintet, J=6Hz, 2H) |

-continued

| Example No. | Structure | APCI-MS m/e | 500 MHz ¹H NMR |
|---|---|---|---|
| 90 | 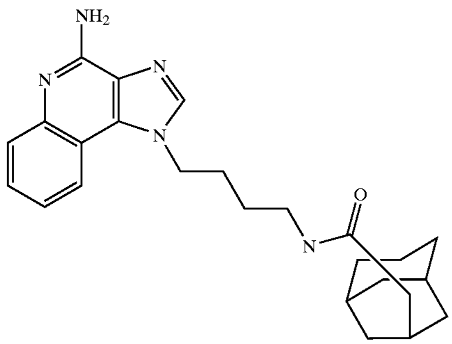 | 418.28 | (DMSO-d₆)δ8.29(s, 1H), 8.08(d, J=8.5Hz, 1H), 7.68 (d, J=7.8Hz, 1H), 7.53(t, J=7.6Hz, 1H), 7.36(t, J=7.3Hz, 1H), 7.30(t, J=5.9Hz, 1H), 4.62(t, J=6.5Hz, 2H), 3.05 (q, J=6.5Hz, 2H), 1.86(m, 5H), 1.60(m, 12H), 1.41 (quintet, J=7Hz, 2H) |
| 91 | 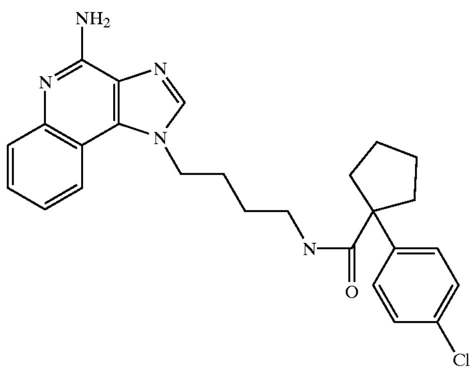 | 462.21 | (DMSO-d₆)δ8.25(s, 1H), 8.06(d, J=8.3Hz, 1H), 7.70 (d, J=8.1Hz, 1H), 7.55(t, J=7.8Hz, 1H), 7.49(t, J=5.6Hz, 1H), 7.37(t, J=7.3Hz, 1H), 7.24(s, 4H), 4.57(t, J=7Hz, 2H), 3.01(q, J=6Hz, 2H), 2.38(m, 2H), 1.68(m, 4H), 1.49(m, 2H), 1.40(m, 4H) |
| 92 | 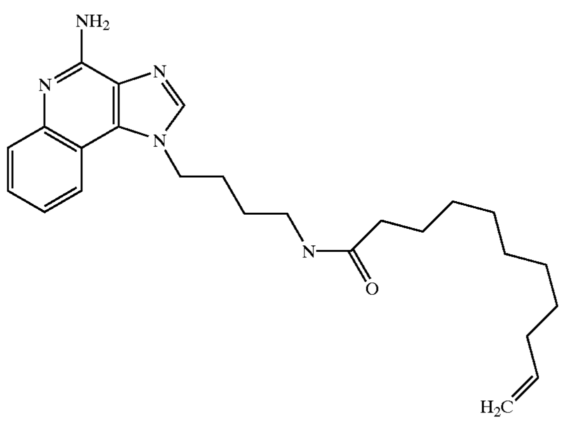 | 422.28 | (DMSO-d₆)δ8.36(s, 1H), 8.13(d, J=8.8Hz, 1H), 7.86 (b, 2H), 7.76(t, J=6Hz, 1H), 7.74(d, J=8.5Hz, 1H), 7.59 (t, J=8.1Hz, 1H), 7.43(t, J=7.5Hz, 1H), 5.77(m, 1H), 4.98 (dd, J=2Hz, J=17Hz, 1H), 4.92(dd, J=1.5Hz, J=10Hz, 1H), 4.64(t, J=7Hz, 2H), 3.07(q, J=5.5Hz, 2H),1.97 (m, J=7.5Hz, 4H), 1.84(quintet, J=7Hz, 2H), 1.45 (quintet, J=8Hz, 2H), 1.40(quintet, J=6.5Hz, 2H), 1.30 (quintet, J=7Hz, 2H), 1.18(m, 8H) |
| 93 | 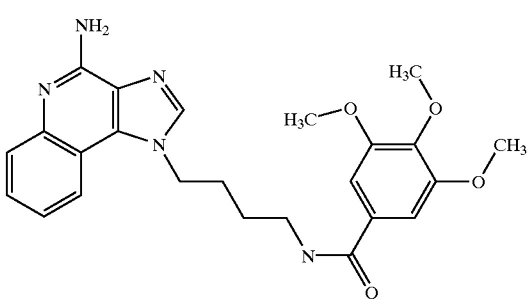 | 450.19 | (DMSO-d₆)δ8.43(t, J=5.6Hz, 1H), 8.31(s, 1H), 8.08 (d, J=7.8Hz, 1H), 7.67(d, J=8.1Hz, 1H), 7.50(t, J=7.3Hz, 1H), 7.29(t, J=7.8Hz, 1H), 7.11(s, 2H), 4.67(t, J=7Hz,2H), 3.78(s, 6H), 3.69(s, 3H), 3.29(q, J=6Hz, 2H), 1.91 (quintet, J=7.5Hz, 2H), 1.58(quintet, J=7.5Hz, 2H) |

| Example No. | Structure | APCI-MS m/e | 500 MHz $^1$H NMR |
|---|---|---|---|
| 94 | 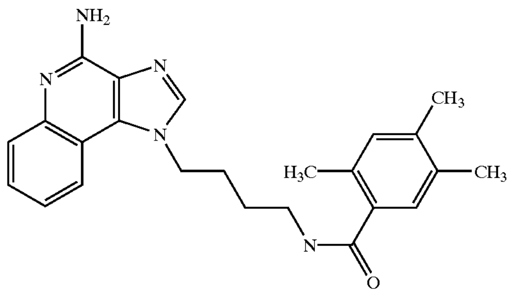 | 402.25 | (DMSO-d$_6$)δ8.24(s, 1H), 8.19(t, J=5.9Hz, 1H), 8.08 (d, J=8Hz, 1H), 7.65(d, J=8.3Hz, 1H), 7.48(t, J=8.3Hz, 1H), 7.29(t, J=7.8Hz, 1H), 6.87(bs, 2H), 6.77(s, 2H), 4.65 (t, J=6.5Hz, 2H), 3.26(q, J=6.5Hz, 2H), 2.19(s, 3H), 2.02 (s, 6H), 1.92(quintet, J=8Hz, 2H), 1.54(quintet, J=8.5Hz, 2H) |
| 95 | 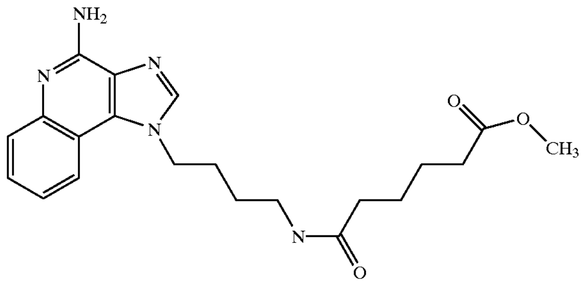 | 398.21 | (DMSO-d$_6$)δ8.28(s, 1H), 8.08(d, J=7.6Hz, 1H), 7.79 (t, J=5.9Hz, 1H), 7.68(d, J=7.8Hz, 1H), 7.52(t, J=7.6Hz, 1H), 7.35(t, J=7.1Hz, 1H), 7.2(bs, 2H), 4.62(t, J=7Hz, 2H), 3.56(s, 3H), 3.06(q, J=5.5Hz, 2H), 2.24(m, 2H), 1.99 (quintet, J=6.5Hz, 2H), 1.84(quintet, J=8Hz, 2H), 1.43 (m, 6H) |
| 96 | 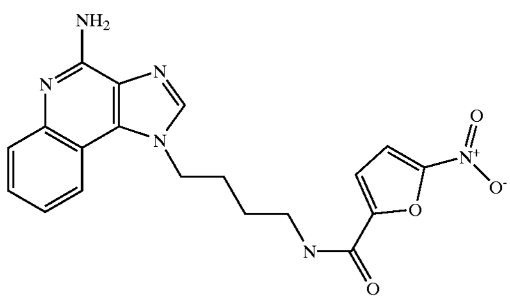 | 395.12 | (DMSO-d$_6$)δ8.88(t, J=5.6Hz, 1H), 8.25(s, 1H), 8.05 (d, J=8.3Hz, 1H), 7.72(d, J=3.9Hz, 1H), 7.63 (d, J=8.3Hz, 1H), 7.45(t, J=7.3Hz, 1H), 7.32(d, J=3.9Hz, 1H), 7.26(t, J=7.1Hz, 1H), 6.93(bs, 2H), 4.64(t, J=7Hz, 2H), 3.28(q, J=6Hz, 2H), 1.90(quintet, J=7Hz, 2H), 1.56 (quintet, J=8Hz, 2H) |
| 97 | 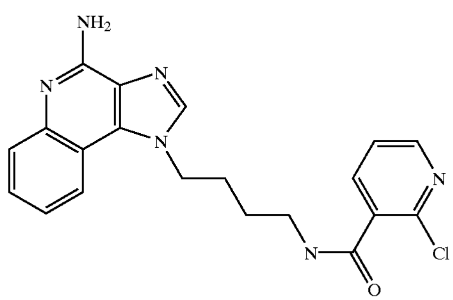 | 395.20 | (DMSO-d$_6$)δ8.57(t, J=5.6Hz, 1H), 8.42(dd, J=1.9Hz, J=4.6Hz, 1H), 8.25(s, 1H), 8.12(d, J=8.0Hz, 1H), 7.70 (dd, J=2Hz, J=7.6Hz, 1H), 7.65(d, J=8.5Hz, 1H), 7.49 (t, J=7.6Hz, 1H), 7.41(dd, J=4.9Hz, J=7.6Hz, 1H), 7.30 (t, J=7.6Hz, 1H), 6.90(bs, 2H), 4.66(t, J=7Hz, 2H), 3.27 (q, J=6.5Hz, 2H), 1.96(quintet, J=8.5Hz, 2H), 1.56 (quintet, J=7.5Hz, 2H) |
| 98 | 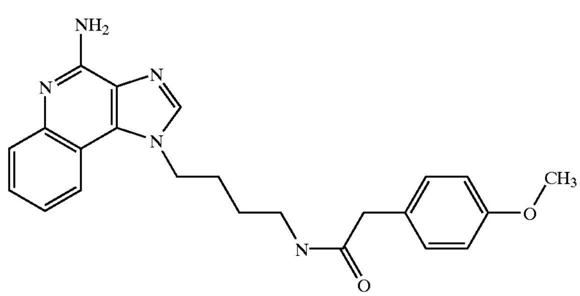 | 404.18 | (DMSO-d$_6$)δ8.36(s, 1H), 8.14(d, J=8.3Hz, 1H), 7.97 (t, J=5.6Hz, 1H), 7.76(d, J=8.3Hz, 1H), 7.62(t, J=7.8Hz, 1H), 7.45(t, J=7.5Hz, 1H), 7.08(d, J=8.5Hz, 2H), 6.76 (d, J=8.8Hz, 2H), 4.63(t, J=7Hz, 2H), 3.70(s, 3H), 3.25 (s, 2H), 3.08(q, J=6Hz, 2H), 1.83(quintet, J=7.5Hz, 2H), 1.46(quintet, J=7Hz, 2H) |

| Example No. | Structure | APCI-MS m/e | 500 MHz ¹H NMR |
|---|---|---|---|
| 99 | 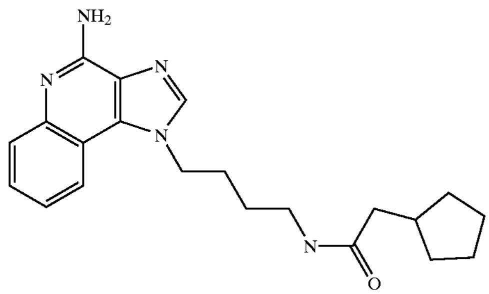 | 366.22 | (DMSO-$d_6$)δ8.35(s, 1H), 8.2(bs, 1H), 8.13 (d, J=7.8Hz, 1H), 7.75(t, J=5.6Hz, 1H), 7.73(d, J=8.8Hz, 1H), 7.59(t, J=7.6Hz, 1H), 7.42(t, J=7.6Hz, 1H), 4.65 (t, J=7Hz, 2H), 3.06(q, J=6Hz, 2H), 2.02(m, J=7.5Hz, 1H), 1.96(d, J=7.5Hz, 2H), 1.84(quintet, J=8Hz, 2H), 1.55 (quintet, J=5Hz, 2H), 1.46(m, J=7.5Hz, 6H), 1.00 (m, J=12Hz, 2H) |
| 100 | 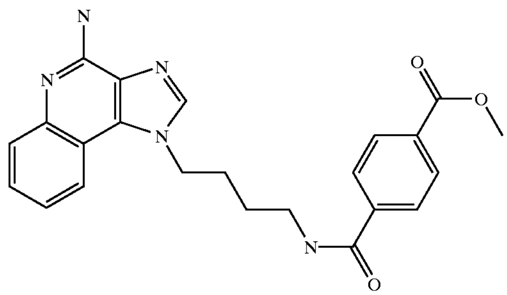 | 418.11 | (DMSO-$d_6$)δ9.6–8.5(b, 2H), 8.66(t, J=5.5Hz, 1H), 8.54 (s, 1H), 8.23(d, J=8.0Hz, 1H), 8.00(d, J=8.0Hz, 2H), 7.87 (d, J=8.0Hz, 2H), 7.81(d, J=8Hz, 1H), 7.70(t, J=8.0 Hz, 1H), 7.53(t, J=8.0Hz, 1H), 4.72(t, J=7.0Hz, 2H), 3.88(s, 3H), 3.31(q, J=5.5Hz, 2H), 1.93(quintet, J=7.0, 2H), 1.61 (quintet, J=7.0Hz, 2H) |
| 101 | 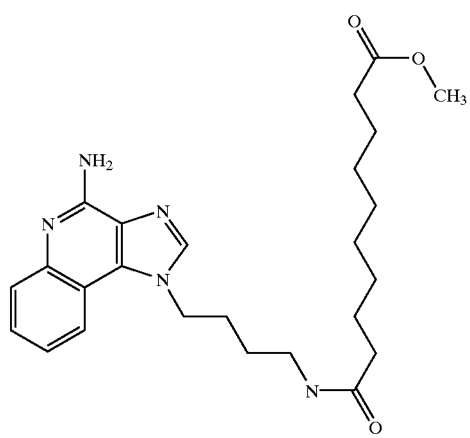 | 454.19 | (DMSO-$d_6$)δ9.6–8.6(b, 2H), 8.51(s, 1H), 8.22 (d, J=8.5Hz, 1H), 7.84(d, J=8.5Hz, 1H), 7.78(t, J=5.5 Hz, 1H), 7.73(t, J=8.5Hz, 1H), 7.58(t, J=8.5Hz, 1H), 4.68 (t, J=7.0Hz, 2H), 3.57(s, 3H), 3.07(q, J=5.5Hz, 2H), 2.26 (t, J=7.0Hz, 2H), 1.84(quintet, J=7.0Hz, 2H), 1.48 (sextet, J=7.0Hz, 4H), 1.38(quintet, J=7.0Hz, 2H), 1.71 (m, 8H) |
| 102 | 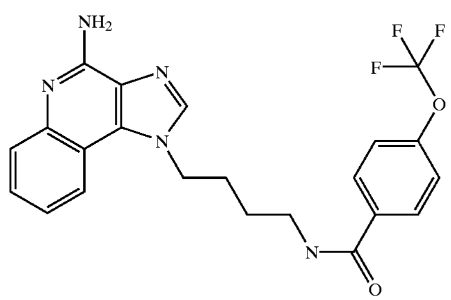 | 444.11 | Compound is trifluoroacetate salt |

EXAMPLES 103–107

The compounds shown in the Table below were prepared according to the synthetic method described below.

A 10 mg (25 μmol) portion of $N^1$-[4-(4-amino-1H-imidazo[4,5-c]quinolin-1-yl)butyl]-4-(chloromethyl) benzamide (example 7) was dissolved in 1 mL of N,N-dimethylformamide in a screw-cap tube, and the appropriate amine (2 eq) was added, along with ca. 70 mg (270 μmol) of N,N-(diisopropyl)aminomethylpolystyrene beads (PS-DIEA, 3.86 meq/g, Argonaut). The mixture was heated to 50° C. and was vortexed overnight at 500 rpm. Another 1–2 eq of amine was added and then heating and vortexing was continued for a second night. The product was isolated by injection of the filtered reaction mixture onto a semi-prep HPLC system (Shimadzu LC-6A pumps, Rainin Microsorb C18 column, 21.4×250 mm, 8 micron particle size, 60A pore, 9.9 mL/min., gradient elution from 2–95% B in 25 min., hold at 95% B for 5 min., where A=0. 1% trifluoroacetic acid/water and B=0.1% trifluoroacetic acid/acetonitrile, peak detection at 254 nm, collected 5 mL fractions). The semi-prep hplc fractions were analyzed by reversed-phase hplc and the appropriate fractions were dried in vacuo to provide the compound as a trifluoroacetate salt. The compound was dissolved in ca. 3–5 mL of 2:1 dichloromethane-methanol and shaken with ca. 80 mg (300 μmol) of diisopropylaminomethyl-polystyrene resin (Argonaut PS-DIEA, 3.86 mmol/g) for 1–2 h to liberate the free amine, and then filtered and dried in vacuo to give the compound as an amorphous solid. Each amine product was analyzed by LC/APCI-MS.

| Example No. | Structure of the Free Base | APCI-MS m/e |
|---|---|---|
| 103 | 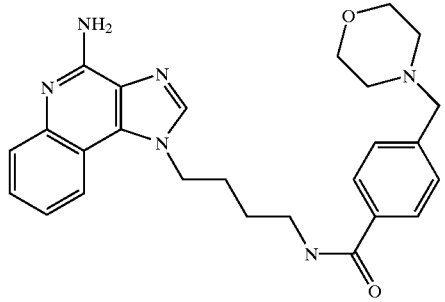 | 459.26 |
| 104 | 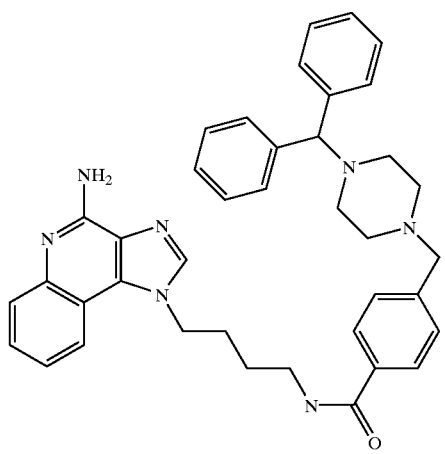 | 624.51 |
| 105 | 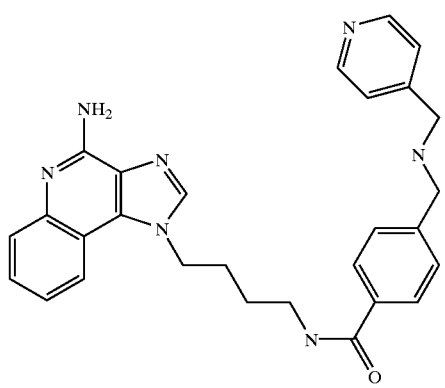 | 480.34 |

-continued

| Example No. | Structure of the Free Base | APCI-MS m/e |
|---|---|---|
| 106 | | 523.31 |
| 107 | | 508.32 |

EXAMPLE 108

$N^1$-(4-(4-Amino-1H-imidazo[4,5-c]quinolin-1-yl)butyl)-2-(2-thienyl)acetamide

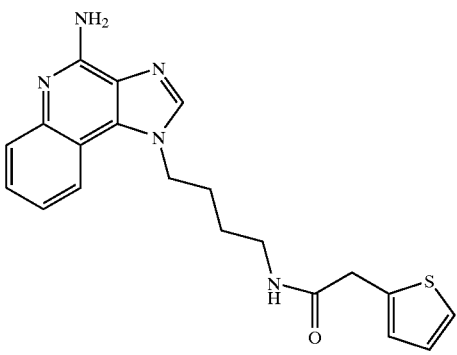

This compound was prepared according to the method of Examples 68–102. (DMSO-$d_6$) δ8.28 (s, 1H), 8.09 (m,2H), 7.70 (d,J=7.9 Hz,1H), 7.54 (t,J=7.9 Hz,1H), 7.36 (t,J=7.3Hz, 1H), 7.28 (dd,J=0.9 Hz, J=5.2 Hz,1H), 6.88 (dd,J=3.4 Hz, J=5.2 Hz,1H), 6.82 (d,J=3.1 Hz, 1H), 4.63 (t,J=7 Hz, 2H), 3.56 (s,2H), 3.10 (q,J=6.5 Hz,2H), 1.85 (quintet,J=7.5 Hz,2H), 1.46 (quintet,J=7.5 Hz,2H) MS (APCI) m/e 380.22 (M+H).

Examples 109–119

The examples in the table below were prepared using the synthetic method described in Reaction Scheme III.

1-(4-Aminobutyl)-1H-imidazo[4,5-c]quinolin-4-amine (10 mg, 0.04 mmol) was suspended in 10 mL of dichloromethane in a threaded test tube. The acid (0.05 mmol) was added and the mixture was briefly vortexed. To the mixture was added 1-[3-(dimethylamino)propyl]-3-ethylcarbodiimide hydrochloride (EDC, 10 mg, 0.05 mmol) and the mixture was shaken overnight at ambient temperature. To the tube was added about 90 mg of aminomethylpolystrene resin (Bachem, ~1 meq/g, 100–200 mesh) and the mixtures were heated to reflux and shaken overnight. The mixture was then filtered to remove the resin, and was purified by semi-preparative reversed-phase HPLC (Rainin Microsorb C18 column, 21.4×250 mm, 8 micron particle size, 60A pore, 10 mL/min., gradient elution from 2–95% B in 25 min., hold at 95% B for 5 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired amide. The compounds were analyzed by LC-MS (APCI).

| Example Number | Structure of Free Base | Observed Mass |
|---|---|---|
| 109 | | 464.18 |
| 110 | | 364.15 |
| 111 | | 427.98, 429.97 |
| 112 | | 323.19 |

-continued
| Example Number | Structure of Free Base | Observed Mass |
|---|---|---|
| 113 | 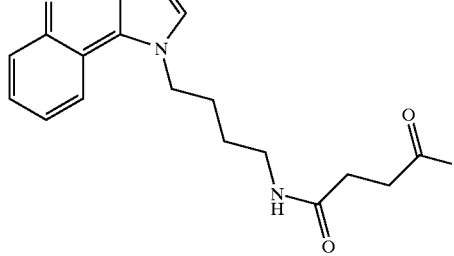 | 370.18 |
| 114 | 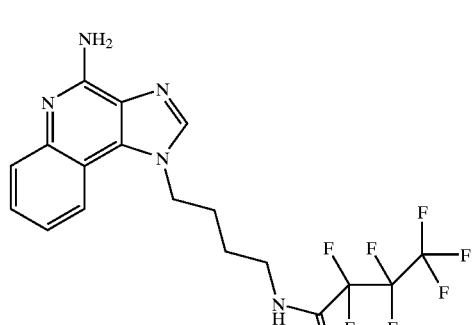 | 452.10 |
| 115 | 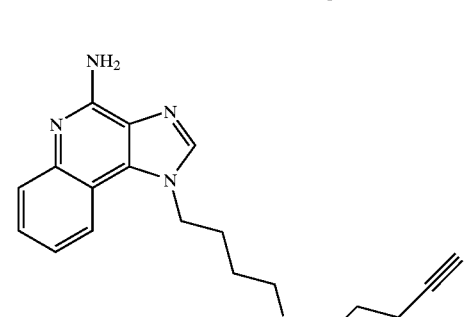 | 336.16 |
| 116 | 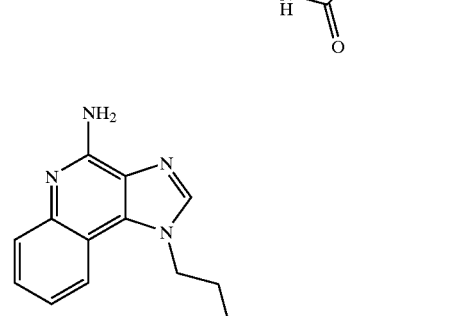 | 338.20 |

-continued

| Example Number | Structure of Free Base | Observed Mass |
| --- | --- | --- |
| 117 | (structure) | 384.20 |
| 118 | (structure) | 368.28 |
| 119 | (structure) | 420.30 |

EXAMPLES 120–146

The examples in the table below were prepared using the synthetic method described in Reaction Scheme V above.

Part A 1-(4-Aminobutyl)-1H-imidazo[4,5-c]quinolin-4-amine (25 mg, 0.1 mmol) was suspended in 5 mL of dichloromethane in a threaded test tube and the aldehyde (about 0.1 mmol) was added. The mixture was heated to reflux and was vortexed at 500 rpm for half an hour. The mixture was allowed to cool for a few minutes and then sodium triacetoxyborohydride (38 mg, 0.18 mmol) was added. The mixture was shaken at ambient temperature for 3 days, then was quenched with 0.5 mL of methanol and evaporated to dryness. The mixture was purified by semi-preparative reversed-phase HPLC (Rainin Microsorb C1 8 column, 21.4×250 mm, 8 micron particle size, 60Å pore, 10 mL/min., gradient elution from 2–95% B in 25 min., hold at 95% B for 5 min., where A=0. 1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired secondary amine. The compounds were analyzed by LC-MS (APCI).

Part B

The secondary amines from Part A (about 3–30 μmol as the di-trifluoroacetate salt) were each dissolved in 1 mL of pyridine, and about 10 equivalents of a 0.1 M solution of acetic anhydride in dichloromethane was added. The mixtures were allowed to stand for 1 hour and then 200 μL of methanol was added. The mixtures were evaporated to dryness in a vacuum centrifuge. The mixtures were purified by semi-preparative reversed-phase HPLC as in Part A. The compounds were analyzed by LC-MS (APCI).

| Example Number | Structure of Free Base | Observed Mass |
|---|---|---|
| 120 | 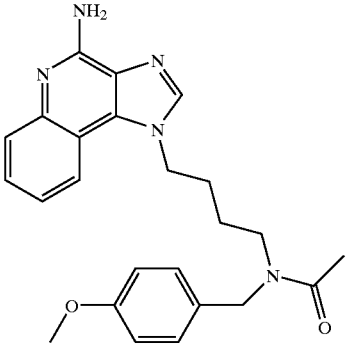 | 418.1 |
| 121 | 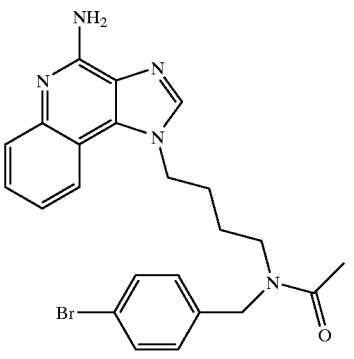 | 466.0, 468.0 |
| 122 | 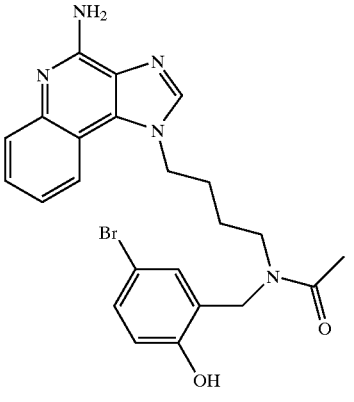 | 482.0, 484 |
| 123 | 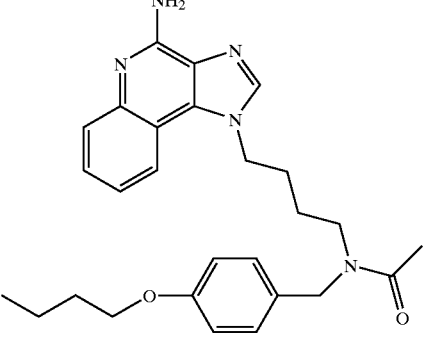 | 460.1 |

-continued
| Example Number | Structure of Free Base | Observed Mass |
| --- | --- | --- |
| 124 | 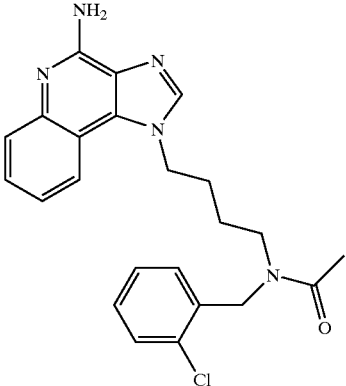 | 422.0 |
| 125 | 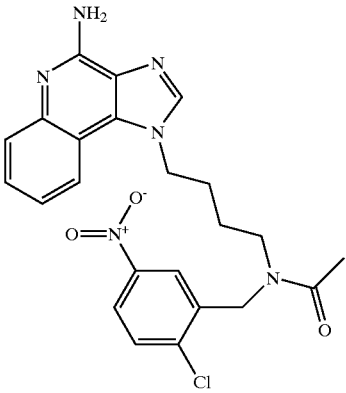 | 467.0, 469.0 |
| 126 | 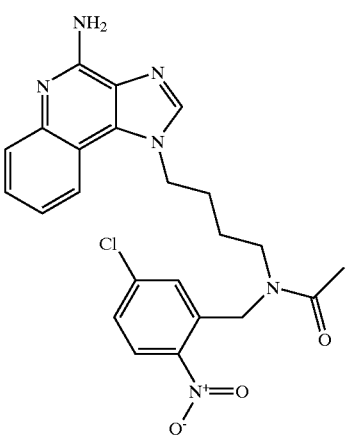 | 467.0, 469.0 |

-continued
| Example Number | Structure of Free Base | Observed Mass |
|---|---|---|
| 127 | 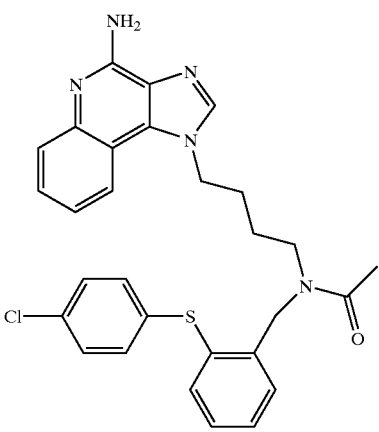 | 530.0 |
| 128 | 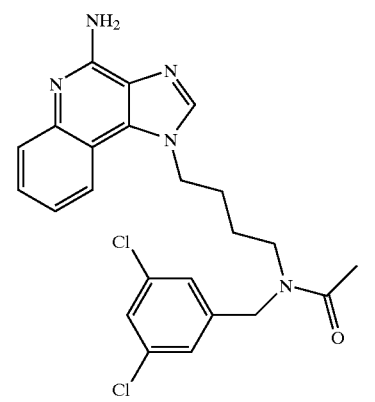 | 456.0, 458.0 |
| 129 | 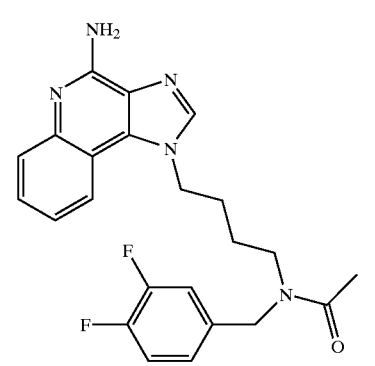 | 424.0 |

-continued

| Example Number | Structure of Free Base | Observed Mass |
|---|---|---|
| 130 | | 448.1 |
| 131 | | 448.1 |
| 132 | | 416.1 |

-continued

| Example Number | Structure of Free Base | Observed Mass |
|---|---|---|
| 133 | | 406.1 |
| 134 | | 378.0 |
| 135 | | 378.0 |
| 136 | | 416.1 |

-continued
| Example Number | Structure of Free Base | Observed Mass |
|---|---|---|
| 137 | 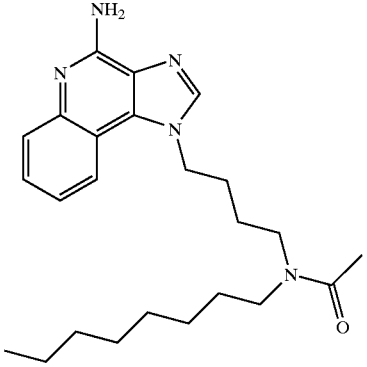 | 410.0 |
| 138 | 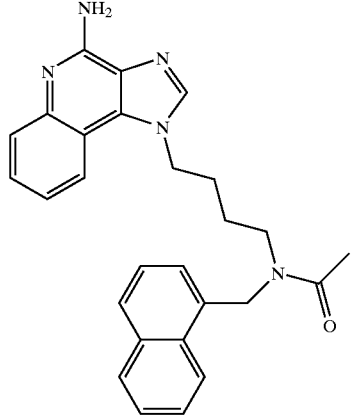 | 438.0 |
| 139 | 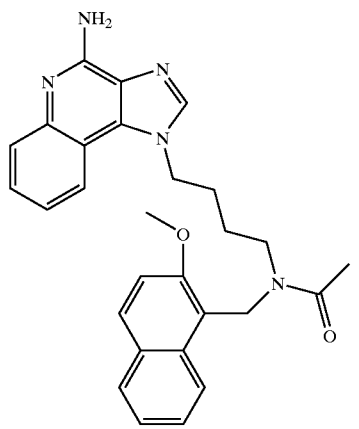 | 468.1 |

-continued
| Example Number | Structure of Free Base | Observed Mass |
|---|---|---|
| 140 | 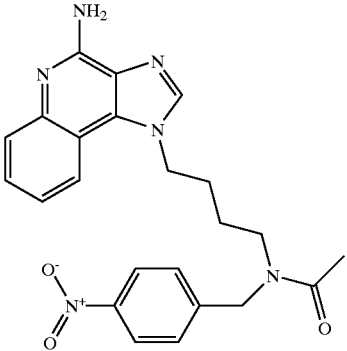 | 433.0 |
| 141 | 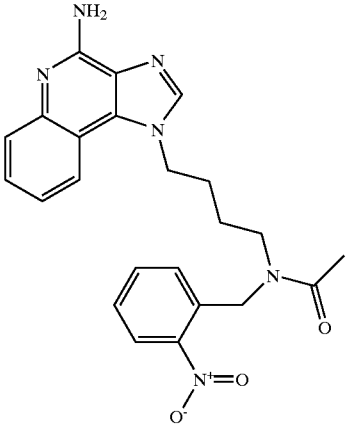 | 433.0 |
| 142 | 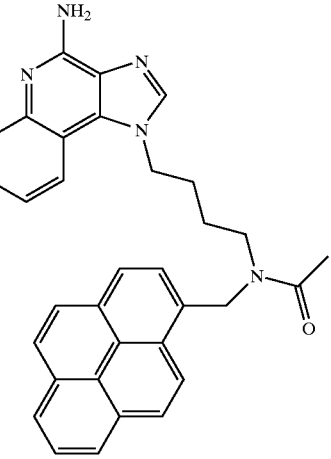 | 512.0 |

-continued
| Example Number | Structure of Free Base | Observed Mass |
|---|---|---|
| 143 | 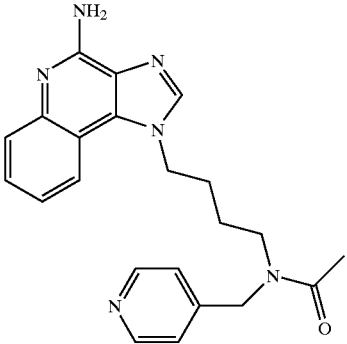 | 389.0 |
| 144 | 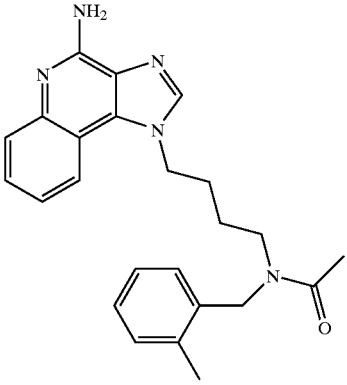 | 402.1 |
| 145 | 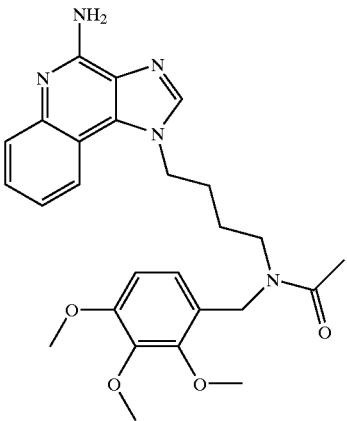 | 478.1 |

| Example Number | Structure of Free Base | Observed Mass |
|---|---|---|
| 146 | 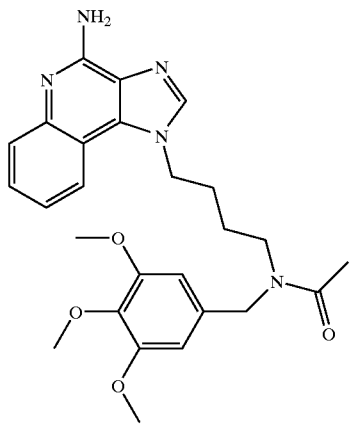 | 478.1 |

EXAMPLES 147–159

The compounds in the table below were prepared using the synthetic method of Reaction Scheme II above.

1-(4-Aminobutyl)-2-methoxyethyl-1H-imidazo[4,5-c]quinolin-4-amine (50 mg) was placed in a 2 dram (7.4 mL) vial. Diisopropylethylamine (1.2 eq) and dichloromethane (1 mL) were added. A solution containing the carboxylic acid chloride (1.1 eq) in dichloromethane (1 mL) was added. The vial was placed on a shaker for about 2 hours at ambient temperature. The reaction mixture was analyzed by LC/MS to confirm the formation of the desired product. The solvent was removed and the residue was purified by semi-preparative HPLC (Capcell PakC 18 column, 35×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired amide.

| Example # | Structure of the Free Base | APCI-MS m/e |
|---|---|---|
| 147 | | 384.2 |

-continued
| Example # | Structure of the Free Base | APCI-MS m/e |
|---|---|---|
| 148 | 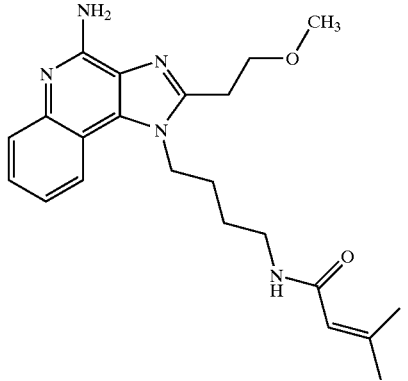 | 396.2 |
| 149 | 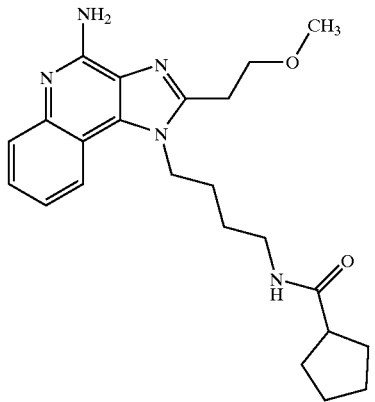 | 410.2 |
| 150 | 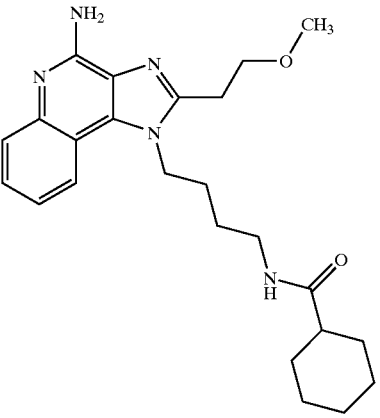 | 424.2 |

-continued
| Example # | Structure of the Free Base | APCI-MS m/e |
|---|---|---|
| 151 | 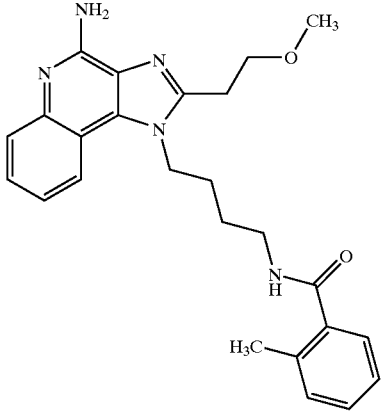 | 432.2 |
| 152 | 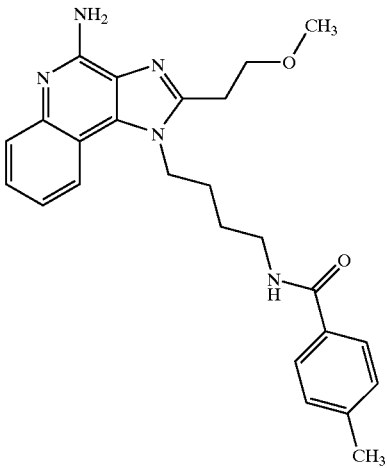 | 432.3 |
| 153 | 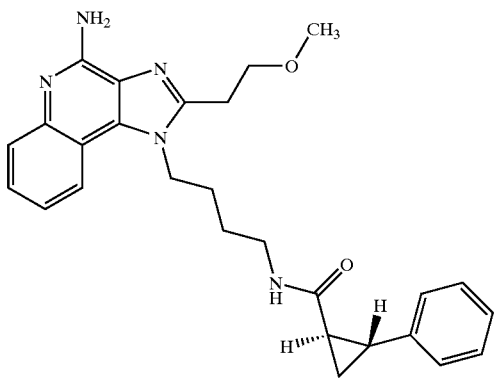 | 458.2 |

-continued

| Example # | Structure of the Free Base | APCI-MS m/e |
|---|---|---|
| 154 | | 468.2 |
| 155 | | 468.2 |
| 156 | | 474.2 |

-continued

| Example # | Structure of the Free Base | APCI-MS m/e |
|---|---|---|
| 157 | | 476.3 |
| 158 | | 478.3 |
| 159 | | 484.30 |

EXAMPLES 160–168

The compounds in the table below were prepared using the synthetic method of Reaction Scheme III above.

1-(4-Aminobutyl)-2-methoxyethyl-1H-imidazo[4,5-c]quinolin-4-amine (50 mg), the carboxylic acid (1.0 eq.) and dichloromethane (3 mL) were placed in a 2 dram (7.4 mL) vial. A solution containing 1-[3-(dimethylamino)propyl]-3-ethylcarbodiimide hydrochloride (1.1 eq) in dichloromethane (1 mL) was added. The vial was placed on a shaker for about 2 hours at ambient temperature. The reaction mixture was analyzed by LC/MS to confirm the formation of the desired product. The solvent was removed and the residue was purified by semi-preparative HPLC (Capcell Pak C18 column, 35×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired amide.

| Example # | Structure of Free Base | APCI-MS m/e |
|---|---|---|
| 160 | 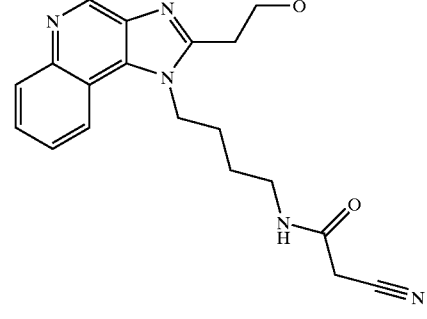 | 381.2 |
| 161 | 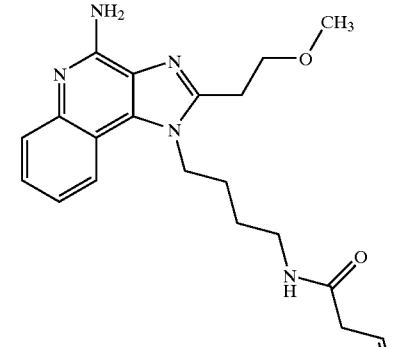 | 382.2 |
| 162 | 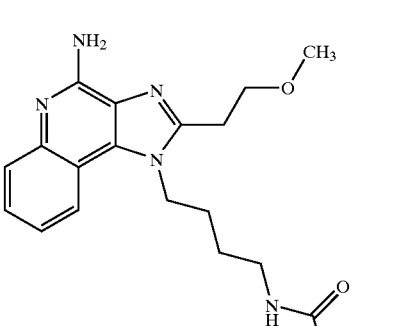 | 408.3 |

-continued

| Example # | Structure of Free Base | APCI-MS m/e |
|---|---|---|
| 163 | 4-amino-2-(2-methoxyethyl)-1-[4-(5-oxohexanamido)butyl]-1H-imidazo[4,5-c]quinoline | 426.2 |
| 164 | 4-amino-2-(2-methoxyethyl)-1-{4-[(2E)-3-(furan-3-yl)prop-2-enamido]butyl}-1H-imidazo[4,5-c]quinoline | 434.2 |
| 165 | 4-amino-2-(2-methoxyethyl)-1-{4-[(2E)-4-ethoxy-4-oxobut-2-enamido]butyl}-1H-imidazo[4,5-c]quinoline | 440.2 |

-continued
| Example # | Structure of Free Base | APCI-MS m/e |
|---|---|---|
| 166 | 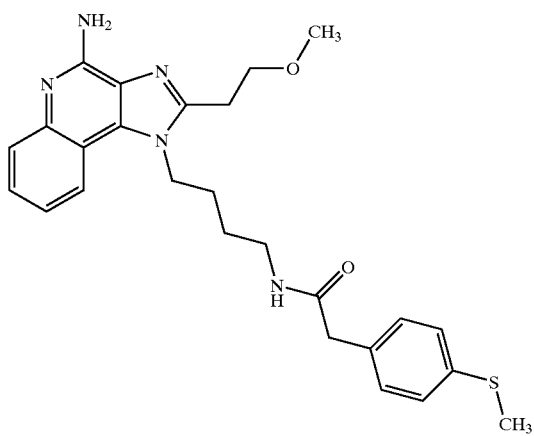 | 478.2 |
| 167 | 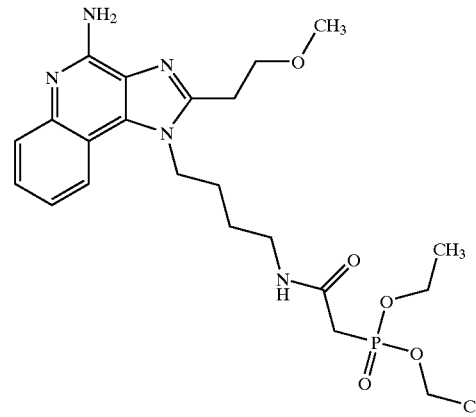 | 492.3 |
| 168 | 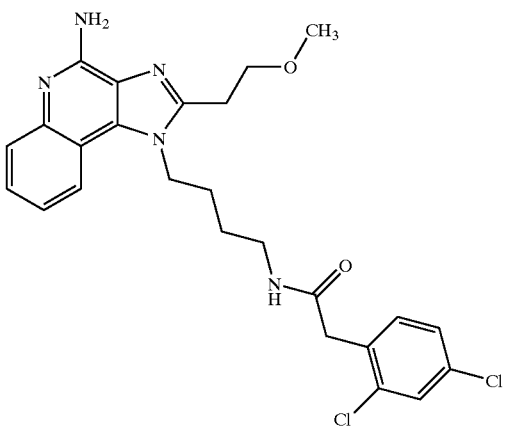 | 500.2, 502.2 |

EXAMPLE 169

$N^1$-[4-(4-Amino-2-(4-methoxybenzyl)-1H-imidazo[4,5-c]quinolin-1yl)butyl]acetamide Trifluoroacetate

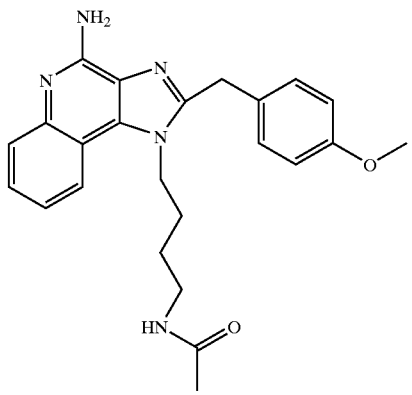

Using the method of Examples 147–159 above, 1-(4-aminobutyl)-2-(4-methoxybenzyl)-1H-imidazo[4,5-c]quinolin-4-amine was reacted with acetyl chloride to provide $N^1$-[4-(4-amino-2-(4-methoxybenzyl)-1H-imidazo[4,5-c]quinolin-1-yl)butyl]acetamide Trifluoroacetate. APCI-MS m/e 418.2.

EXAMPLES 170 & 171

The examples in the table below were prepared by reacting 1-(4-aminobutyl)-2-(4-methoxybenzyl)-1H-imidazo[4,5-c]quinolin-4-amine with the appropriate carboxylic acid using the method of Example 160–168.

| Example # | Structure of the Free Base | APCI-MS m/e |
|---|---|---|
| 170 | | 481.2 |
| 171 | | 481.2 |

EXAMPLES 172–174

The examples in the table below were prepared according to the synthetic method described in Reaction Scheme VI above.

Part A

A catalytic amount of platinum (IV) oxide was added to a solution of 1-(4-aminobutyl)-2-methoxyethyl-1H-imidazo[4,5-c]quinolin-4-amine (7.7 g, 24.5 mmol) in trifluoroacetic acid (250 mL). The reaction mixture was hydrogenated at 50 psi ($3.44 \times 10^5$ Pa) on a Parr apparatus. The progress of the reaction was monitored by LC/MS. Additional catalyst was added 7, 11, and 17 days after the start of the reaction. After 25 days the reaction was complete. The reaction mixture was filtered through a layer of Celite® filter aid to remove the catalyst and the filtrate was concentrated under vacuum. The residue was combined with 1 N hydrochloric acid (100 mL) and stirred overnight. The mixture was made basic (pH=11) with ammonium hydroxide and then extracted with dichloromethane (3×300 mL). The extracts were combined and concentrated under vacuum to provide 3.5 g of 1-(4-aminobutyl)-6,7,8,9-tetrahydro-2-methoxyethyl-1H-imidazo[4,5-c]quinolin-4-amine as a solid.

Part B

Using the method of Examples DC 147–159 above. The material from Part A was reacted with the appropriate acid chloride to give the desired amide.

| Example # | Structure of the Free Base | APCI-MS m/e |
|---|---|---|
| 172 | | 422.2 |
| 173 | | 423.1 |
| 174 | | 436.2 |

EXAMPLES 175–180

The examples in the table below were prepared according to the synthetic method of Reaction Scheme III above using the general method of Examples 160–168.

| Example # | Structure of the Free Base | mass |
|---|---|---|
| 175 | | 408.2 |
| 176 | | 419.1 |
| 177 | | 438.2 |
| 178 | | 446.2 |

-continued

| Example # | Structure of the Free Base | mass |
|---|---|---|
| 179 | | 453.2 |
| 180 | | 480.2 |

CYTOKINE INDUCTION IN HUMAN CELLS

An in vitro human blood cell system was used to assess cytokine induction by compounds of the invention. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood is collected by venipuncture into EDTA vacutainer tubes from healthy human donors. Peripheral blood mononuclear cells (PBMCs) are separated from whole blood by density gradient centrifugation using Histopaque®-1077 (Sigma Chemicals, St. Louis, Mo.). The PBMCs are suspended at 3–4×10$^6$ cells/mL in RPMI 1640 medium containing 10% fetal bovine serum, 2 mM L-glutamine and 1% penicillin/streptomycin solution (RPMI complete). The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells.

Incubation

The solution of test compound is added at 60 μM to the first well containing RPMI complete and serial (three fold or ten fold) dilutions are made. The PBMC suspension is then added to the wells in an equal volume, bringing the test compound concentrations to the desired range. The final concentration of PBMC suspension is 1.5–2×10$^6$ cells/mL.

The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200×g) at 4° C. The cell culture supernatant is removed with a sterile polypropylene pipet and transferred to sterile polypropylene tubes. Samples are maintained at −30 to −70° C. until analysis. The samples are analyzed for interferon (α) by either ELISA or bioassay and for tumor necrosis factor (α) by ELISA.

Interferon Bioassay Analysis

Interferon is determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates", Biotechniques, June/July, 78, 1983, incorporated herein by reference. Briefly stated the method is as follows: A549 cells are incubated with dilutions of samples or a standard interferon at 37° C. for 24 hours. The incubated cells are then infected with an inoculum of encephalomyocarditis virus. The infected cells are incubated for an additional 24 hours at 37° C. before evaluating for viral cytopathic effect. The viral cytopathic effect is quantified by staining with crystal violet followed by visual scoring of the plates. Results are expressed as alpha reference units/mL based on the value obtained for NIH Human Leukocyte IFN standard.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J.

Tumor necrosis factor (α) (TNF)concentration is determined using ELISA kits available from Genzyme, Cambridge, Mass.; R&D Systems, Minneapolis, Minn.; or Pharmingen, San Diego, Calif.

The table below lists the lowest concentration found to induce interferon and the lowest concentration found to induce tumor necrosis factor for each compound. A "" indicates that no induction was seen at any of the tested concentrations (0.12, 0.37, 1.11, 3.33, 10 and 30 $\mu$M). A "*" indicates that no induction was seen at any of the tested concentrations (0.0001, 0.001, 0.01, 0.1, 1 and 10 $\mu$M). Unless otherwise indicated, the interferon biosynthesis was determined by ELISA.

Cytokine Induction in Human Cells

| Example Number | Lowest Effective Concentration ($\mu$M) | |
|---|---|---|
| | Interferon | Tumor Necrosis Factor |
| 1 | 0.37 | 10 |
| 3 | 0.37 | 1.11 |
| 4 | 0.04 | 0.37 |
| 5 | 0.04 | 0.37 |
| 6 | 0.12 | 1.11 |
| 7 | 1.11 | ** |
| 8 | 0.04 | ** |
| 9 | 0.37 | 3.33 |
| 10 | 3.33 | ** |
| 11 | 1.11 | ** |
| 12 | 3.33 | ** |
| 13 | 1.11 | 3.33 |
| 14 | 3.33 | ** |
| 15 | 3.33 | ** |
| 16 | 1.11 | 30 |
| 17 | 3.33 | 10 |
| 18 | 3.33 | ** |
| 19 | 10 | ** |
| 20 | 3.33 | ** |
| 21 | 0.12 | 1.11 |
| 22 | 0.37 | 10 |
| 23 | 1.11 | ** |
| 24 | 0.12 | 3.33 |
| 25 | 3.33 | ** |
| 26 | 0.37 | 10 |
| 27 | ** | ** |
| 28 | 0.12 | ** |
| 29 | 0.12 | ** |
| 31 | 1.11 | ** |
| 32 | 3.33 | ** |
| 33 | 0.37 | ** |
| 34 | ** | 3.33 |
| 35 | 1.11 | ** |
| 36 | 1.11 | 10 |
| 37 | 0.37 | ** |
| 38 | 0.12 | 3.33 |
| 39 | 3.33 | ** |
| 40 | 0.37 | 30 |
| 41 | 1.11 | ** |
| 42 | 30 | 3.33 |
| 43 | 0.12 | ** |
| 44 | 1.11 | ** |
| 45 | 3.33 | ** |
| 46 | ** | 10 |
| 68* | 1.11 | 10 |
| 69* | 0.12 | 1.11 |
| 70* | 0.37 | 3.33 |
| 71* | 0.12 | 3.33 |
| 72* | 0.37 | 10 |
| 73* | 0.37 | 10 |
| 74* | 0.37 | 10 |
| 75* | 1.11 | ** |
| 76* | 3.33 | ** |
| 77* | 1.11 | 10 |
| 78* | 0.12 | 10 |
| 79* | 0.37 | ** |
| 80* | 1.11 | 10 |
| 81* | 3.33 | 30 |
| 82* | 0.12 | 10 |
| 83* | 1.11 | ** |
| 84* | 0.12 | 10 |
| 85 | 1.11 | 10 |
| 86 | 1.11 | 10 |
| 87 | 3.33 | 30 |
| 88 | 10 | ** |
| 89 | 1.11 | 10 |
| 90 | 3.33 | 10 |
| 91 | 3.33 | ** |
| 92 | 3.33 | ** |
| 93 | 1.11 | 30 |
| 94 | 0.04 | 3.33 |
| 95 | 3.33 | 30 |
| 96 | 0.37 | 10 |
| 97 | 0.12 | 3.33 |
| 98 | 1.11 | 10 |
| 99 | 0.37 | 3.33 |
| 100 | 10 | 3.33 |
| 101 | 3.33 | ** |
| 102 | 3.33 | ** |
| 103 | 0.37 | 10 |
| 104 | ** | ** |
| 105 | 0.12 | 10 |
| 106 | 3.33 | ** |
| 107 | 0.12 | 10 |
| 108 | 0.12 | 10 |
| 109 | ** | ** |
| 110 | 1.11 | 3.33 |
| 111 | 1.11 | ** |
| 112 | 10 | ** |
| 113 | 3.33 | ** |
| 114 | 1.11 | 10 |
| 115 | 1.11 | 30 |
| 116 | 0.37 | 10 |
| 117 | 3.33 | ** |
| 118 | 1.11 | ** |
| 119 | ** | ** |
| 120 | 0.37 | ** |
| 121 | 1.11 | ** |
| 122 | 3.33 | ** |
| 123 | 3.33 | ** |
| 124 | 1.11 | 3.33 |
| 125 | 1.11 | ** |
| 126 | 3.33 | ** |
| 127 | ** | ** |
| 128 | 3.33 | 1.11 |
| 129 | 3.33 | ** |
| 130 | 1.11 | 10 |
| 131 | 3.33 | ** |
| 132 | 1.11 | 3.33 |
| 133 | 3.33 | ** |
| 134 | 0.37 | ** |
| 135 | 0.12 | ** |
| 136 | 1.11 | ** |
| 137 | 10 | ** |
| 138 | 1.11 | ** |
| 139 | ** | ** |
| 140 | 1.11 | ** |
| 141 | 0.37 | ** |
| 142 | 3.33 | ** |
| 143 | 0.12 | ** |
| 144 | 1.11 | ** |
| 145 | 1.11 | ** |
| 146 | 3.33 | ** |
| 148 | 0.01 | 1 |
| 149 | 0.001 | 1 |
| 150 | 0.001 | 0.1 |
| 151 | 0.0001 | *** |
| 153 | 0.0001 | 0.1 |
| 154 | 0.0001 | *** |
| 155 | 0.0001 | 1 |
| 155 | 0.01 | 0.1 |
| 156 | 0.001 | 1 |

-continued

Cytokine Induction in Human Cells

| Example Number | Lowest Effective Concentration (μM) | |
|---|---|---|
| | Interferon | Tumor Necrosis Factor |
| 158 | 0.001 | 1 |
| 159 | 0.01 | 1 |
| 172 | 0.0001 | 1 |
| 173 | 0.001 | 1 |
| 174 | 0.001 | 1 |

*Interferon determined using the bioassay method

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. A pharmaceutical composition comprising a therapeutically effective amount of a compound of the formula (I):

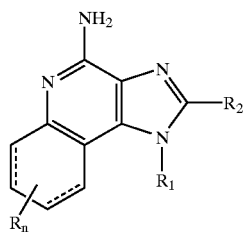

wherein
  $R_1$ is -alkyl-$NR_3$—CO—$R_4$ or -alkenyl-$NR_3$—CO—$R_4$ wherein R4 is aryl, heteroaryl, alkyl or alkenyl, each of which may be unsubstituted or substituted by one or more substituents selected from the group consisting of:
  -alkyl;
  -alkenyl;
  -alkynyl;
  -(alkyl)$_{0-1}$-aryl;
  -(alkyl)$_{0-1}$-(substituted aryl);
  -(alkyl)$_{0-1}$-heteroaryl;
  -(alkyl)$_{0-1}$-(substituted heteroaryl);
  —O-alkyl;
  —O-(alkyl)$_{0-1}$-aryl;
  —O-(alkyl)$_{0-1}$-(substituted aryl);
  —O-(alkyl)$_{0-1}$-heteroaryl;
  —O-(alkyl)$_{0-1}$-(substituted heteroaryl);
  —CO-aryl;
  —CO-(substituted aryl);
  —CO-heteroaryl;
  —CO-(substituted heteroaryl);
  —COOH;
  —CO—O-alkyl;
  —CO-alkyl;
  —S(O)$_{0-2}$-alkyl;
  —S(O)$_{0-2}$-(alkyl)$_{0-1}$-aryl;
  —S(O)$_{0-2}$-(alkyl)$_{0-1}$-(substituted aryl);
  —S(O)$_{0-2}$-(alkyl)$_{0-1}$-heteroaryl;
  —S(O)$_{0-2}$-(alkyl)$_{0-1}$-(substituted heteroaryl);
  —P(O)(OR$_3$)$_2$;
  —NR$_3$—CO—O-alkyl;
  —N$_3$;
  -halogen;
  —NO$_2$;
  —CN;
  -haloalkyl;
  —O-haloalkyl;
  —CO-haloalkyl;
  —OH;
  —SH; and if $R_4$ is alkyl or alkenyl, then the substituent can also be oxo; or $R_4$ is

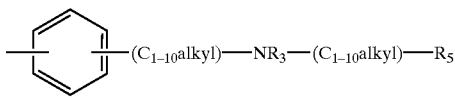

wherein $R_5$ is an aryl, (substituted aryl), heteroaryl, (substituted heteroaryl), heterocyclyl or (substituted heterocyclyl) group;
  $R_2$ is selected from the group consisting of:
  -hydrogen;
  -alkyl;
  -alkenyl;
  -aryl;
  -(substituted aryl);
  -heteroaryl;
  -(substituted heteroaryl);
  -heterocyclyl;
  -(substituted heterocyclyl);
  -alkyl-O-alkyl;
  -alkyl-O-alkenyl; and
  -alkyl or alkenyl substituted by one or more substituents selected from the group consisting of
    —OH,
    -halogen;
    —N(R$_3$)$_2$;
    —CO—N(R$_3$)$_2$;
    —CO—C$_{1-10}$ alkyl;
    —CO—O—C$_{1-10}$ alkyl;
    —N$_3$;
    -aryl;
    -(substituted aryl);
    -heteroaryl;
    -(substituted heteroaryl);
    -heterocyclyl;
    -(substituted heterocyclyl);
    —CO-aryl; and
    —CO-heteroaryl;
  each $R_3$ is independently selected from the group consisting of hydrogen; C$_{1-10}$alkyl-heteroaryl; C$_{1-10}$ alkyl-(substituted heteroaryl); C$_{1-10}$ alkyl-aryl; C$_{1-10}$ alkyl-(substituted aryl) and C$_{1-10}$ alkyl;
  n is 0 to 4;
  and each R present is independently selected from the group consisting of C$_{1-10}$ alkyl, C$_{1-10}$ alkoxy, halogen and trifluoromethyl, wherein the substituent(s) of the substituted aryl, heteroaryl, and heterocyclyl groups are independently selected from the group consisting of alkyl, alkoxy, alkylthio, hydroxy, halogen, haloalkyl, haloalkylcarbonyl, haloalkoxy, nitro, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl,

139 alkanoyloxy, alkanoylthio, and, in the case of a heterocyclyl group, oxo; or a pharmaceutically acceptable salt thereof, in combination with a pharmaceutically acceptable carrier.

2. The composition of claim 1 wherein $R_2$ is hydrogen.

3. The composition of claim 1 wherein $R_2$ is selected from the group consisting of: hydrogen; alkyl; alkyl-O-alkyl; (alkyl)$_{0-1}$aryl; and (alkyl)$_{0-1}$-(substituted aryl).

4. The composition of claim 1 wherein $R_4$ is aryl or heteroaryl that may be unsubstituted or substituted by one or more substituents selected from the group consisting of:
-alkyl;
-alkenyl;
-alkynyl;
-(alkyl)$_{0-1}$-aryl;
-(alkyl)$_{0-1}$-(substituted aryl);
-(alkyl)$_{0-1}$-heteroaryl;
-(alkyl)$_{0-1}$-(substituted heteroaryl);
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—NR$_3$—CO—O-alkyl;
—P(O)(OR$_3$)$_2$;
—N$_3$;
-halogen;
—NO$_2$;
—CN;
-haloalkyl;
—O-haloalkyl;
—CO-haloalkyl;
—OH; and
—SH.

5. The composition of claim 1 wherein $R_4$ is

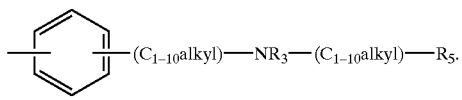

6. The composition of claim 5 wherein $R_5$ is 4-pyridyl.

7. A compound selected from the group consisting of:

$N^1$-[4-(4-Amino-1H-imidazo[4,5-c]quinolin-1-yl)butyl]-2-ethoxy-1-naphthamide;
$N^1$-[4-(4-Amino-1H-imidazo[4,5-c]quinolin-1-yl)butyl]-4-cyanobenzamide;

140

$N^1$-[4-(4-Amino-1H-imidazo[4,5-c]quinolin-1-yl)butyl]-3-cyanobenzamide;
$N^1$-[4-(4-Amino-1H-imidazo[4,5-c]quinolin-1-yl)butyl]-1-naphthamide;
$N^2$-[4-(4-Amino-1H-imidazo[4,5-c]quinolin-1-yl)butyl]-2-naphthamide;
$N^1$-{4-[4-Amino-2-(2-methoxyethyl)-1H-imidazo[4,5-c]quinolin-1-yl]butyl}-4-(1-pyrrolyl)benzamide;
$N^1$-{4-(4-Amino-2-(2-methoxyethyl)-1H-imidazo[4,5-c]quinolin-1-yl)butyl}-1-naphthamide;
$N^2$-{4-(4-Amino-2-(2-methoxyethyl)-1H-imidazo[4,5-c]quinolin-1-yl)butyl}-2-naphthamide;
$N^1$-{4-(4-Amino-2-(4-methoxybenzyl)-1H-imidazo[4,5-c]quinolin-1-yl)butyl}-1-naphthamide;
$N^2$-{4-(4-Amino-2-(4-methoxybenzyl)-1H-imidazo[4,5-c]quinolin-1-yl)butyl}-2-naphthamide;
$N^1$-[4-(4-Amino-2-butyl-1H-imidazo[4,5-c]quinolin-1-yl)butyl]-1-naphthamide;
$N^2$-[4-(4-Amino-2-butyl-1H-imidazo[4,5-c]quinolin-1-yl)butyl]-2-naphthamide;
$N^1$-[4-(4-Amino-6,7,8,9-tetrahydro-1H-imidazo[4,5-c]quinolin-1-yl)butyl]-1-naphthamide; and
$N^2$-[4-(4-Amino-6,7,8,9-tetrahydro-1H-imidazo[4,5-c]quinolin-1-yl)butyl]-2-naphthamide.

8. A pharmaceutical composition comprising a therapeutically effective amount of a compound of the formula (Ib):

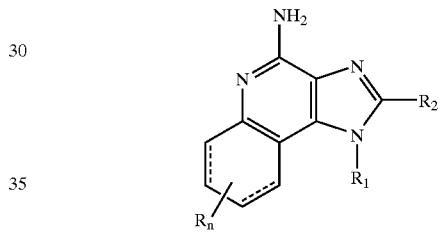

(Ib)

wherein $R_1$ is -alkyl-NR$_3$—CO—R$_4$ or -alkenyl-NR$_3$—CO—R$_4$ wherein R$_4$ is heterocyclyl which may be unsubstituted or substituted by one or more substituents selected from the group consisting of:
-alkyl;
-alkenyl;
-alkynyl;
-(alkyl)$_{0-1}$-aryl;
-(alkyl)$_{0-1}$-(substituted aryl);
-(alkyl)$_{0-1}$-heterocyclyl;
-(alkyl)$_{0-1}$-(substituted heterocyclyl);
-(alkyl)$_{0-1}$-heteroaryl;
-(alkyl)$_{0-1}$-(substituted heteroaryl);
—O-alkyl;
—O-(alkyl)$_{0-1}$-aryl;
—O-(alkyl)$_{0-1}$-(substituted aryl);
—O-(alkyl)$_{0-1}$-heterocyclyl;
—O-(alkyl)$_{0-1}$-(substituted heterocyclyl);
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;

—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heterocyclyl;
—S(O)$_{0-2}$-(alkyl)$_{0-1}$-(substituted heterocyclyl);
—S(O)$_{0-2}$-(alkyl)$_{0-1}$-heteroaryl;
—S(O)$_{0-2}$-(alkyl)$_{0-1}$-(substituted heteroaryl);
—P(O)(OR$_3$)$_2$;
—NR$_3$—CO—O-alkyl;
—N$_3$;
oxo;
-halogen;
—NO$_2$;
—CN;
-haloalkyl;
—O-haloalkyl;
—CO-haloalkyl;
—OH; and
—SH; or R$_4$ is

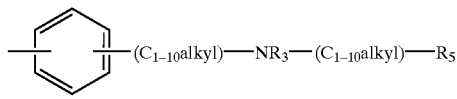

wherein R$_5$ is an aryl, (substituted aryl), heteroaryl, (substituted heteroaryl), heterocyclyl or (substituted heterocyclyl) group;

R$_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl;
-alkyl-O-alkenyl; and
-alkyl or alkenyl substituted by one or more substituents selected from the group consisting of:
  —OH;
  -halogen;
  —N(R$_3$)$_2$;
  —CO—N(R$_3$)$_2$;
  —CO—C$_{1-10}$ alkyl;
  —CO—O—C$_{1-10}$ alkyl;
  —N$_3$;
  -aryl;
  -(substituted aryl);
  -heteroaryl;
  -(substituted heteroaryl);
  -heterocyclyl;
  -(substituted heterocyclyl);
  —CO-aryl; and
  —CO-heteroaryl;

each R$_3$ is independently selected from the group consisting of hydrogen; C$_{1-10}$ alkyl-heteroaryl; C$_{1-10}$ alkyl-(substituted heteroaryl); C$_{1-10}$ alkyl-aryl; C$_{1-10}$ alkyl-(substituted aryl) and C$_{1-10}$ alkyl;

n is 0 to 4;

and each R present is independently selected from the group consisting of C$_{1-10}$ alkyl, C$_{1-10}$ alkoxy, halogen and trifluoromethyl, or a pharmaceutically acceptable salt thereof, in combination with a pharmaceutically acceptable carrier.

9. A compound of the formula (Ic):

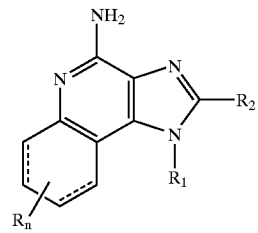

(Ic)

wherein

R$_1$ is -alkyl-NR$_3$—CO—R$_4$ or -alkenyl-NR$_3$—CO—R$_4$ wherein R$_4$ is aryl, heteroaryl, heterocyclyl, alkyl or alkenyl, each of which may be unsubstituted or substituted by one or more substituents selected from the group consisting of:
-alkyl;
-alkenyl;
-alkynyl;
-(alkyl)$_{0-1}$-aryl;
-(alkyl)$_{0-1}$-(substituted aryl);
-(alkyl)$_{0-1}$-heteroaryl;
-(alkyl)$_{0-1}$-(substituted heteroaryl);
-(alkyl)$_{0-1}$-heterocyclyl;
-(alkyl)$_{0-1}$-(substituted heterocyclyl);
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—O-(alkyl)$_{0-1}$-heterocyclyl;
—O-(alkyl)$_{0-1}$-(substituted heterocyclyl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—S(O)$_{0-2}$-(alkyl)$_{0-1}$-heterocyclyl;
—S(O)$_{0-2}$-(alkyl)$_{0-1}$-(substituted heterocyclyl);
—NR$_6$—CO—O-alkyl;
—P(O)(OR$_3$)$_2$;
—N$_3$;
-halogen;
—NO$_2$;
—CN;
-haloalkyl;
—O-haloalkyl;
—CO-haloalkyl;
—OH;
—SH; and in the case of alkyl, alkenyl, or heterocyclyl, oxo;

or $R_4$ is

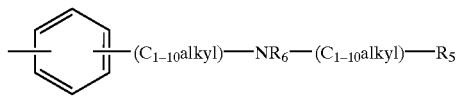

wherein $R_5$ is an aryl, (substituted aryl), heteroaryl, (substituted heteroaryl), heterocyclyl or (substituted heterocyclyl) group;

$R_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl;
-alkyl-O-alkenyl; and
-alkyl or alkenyl substituted by one or more substituents selected from the group consisting of:
—OH;
-halogen;
—N($R_6$)$_2$;
—CO—N($R_6$)$_2$; —CO—$C_{1-10}$ alkyl; —CO—O—$C_{1-10}$ alkyl;
—N$_3$;
-aryl;
-(substituted aryl);
-heteroaryl;
-(substituted heteroaryl);
-heterocyclyl;
-(substituted heterocyclyl);
—CO-aryl; and
—CO-heteroaryl;

$R_3$ is selected from the group consisting of $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

each $R_6$ is independently selected from the group consisting of hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

n is 0 to 4;

and each R present is independently selected from the group consisting of $C_{1-10}$ alkyl, $C_{1-10}$ alkoxy, halogen and trifluoromethyl, wherein the substituent(s) of the substituted aryl, heteroaryl, and heterocyclyl groups are independently selected from the group consisting of alkyl, alkoxy, alkylthio, hydroxy, halogen, haloalkyl, haloalkylcarbonyl, haloalkoxy, nitro, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, alkanoylthio, and, in the case of a heterocyclyl group, oxo; or a pharmaceutically acceptable salt thereof.

10. A compound of claim 9 wherein the dashed bonds are absent.

11. A compound of claim 9 wherein $R_3$ is selected from the group consisting of $C_{1-10}$ alkyl-heteroaryl; $C_{1-10}$ alkyl-(substituted heteroaryl); $C_{1-10}$ alkyl-aryl; and $C_{1-10}$ alkyl-(substituted aryl).

12. A compound of claim 9 wherein $R_3$ is selected from the group consisting of $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{6-10}$ alkyl.

13. A compound of claim 9 wherein $R_3$ is selected from the group consisting of 2-methoxybenzyl; 2-furylmethyl; 3-furylmethyl; 2-nitrobenzyl; and 4-pyridylmethyl.

14. A compound of claim 13 wherein $R_2$ is hydrogen and $R_4$ is methyl.

15. A compound of claim 9 wherein n is 0.

16. A compound of claim 9 wherein $R_2$ is selected from the group consisting of hydrogen; alkyl; alkyl-O-alkyl; (alkyl)$_{0-1}$ aryl, (alkyl)$_{0-1}$-(substituted aryl); (alkyl)$_{0-1}$-heteroaryl; and (alkyl)$_{0-1}$-(substituted heteroaryl).

17. A compound of claim 9 wherein $R_2$ is selected from the group consisting of hydrogen; $C_{1-4}$ alkyl; and $C_{1-4}$alkyl-O—$C_{1-4}$alkyl.

18. A compound of claim 9 wherein $R_1$ is —(CH$_2$)$_{1-6}$—NR$_3$—CO—R$_4$—.

19. A compound of claim 9 wherein $R_4$ is naphthyl that may be unsubstituted or substituted by one or more substituents selected from the group consisting of:
-alkyl;
-alkenyl;
-alkynyl;
-(alkyl)$_{0-1}$-aryl;
-(alkyl)$_{0-1}$-(substituted aryl);
-(alkyl)$_{0-1}$-heteroaryl;
-(alkyl)$_{0-1}$-(substituted heteroaryl);
—O-alkyl,
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—CO—O-alkyl;
—CO-alkyl;
—COOH;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—NR$_3$—CO—O-alkyl;
—P(O)(OR$_3$)$_2$;
—N$_3$;
oxo;
-halogen;
—NO$_2$;
—CN;
-haloalkyl;
—O-haloalkyl;
—CO-haloalkyl;
—OH; and
—SH.

20. A compound of the formula (Id):

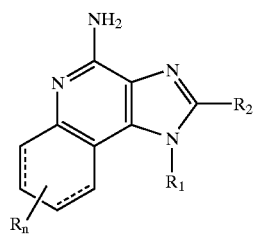

wherein
$R_1$ is -alkyl-$NR_3$—CO—$R_4$ or -alkenyl-$NR_3$—CO—$R_4$ wherein $R_4$ is aryl or heteroaryl which may be unsubstituted or substituted by one or more substituents selected from the group consisting of:
-alkyl;
-alkenyl;
-alkynyl;
-(alkyl)$_{0-1}$-aryl;
-(alkyl)$_{0-1}$-(substituted aryl);
-(alkyl)$_{0-1}$-heteroaryl;
-(alkyl)$_{0-1}$-(substituted heteroaryl);
-(alkyl)$_{0-1}$-heterocyclyl;
-(alkyl)$_{0-1}$-(substituted heterocyclyl);
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—O-(alkyl)$_{0-1}$-heterocyclyl;
—O-(alkyl)$_{0-1}$-(substituted heterocyclyl);
—CO-aryl;
—CO-(substituted aryl);
—CO-heteroaryl;
—CO-(substituted heteroaryl);
—CO—O-alkyl;
—COOH;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—S(O)$_{0-2}$-(alkyl)$_{0-1}$-heterocyclyl;
—S(O)$_{0-2}$-(alkyl)$_{0-1}$-(substituted heterocyclyl);
—$NR_3$—CO—O-alkyl;
—P(O)(O$R_3$)$_2$;
—$N_3$;
-halogen;
—$NO_2$;
—CN;
-haloalkyl;
—O-haloalkyl;
—CO-haloalkyl;
—OH; and
—SH; or $R_4$ is

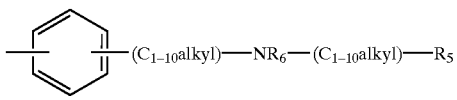

wherein $R_5$ is an aryl, (substituted aryl), heteroaryl, (substituted heteroaryl), heterocyclyl or (substituted heterocyclyl) group;

$R_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl;
-alkyl-O-alkenyl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-(substituted aryl);
-heteroaryl;
-(substituted heteroaryl);
-heterocyclyl;
-(substituted heterocyclyl);
—CO-aryl; and
—CO-heteroaryl;
each $R_3$ is independently selected from the group consisting of hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;
n is 0 to 4;
and each R present is independently selected from the group consisting of $C_{1-10}$ alkyl, $C_{1-10}$ alkoxy, halogen and trifluoromethyl, or a pharmaceutically acceptable salt thereof,
with the proviso that $R_4$ is not an unsubstituted benzene ring, and that when $R_4$ is a substituted benzene ring the substituents are selected from the group consisting of alkyl, alkoxy, alkylthio, hydroxy, haloalkyl, haloalkylcarbonyl, haloalkoxy, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, alkanoylthio, and —($C_{1-10}$alkyl)—$NR_3$—($C_{1-10}$alkyl)—$R_5$, wherein $R_5$ is an aryl, (substituted aryl), heteroaryl, (substituted heteroaryl), heterocyclyl or (substituted heterocyclyl) group.

21. A compound of claim 20 wherein n is 0.

22. A compound of claim 20 wherein $R_2$ is selected from the group consisting of hydrogen; alkyl; alkyl-O-alkyl; (alkyl)$_{0-1}$aryl; and (alkyl)$_{0-1}$-(substituted aryl).

23. A compound of claim 20 wherein $R_2$ is selected from the group consisting of hydrogen, $C_{1-4}$ alkyl, and $C_{1-4}$alkyl-O—$C_{1-4}$alkyl.

24. A compound of claim 23 wherein $R_2$ is hydrogen or methoxyethyl.

25. A compound of claim 20 wherein $R_1$ is —(CH$_2$)$_{1-6}$—$NR_3$—CO—$R_4$—.

26. A compound of claim 20 wherein $R_3$ is hydrogen.

27. A compound of claim 20 wherein $R_4$ is naphthyl, quinolinyl, isoquinolinyl or pyridyl that may be unsubstituted or substituted by one or more substituents selected from the group consisting of:
-alkyl;

-alkenyl;
-alkynyl;
-(alkyl)$_{0-1}$-aryl;
-(alkyl)$_{0-1}$-(substituted aryl);
-(alkyl)$_{0-1}$-heteroaryl;
-(alkyl)$_{0-1}$-(substituted heteroaryl);
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—NR$_3$—CO—O-alkyl;
—P(O)(OR$_3$)$_2$;
—N$_3$;
-halogen;
—NO$_2$;
—CN;
-haloalkyl;
—O-haloalkyl;
—CO-haloalkyl;
—OH; and
—SH.

28. A compound of claim 27 wherein:
R$_2$ is selected from the group consisting of hydrogen; alkyl; alkyl-O-alkyl; (alkyl)$_{0-1}$aryl; and (alkyl)$_{0-1}$-(substituted aryl);
R$_3$ is hydrogen; and
n is 0.

29. A compound of the formula (Ie):

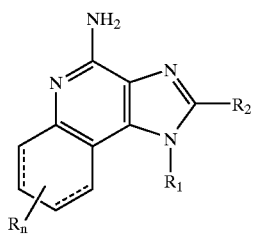

(Ie)

wherein
R$_1$ is -alkyl-NR$_3$—CO—R$_4$ or -alkenyl-NR$_3$—CO—R$_4$ wherein R$_4$ is an alkyl or alkenyl group that is substituted by one or more substituents selected from the group consisting of:
-alkynyl;
-(substituted aryl) wherein the substituent(s) is selected from the group consisting of alkyl, alkoxy, alkylthio, hydroxy, haloalkyl, haloalkylcarbonyl, haloalkoxy, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, and alkanoylthio;
-heteroaryl;
-(substituted heteroaryl);
—O-alkyl;
—O-(alkyl)$_{0-1}$-(substituted aryl) wherein the substituent(s) is selected from the group consisting of alkyl, alkoxy, alkylthio, hydroxy, haloalkyl, haloalkylcarbonyl, haloalkoxy, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, and alkanoylthio;
—O-(alkyl)$_{0-1}$-heteroaryl;
—O-(alkyl)$_{0-1}$-(substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—NR$_3$—CO—O-alkyl;
—P(O)(OR$_3$)$_2$;
—N$_3$;
oxo;
—NO$_2$;
—CN;
—O-haloalkyl;
—CO-haloalkyl;
—OH; and
—SH;

R$_2$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl -O-alkyl;
-alkyl-O-alkenyl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—N$_3$;
-aryl;
-(substituted aryl);
-heteroaryl;
-(substituted heteroaryl);
-heterocyclyl;
-(substituted heterocyclyl);

—CO-aryl; and
—CO-heteroaryl;

each $R_3$ is independently selected from the group consisting of hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

n is 0 to 4;

and each R present is independently selected from the group consisting of $C_{1-10}$ alkyl, $C_{1-10}$ alkoxy, halogen and trifluoromethyl, or a pharmaceutically acceptable salt thereof.

30. A compound of claim 29 wherein n is 0.
31. A compound of claim 29 wherein $R_2$ is selected from the group consisting of hydrogen, alkyl, alkyl-O-alkyl, (alkyl)$_{0-1}$-aryl, and (alkyl)$_{0-1}$-(substituted aryl).
32. A compound of claim 29 wherein $R_2$ is selected from the group consisting of hydrogen, $C_{1-4}$ alkyl, and $C_{1-4}$alkyl-O—$C_{1-4}$alkyl.
33. A compound of claim 29 wherein $R_2$ is hydrogen or methoxyethyl.
34. A compound of claim 33 wherein n is 0.
35. A compound of claim 33 wherein $R_3$ is hydrogen and n is 0.
36. A compound of claim 29 wherein $R_3$ is hydrogen.
37. A pharmaceutical composition comprising a therapeutically effective amount of a compound selected from the group consisting of:

$N^1$-[4-(4-Amino-1H-imidazo[4,5-c]quinolin-1-yl)butyl]benzamide;

$N^1$-[4-(4-Amino-2-propyl-1H-imidazo[4,5-c]quinolin-1-yl)butyl]benzamide;

$N^1$-[4-(4-Amino-2-methyl-1H-imidazo[4,5-c]quinolin-1-yl)butyl]benzamide;

$N^1$-[4-(4-Amino-2-ethyl-1H-imidazo[4,5-c]quinolin-1-yl)butyl]benzamide;

$N^1$-[4-(4-Amino-2-butyl-1H-imidazo[4,5-c]quinolin-1-yl)butyl]benzamide;

$N^1$-[5-(4-Amino-2-methyl-1H-imidazo[4,5-c]quinolin-1-yl)pentyl]benzamide;

$N^1$-[5-(4-Amino-1H-imidazo[4,5-c]quinolin-1-yl)pentyl]benzamide;

$N^1$-[3-(4-Amino-1H-imidazo[4,5-c]quinolin-1-yl)propyl]benzamide;

$N^1$-[2-(4-Amino-1H-imidazo[4,5-c]quinolin-1-yl)ethyl]benzamide;

$N^1$-[3-(4-Amino-2-methyl-1H-imidazo[4,5-c]quinolin-1-yl)propyl]benzamide;

$N^1$-[6-(4-Amino-1H-imidazo[4,5-c]quinolin-1-yl)hexyl]benzamide;

$N^1$-[4-(4-Amino-1H-imidazo[4,5-c]quinolin-1-yl)butyl]-3-phenylpropanamide;

$N^1$-[2-(4-Amino-1H-imidazo[4,5-c]quinolin-1-yl)ethyl]-3-phenylpropanamide;

$N^1$-[4-(4-Amino-1H-imidazo[4,5-c]quinolin-1-yl)butyl]-2-phenoxyacetamide;

$N^1$-[4-(4-Amino-1H-imidazo[4,5-c]quinolin-1-yl)butyl]-2-ethylhexanamide;

$N^1$-[4-(4-Amino-1H-imidazo[4,5-c]quinolin-1-yl)butyl]-2-phenoxypropanamide;

$N^1$-[4-(4-Amino-1H-imidazo[4,5-c]quinolin-1-yl)butyl]-2-chlorobenzamide;

$N^1$-[4-(4-Amino-1H-imidazo[4,5-c]quinolin-1-yl)butyl]-3,4-dichlorobenzamide;

$N^1$-[4-(4-Amino-1H-imidazo[4,5-c]quinolin-1-yl)butyl]-2,6-dichlorobenzamide;

$N^1$-[4-(4-Amino-1H-imidazo[4,5-c]quinolin-1-yl)butyl]-4-fluorobenzamnide;

$N^1$-[4-(4-Amino-1H-imidazo[4,5-c]quinolin-1-yl)butyl]-4-chlorobenzamide;

$N^1$-[4-(4-Amino-1H-imidazo[4,5-c]quinolin-1-yl)butyl]-4-methoxybenzamide;

$N^1$-[4-(4-Amino-1H-imidazo[4,5-c]quinolin-1-yl)butyl]-4-(trifluoromethyl)benzamide;

$N^1$-[4-(4-Amino-1H-imidazo[4,5-c]quinolin-1-yl)butyl]-2-phenylacetamide;

$N^1$-[4-(4-Amino-1H-imidazo[4,5-c]quinolin-1-yl)butyl]-(E)-3-phenyl-2-propenamide;

$N^1$-[4-(4-Amino-1H-imidazo[4,5-c]quinolin-1-yl)butyl]-3-cyclopentylpropanamide;

$N^1$-[4-(4-Amino-1H-imidazo[4,5-c]quinolin-1-yl)butyl]-1-cyclopentanecarboxamide;

$N^1$-[4-(4-Amino-1H-imidazo[4,5-c]quinolin-1-yl)butyl]-1-cyclohexanecarboxamide;

$N^1$-{4-[4-Amino-2-(2-methoxyethyl)-1H-imidazo[4,5-c]quinolin-1-yl]butyl}-2-methylbenzamide;

$N^1$-{4-[4-Amino-2-(2-methoxyethyl)-1H-imidazo[4,5-c]quinolin-1-yl]butyl}-1-cyclopentanecarboxamide;

$N^1$-{4-[4-Amino-2-(2-methoxyethyl)-1H-imidazo[4,5-c]quinolin-1-yl]butyl}-1-cyclohexanecarboxamide, $N^1$-{4-[4-Amino-2-(2-methoxyethyl)-6,7,8,9-tetrahydro-1H-imidazo[4,5-c]quinolin-1-yl]butyl}benzamide;

$N^1$-{4-[4-Amino-2-(2-methoxyethyl)-6,7,8,9-tetrahydro-1H-imidazo[4,5-c]quinolin-1-yl]butyl}-2-phenylacetamide;

$N^1$-[4-(4-Amino-2-(4-methoxybenzyl)-1H-imidazo[4,5-c]quinolin-1-yl)butyl]acetamide;

$N^1$-[4-(4-Amino-2-(2-methoxyethyl)-1H-imidazo[4,5-c]quinolin-1-yl)butyl]acetamide;

$N^1$-[4-(4-Amino-2-(2-methoxyethyl)-1H-imidazo[4,5-c]quinolin-1-yl)butyl]-2,2,2trifluoroacetamide;

$N^1$-[4-(4-Amino-1H-imidazo[4,5-c]quinolin-1-yl)butyl]-2,2,2-trifluoroacetamide;

$N^1$-[4-(4-Amino-1H-imidazo[4,5-c]quinolin-1-yl)butyl]-(trans)-2-phenylcyclopropane-1-carboxamide; and $N^1$-{4-[4-Amino-2-(2-methoxyethyl)-1H-imidazo[4,5-c]quinolin-1-yl]butyl}-(trans)-2-phenylcyclopropane-1-carboxamide in combination with a pharmaceutically acceptable carrier.

38. A compound selected from the group consisting of:

$N^6$-[4-(4-Amino-1H-imidazo[4,5-c]quinolin-1-yl)butyl]-6-quinolinecarboxamide;

$N^3$-[4-(4-Amino-1H-imidazo[4,5-c]quinolin-1-yl)butyl]-3-quinolinecarboxamide;

$N^3$-[4-(4-Amino-1H-imidazo[4,5-c]quinolin-1-yl)butyl]-2,6-dimethoxynicotinamide;

$N^8$-[4-(4-Amino-1H-imidazo[4,5-c]quinolin-1-yl)butyl]-8-quinolinecarboxamide;

$N^3$-[4-(4-Amino-1H-imidazo[4,5-c]quinolin-1-yl)butyl]nicotinamide;

$N^4$-[4-(4-Amino-1H-imidazo[4,5-c]quinolin-1-yl)butyl]isonicotinamide;

$N^4$-[4-(4-Amino-1H-imidazo[4,5-c]quinolin-1-yl)butyl]-4-quinolinecarboxamide;

$N^4$-[4-(4-Amino-2-(2-methoxyethyl)-1H-imidazo[4,5-c]quinolin-1-yl)butyl]-2-phenyl-4-quinolinecarboxamide;

$N^3$-[4-(4-Amino-1H-imidazo[4,5-c]quinolin-1-yl)butyl]-2-(pentylsulfanyl)nicotinamide;

$N^3$-[4-(4-Amino-1H-imidazo[4,5-c]quinolin-1-yl)butyl]-6-cyanonicotinamide;

$N^3$-[4-(4-Amino-1H-imidazo[4,5-c]quinolin-1-yl)butyl]-6-chloronicotinamide;

$N^3$-[4-(4-Amino-1H-imidazo[4,5-c]quinolin-1-yl)butyl]-6-(2,2,2-trifluoroethoxy)nicotinamide;

N²-{4-[4-Amino-2-(2-methoxyethyl)-1H-imidazo[4,5-c]quinolin-1-yl]butyl}-2-quinolinecarboxamide;
N¹-{4-[4-Amino-2-(2-methoxyethyl)-1H-imidazo[4,5-c]quinolin-1-yl]butyl}-1-isoquinolinecarboxamide;
N²-{4-[4-Amino-2-(2-methoxyethyl)-1H-imidazo[4,5-c]quinolin-1-yl]butyl}-5-butyl-2-pyridinecarboxamide;
N³-{4-[4-Amino-2-(2-methoxyethyl)-1H-imidazo[4,5-c]quinolin-1-yl]butyl}-3-indolecarboxamide;
N²-{4-[4-Amino-2-(4-methoxybenzyl)-1H-imidazo[4,5-c]quinolin-1-yl]butyl}-2-quinolinecarboxamide;
N³-{4-[4-Amino-2-(2-methoxyethyl)-1H-imidazo[4,5-c]quinolin-1-yl]butyl}-6-(1-pyrrolyl)nicotinamide;
N⁵-{4-[4-Amino-2-(2-methoxyethyl)-1H-imidazo[4,5-c]quinolin-1-yl]butyl}-5-indolecarboxamide;
N³-{4-[4-Amino-2-(2-methoxyethyl)-1H-imidazo[4,5-c]quinolin-1-yl]butyl}-5-(2-phenyl-1-ethynyl)nicotinamide;
N³-[4-(4-Amino-2-phenyl-1H-imidazo[4,5-c]quinolin-1-yl)butyl]nicotinamide;
N²-[4-(4-Amino-2-phenyl-1H-imidazo[4,5-c]quinolin-1-yl)butyl]-2-quinolinecarboxamide;
N³-[4-(4-Amino-1H-imidazo[4,5-c]quinolin-1-yl)butyl]-2-chloronicotinamide;
N¹-[4-(4-Amino-1H-imidazo[4,5-c]quinolin-1-yl)butyl]-2-(2-thienyl)acetamide;
N¹-[4-(4-Amino-2-(2-methoxyethyl)-1H-imidazo[4,5-c]quinolin-1-yl)butyl]-2-(3thienyl)acetamide;
N²-{4-[4-Amino-2-(4-methoxybenzyl)-1H-imidazo[4,5-c]quinolin-1-yl]butyl}-2-pyridinecarboxamide;
N³-{4-[4-Amino-2-(4-methoxybenzyl)-1H-imidazo[4,5-c]quinolin-1-yl]butyl}-nicotinamide;
N⁴-{4-[4-Amino-2-(2-methoxyethyl)-6,7,8,9-tetrahydro-1H-imidazo[4,5-c]quinolin-1-yl]butyl}isonicotinamide;
N³-{4-[4-Amino-2-(2-methoxyethyl)-1H-imidazo[4,5-c]quinolin-1-yl]butyl}-3-furamide;
N³-{4-[4-Amino-2-(2-methoxyethyl)-1H-imidazo[4,5-c]quinolin-1-yl]butyl}nicotinamide;
N²-[4-(4-Amino-1H-imidazo[4,5-c]quinolin-1-yl)butyl]-2-furamide;
N²-[4-(4-Amino-1H-imidazo[4,5-c]quinolin-1-yl)butyl]-2-thiophenecarboxamide; and
N²-[4-(4-Amino-1H-imidazo[4,5-c]quinolin-1-yl)butyl]-5-nitro-2-furamide.

39. A compound selected from the group consisting of:

N¹-[4-(4-Amino-2-butyl-1H-imidazo[4,5-c]quinolin-1-yl)butyl]-5-(2-oxoperhydrothieno[3,4-d]imidazol-4-yl)pentanamide;
N¹-[4-(4-Amino-1H-imidazo[4,5-c]quinolin-1-yl)butyl]-5-(2-oxoperhydrothieno[3,4-d]imidazol-4-yl)pentanamide;
N¹-[2-(4-Amino-2-butyl-1H-imidazo[4,5-c]quinolin-1-yl)ethyl]-5-(2-iminoperhydrothieno[3,4-d]imidazol-4-yl)pentanamide;
N¹-[2-(4-Amino-2-butyl-1H-imidazo[4,5-c]quinolin-1-yl)ethyl]-5-(2-oxoperhydrothieno[3,4-d]imidazol-4-yl)pentanamide; and
N¹-[2-(4-Amino-2-(ethoxymethyl)-1H-imidazo[4,5-c]quinolin-1-yl)ethyl]-5-(2-oxoperhydrothieno[3,4-d]imidazol-4-yl)pentanamide.

40. A compounds selected from the group consisting of:

N¹-[4-(4-Amino-1H-imidazo[4,5-c]quinolin-1-yl)butyl]-4-(morpholinomethyl)benzamide;
N¹-[4-(4-Amino-1H-imidazo[4,5-c]quinolin-1-yl)butyl]-4-{[(4-pyridylmethyl)amino]methyl}benzamide;
N¹-[4-(4-Amino-1H-imidazo[4,5-c]quinolin-1-yl)butyl]-4-{[(2-methoxyphenethyl)amino]methyl}benzamide;
N¹-[4-(4-Amino-1H-imidazo[4,5-c]quinolin-1-yl)butyl]-4-({methyl[2-(2-pyridyl)ethyl]amino}methyl)benzamide;
N¹-{4-[4-Amino-2-(2-methoxyethyl)-1H-imidazo[4,5-c]quinolin-1-yl]butyl}-2-oxo-2-phenylacetamide;
N¹-[4-(4-Amino-1H-imidazo[4,5-c]quinolin-1-yl)butyl]-4-[(2-tetrahydro-1H-1-pyrrolyl-1H-benzo[d]imidazol-1-yl)methyl]benzamide; and
N³-[4-(4-Amino-1H-imidazo[4,5-c]quinolin-1-yl)butyl]-6-morpholinonicotinamide.

41. A compound selected from the group consisting of:

N¹-[4-(4-amino-1H-imidazo[4,5-c]quinolin-1-yl)butyl]-N¹-(4-methoxybenzyl)acetamide;
N¹-[4-(4-amino-1H-imidazo[4,5-c]quinolin-1-yl)butyl]-N¹-(4-bromobenzyl)acetamide;
N¹-[4-(4-amino-1H-imidazo[4,5-c]quinolin-1-yl)butyl]-N¹-(5-bromo-2-hydroxybenzyl)-acetamide;
N¹-[4-(4-amino-1H-imidazo[4,5-c]quinolin-1-yl)butyl]-N¹-(4-butoxybenzyl)acetamide;
N¹-[4-(4-amino-1H-imidazo[4,5-c]quinolin-1-yl)butyl]-N¹-(2-chlorobenzyl)acetamide;
N¹-[4-(4-amino-1H-imidazo[4,5-c]quinolin-1-yl)butyl]-N¹-(2-chloro-5-nitrobenzyl)acetamide;
N¹-[4-(4-amino-1H-imidazo[4,5-c]quinolin-1-yl)butyl]-N¹-(5-chloro-2-nitrobenzyl)acetamide;
N¹-[4-(4-amino-1H-imidazo[4,5-c]quinolin-1-yl)butyl]-N¹-2-[(4-chlorophenyl)sulfanyl]benzylacetamide;
N¹-[4-(4-amino-1H-imidazo[4,5-c]quinolin-1-yl)butyl]-N¹-(3,5-dichlorobenzyl)acetamide;
N¹-[4-(4-amino-1H-imidazo[4,5-c]quinolin-1-yl)butyl]-N¹-(3,4-difluorobenzyl)acetamide;
N¹-[4-(4-amino-1H-imidazo[4,5-c]quinolin-1-yl)butyl]-N¹-(2,5-dimethoxybenzyl)acetamide;
N¹-[4-(4-amino-1H-imidazo[4,5-c]quinolin-1-yl)butyl]-N¹-(2,3-dimethoxybenzyl)acetamide;
N¹-[4-(4-amino-1H-imidazo[4,5-c]quinolin-1-yl)butyl]-N¹-(2,4-dimethylbenzyl)acetamide;
N¹-[4-(4-amino-1H-imidazo[4,5-c]quinolin-1-yl)butyl]-N¹-[(5-ethyl-2-furyl)methyl]acetamide;
N¹-[4-(4-amino-1H-imidazo[4,5-c]quinolin-1-yl)butyl]-N¹-(2-furylmethyl)acetamide;
N¹-[4-(4-amino-1H-imidazo[4,5-c]quinolin-1-yl)butyl]-N¹-(3-furylmethyl)acetamide;
N¹-[4-(4-amino-1H-imidazo[4,5-c]quinolin-1-yl)butyl]-N¹-(3-phenylpropyl)acetamide;
N¹-[4-(4-amino-1H-imidazo[4,5-c]quinolin-1-yl)butyl]-N¹-octylacetamide;
N¹-[4-(4-amino-1H-imidazo[4,5-c]quinolin-1-yl)butyl]-N¹-(1-naphthylmethyl)acetamide;
N¹-[4-(4-amino-1H-imidazo[4,5-c]quinolin-1-yl)butyl]-N¹-[(2-methoxy-1naphthylmethyl]acetamide;
N¹-[4-(4-amino-1H-imidazo[4,5-c]quinolin-1-yl)butyl]-N¹-(4-nitrobenzyl)acetamide;
N¹-[4-(4-amino-1H-imidazo[4,5-c]quinolin-1-yl)butyl]-N¹-(2-nitrobenzyl)acetamide;
N¹-[4-(4-amino-1H-imidazo[4,5-c]quinolin-1-yl)butyl]-N¹-(4-pyridylmethyl)acetamide;
N¹-[4-(4-amino-1H-imidazo[4,5-c]quinolin-1-yl)butyl]-N¹-(2-methylbenzyl)acetamide;
N¹-[4-(4-amino-1H-imidazo[4,5-c]quinolin-1-yl)butyl]-N¹-(2,3,4-trimethoxybenzyl)acetamide;
N¹-[4-(4-amino-1H-imidazo[4,5-c]quinolin-1-yl)butyl]-N¹-(3,4,5-trimethoxybenzyl)acetamide;
N¹-[4-(4-amino-1H-imidazo[4,5-c]quinolin-1-yl)butyl]-N¹-cyclopentylacetamide;
N¹-[4-(4-amino-1H-imidazo[4,5-c]quinolin-1-yl)butyl]-N¹-(4-fluorophenyl)acetamide;
N¹-[4-(4-amino-1H-imidazo[4,5-c]quinolin-1-yl)butyl]-N¹-isopropylacetamide;

N¹-[4-(4-amino-1H-imidazo[4,5-c]quinolin-1-yl)butyl]-N¹-
[4-(trifluoromethyl)phenyl]acetamide;
N¹-[4-(4-amino-1H-imidazo[4,5-c]quinolin-1-yl)butyl]-N¹-
cyclohexylmethylacetamide;
N¹-[4-(4-amino-1H-imidazo[4,5-c]quinolin-1-yl)butyl]-N¹-
benzylacetamide;
N¹-[4-(4-amino-1H-imidazo[4,5-c]quinolin-1-yl)butyl]-N¹-
methylacetamide;
N¹-[4-(4-amino-1H-imidazo[4,5-c]quinolin-1-yl)butyl]-N¹-
ethylacetamide; and
N¹-[4-(4-amino-1H-imidazo[4,5-c]quinolin-1-yl)butyl]-N¹-
benzyl-2,2,2-trifluoroacetamide.

42. A pharmaceutical composition comprising a therapeutically effective amount of a compound of claim 9 in combination with a pharmaceutically acceptable carrier.

43. A pharmaceutical composition comprising a therapeutically effective amount of a compound of claim 20 in combination with a pharmaceutically acceptable carrier.

44. A pharmaceutical composition comprising a therapeutically effective amount of a compound of claim 29 in combination with a pharmaceutically acceptable carrier.

45. A method of inducing cytokine biosynthesis in an animal comprising administering an effective amount of a composition of claim 1 to the animal.

46. A method of treating a viral disease in an animal comprising administering an effective amount of a composition of claim 1 to the animal.

47. A method of treating a neoplastic disease in an animal comprising administering an effective amount of a composition of claim 1 to the animal.

48. A method of inducing cytokine biosynthesis in an animal comprising administering an effective amount of a composition of claim 8 to the animal.

49. A method of treating a viral disease in an animal comprising administering an effective amount of a composition of claim 8 to the animal.

50. A method of treating a neoplastic disease in an animal comprising administering an effective amount of a composition of claim 8 to the animal.

51. A method of inducing cytokine biosynthesis in an animal comprising administering an effective amount of a compound of claim 9 to the animal.

52. A method of treating a viral disease in an animal comprising administering an effective amount of a compound of claim 9 to the animal.

53. A method of treating a neoplastic disease in an animal comprising administering an effective amount of a compound of claim 9 to the animal.

54. A method of inducing cytokine biosynthesis in an animal comprising administering an effective amount of a compound of claim 20 to the animal.

55. A method of treating a viral disease in an animal comprising administering an effective amount of a compound of claim 20 to the animal.

56. A method of treating a neoplastic disease in an animal comprising administering an effective amount of a compound of claim 20 to the animal.

57. A method of inducing cytokine biosynthesis in an animal comprising administering an effective amount of a compound of claim 29 to the animal.

58. A method of treating a viral disease in an animal comprising administering an effective amount of a compound of claim 29 to the animal.

59. A method of treating a neoplastic disease in an animal comprising administering an effective amount of a compound of claim 29 to the animal.

60. A pharmaceutical composition comprising a therapeutically effective amount of a compound of the formula (Ia):

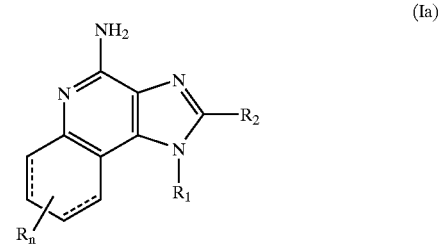

(Ia)

wherein
  $R_1$ is -alkyl-$NR_3$—CO—$R_4$ or -alkenyl-$NR_3$—CO—$R_4$
    wherein $R_4$ is aryl, heteroaryl, alkyl or alkenyl, each of
    which may be unsubstituted or substituted by one or
    more substituents selected from the group consisting
    of:
    -heterocyclyl;
    -(substituted heterocyclyl);
    -(alkyl)$_{0-1}$heterocyclyl;
    -(alkyl)$_{0-1}$(substituted heterocyclyl);
    —O-(alkyl)$_{0-1}$heterocyclyl;
    —O-(alkyl)$_{0-1}$(substituted heterocyclyl);
    —S(O)$_{0-2}$-(alkyl)$_{0-1}$heterocyclyl; and
    —S(O)$_{0-2}$-(alkyl)$_{0-1}$(substituted heterocyclyl);
  $R_2$ is selected from the group consisting of:
    -hydrogen;
    -alkyl;
    -alkenyl;
    -aryl;
    -(substituted aryl);
    -heteroaryl;
    -(substituted heteroaryl);
    -heterocyclyl;
    -(substituted heterocyclyl);
    -alkyl-O-alkyl;
    -alkyl-O-alkenyl; and
    -alkyl or alkenyl substituted by one or more substituents selected from the group consisting of:
      —OH;
      -halogen;
      —N($R_3$)$_2$;
      —CO—N($R_3$)$_2$;
      —CO—$C_{1-10}$ alkyl;
      —CO—O—$C_{1-10}$ alkyl;
      —$N_3$;
      -aryl;
      -(substituted aryl);
      -heteroaryl;
      -(substituted heteroaryl);
      -heterocyclyl;
      -(substituted heterocyclyl);
      —CO-aryl; and
      —CO-heteroaryl;
  each $R_3$ is independently selected from the group consisting of hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;
  n is 0 to 4;
  and each R present is independently selected from the group consisting of $C_{1-10}$ alkyl, $C_{1-10}$ alkoxy, halogen and trifluoromethyl, or a pharmaceutically acceptable salt thereof, in combination with a pharmaceutically acceptable carrier.

61. A method of inducing cytokine biosynthesis in an animal comprising administering an effective amount of a composition of claim 60 to the animal.

62. A method of treating a viral disease in an animal comprising administering an effective amount of a composition of claim 60 to the animal.

63. A method of treating a neoplastic disease in an animal comprising administering an effective amount of a composition of claim 60 to the animal.

64. The composition of claim 60 wherein $R_4$ is

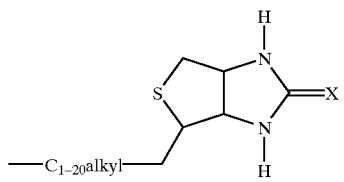

and X is O, S, or NH.

UNITED STATES PATENT AND TRADEMARK OFFICE
CERTIFICATE OF CORRECTION

PATENT NO.   : 6,451,810 B1
DATED        : September 17, 2002
INVENTOR(S)  : Coleman, Patrick L.

It is certified that error appears in the above-identified patent and that said Letters Patent is hereby corrected as shown below:

Column 2,
Line 24, delete "conditionssuch" and insert in place thereof -- conditions such --.

Column 5,
Line 11, delete "0to" and insert in place thereof -- 0 to --.

Column 10,
Line 23, delete "0to" and insert in place thereof -- 0 to --.

Column 35,
Line 2, delete "aminoethyly" and insert in place thereof -- aminoethyl --.

Column 41,
Line 34, delete "mnmol)" and insert in place thereof -- mmol) --.

Column 42,
Line 26, delete "dichioromethane" and insert in place thereof -- dichloromethane --.

Column 51,
Line 48, delete "arninobutyl" and insert in place thereof -- aminobutyl --.

Column 58,
Line 36, delete "$C_{25}H_{3}oN_{6}0S$" and insert in place thereof -- $C_{25}H_{30}N_{6}0S$ --.

Column 59,
Line 41, delete "$C_{20}HI_{9}N_{6}0CI)$" and insert in place thereof -- $C_{20}H_{19}N_{6}OCI)$ --.

Column 70,
Line 26, delete "tic" and insert in place thereof -- tlc --.

UNITED STATES PATENT AND TRADEMARK OFFICE
CERTIFICATE OF CORRECTION

PATENT NO.   : 6,451,810 B1
DATED        : September 17, 2002
INVENTOR(S)  : Coleman, Patrick L.

It is certified that error appears in the above-identified patent and that said Letters Patent is hereby corrected as shown below:

<u>Column 137,</u>
Line 42, delete "R4" and insert in place thereof -- $R_4$ --.

<u>Column 149,</u>
Line 67, delete "fluorobenzamnide;" and insert place thereof -- fluorobenzamide; --.

Signed and Sealed this

Thirteenth Day of May, 2003

JAMES E. ROGAN
*Director of the United States Patent and Trademark Office*